(12) United States Patent
Brodnick et al.

(10) Patent No.: US 10,357,168 B2
(45) Date of Patent: Jul. 23, 2019

(54) TIME TRANSFORMATION OF LOCAL ACTIVATION TIMES

(71) Applicant: APN Health, LLC, Pewaukee, WI (US)

(72) Inventors: Donald Brodnick, Cedarburg, WI (US); Jasbir Sra, Pewaukee, WI (US)

(73) Assignee: APN Health, LLC, Pewaukee, WI (US)

( * ) Notice: Subject to any disclaimer, the term of this patent is extended or adjusted under 35 U.S.C. 154(b) by 282 days.

(21) Appl. No.: 15/062,697

(22) Filed: Mar. 7, 2016

(65) Prior Publication Data

US 2017/0251942 A1    Sep. 7, 2017

(51) Int. Cl.
| | | |
|---|---|---|
| A61B 5/04 | (2006.01) | |
| A61B 5/00 | (2006.01) | |
| A61B 5/0408 | (2006.01) | |
| A61B 5/0468 | (2006.01) | |

(52) U.S. Cl.
CPC ........ A61B 5/04012 (2013.01); A61B 5/7221 (2013.01); *A61B 5/04017* (2013.01); *A61B 5/0468* (2013.01); *A61B 5/04085* (2013.01)

(58) Field of Classification Search
CPC . A61B 5/0432; A61B 5/04012; A61B 5/7221; A61B 5/0468
See application file for complete search history.

(56) References Cited

U.S. PATENT DOCUMENTS

| | | |
|---|---|---|
| 4,240,442 A | 12/1980 | Andresen et al. |
| 4,374,382 A | 2/1983 | Markowitz et al. |
| 4,583,553 A | 4/1986 | Shah et al. |
| 5,117,824 A | 6/1992 | Keimel et al. |
| 5,365,426 A | 11/1994 | Siegel et al. |
| 5,462,060 A | 10/1995 | Jacobson et al. |

(Continued)

FOREIGN PATENT DOCUMENTS

| | | |
|---|---|---|
| EP | 1745740 A1 | 1/2007 |
| EP | 2047794 A1 | 4/2009 |

(Continued)

OTHER PUBLICATIONS

Pan et al. A Real-Time QRS Detection Algorithm. IEEE Transactions on Biochemical Engineering. vol. BME-32, No. 3, Mar. 1985. <http://mirel.xmu.edu.cn/mirel/public/reaching/QRSdetection.pdf>.

(Continued)

*Primary Examiner* — Michael J D Abreau
(74) *Attorney, Agent, or Firm* — Jansson Munger; McKinley & Kirby Ltd.

(57) ABSTRACT

An automatic method of determining local activation time (LAT) from at least three multi-channel cardiac electrogram signals including a mapping channel and a plurality of reference channels. The method comprises (a) storing the cardiac channel signals, (b) using the mapping-channel signal and a first reference-channel signal to compute LAT values at a plurality of mapping-channel locations, (c) monitoring the timing stability of the first reference-channel signal, and (d) if the timing stability of the monitored signal falls below a stability standard, using the signal of a second reference channel to determine LAT values. Substantial loss of LAT values is avoided in spite of loss of timing stability.

27 Claims, 34 Drawing Sheets

(56) References Cited

U.S. PATENT DOCUMENTS

| | | |
|---|---|---|
| 5,526,813 A | 6/1996 | Yoshida |
| 5,546,951 A | 8/1996 | Ben-Haim |
| 5,560,367 A | 10/1996 | Haardt et al. |
| 5,560,368 A | 10/1996 | Berger |
| 5,701,907 A | 12/1997 | Klammer |
| 6,236,883 B1 | 5/2001 | Ciaccio et al. |
| 6,301,496 B1 | 10/2001 | Reisfeld |
| 6,526,313 B2 | 2/2003 | Sweeney et al. |
| 6,556,860 B1 | 4/2003 | Groenewegen |
| 6,937,888 B2 | 8/2005 | Kohler et al. |
| 7,107,093 B2 | 9/2006 | Burnes |
| 7,364,550 B1 | 4/2008 | Turcott |
| 7,561,912 B2 | 7/2009 | Schatz et al. |
| 7,610,084 B2 | 10/2009 | Sweeney et al. |
| 7,792,571 B2 | 9/2010 | Sweeney et al. |
| 7,890,170 B2 | 2/2011 | Ettori et al. |
| 8,041,417 B2 | 10/2011 | Jonckheere et al. |
| 8,064,995 B1 | 11/2011 | Dupelle et al. |
| 8,137,269 B2 | 3/2012 | Sheikhzadeh-Nadjar et al. |
| 8,150,503 B2 | 4/2012 | Schatz et al. |
| 8,478,388 B2 | 7/2013 | Nguyen et al. |
| 8,768,440 B1 | 7/2014 | Brodnick et al. |
| 8,812,091 B1 | 8/2014 | Brodnick |
| 2002/0045810 A1* | 4/2002 | Ben-Haim ............ A61B 5/0215 600/374 |
| 2002/0133085 A1 | 9/2002 | Kohler et al. |
| 2002/0138013 A1 | 9/2002 | Guerrero et al. |
| 2003/0216654 A1 | 11/2003 | Xu et al. |
| 2004/0015090 A1 | 1/2004 | Sweeney et al. |
| 2004/0059203 A1 | 3/2004 | Guerrero et al. |
| 2004/0186388 A1 | 9/2004 | Gerasimov |
| 2005/0245973 A1 | 11/2005 | Sherman |
| 2007/0161916 A1 | 7/2007 | Zantos et al. |
| 2008/0109041 A1 | 5/2008 | de Voir |
| 2009/0069704 A1 | 3/2009 | MacAdam et al. |
| 2009/0099468 A1 | 4/2009 | Thiagalingam et al. |
| 2010/0041975 A1 | 2/2010 | Chen et al. |
| 2010/0305645 A1 | 12/2010 | Sweeney et al. |
| 2011/0071375 A1 | 3/2011 | Baker, Jr. et al. |
| 2011/0137153 A1 | 6/2011 | Govari et al. |
| 2011/0172729 A1 | 7/2011 | Sweeney et al. |
| 2011/0251505 A1 | 10/2011 | Narayan et al. |
| 2011/0282226 A1 | 11/2011 | Benser et al. |
| 2011/0288605 A1 | 11/2011 | Kaib et al. |
| 2012/0035488 A1 | 2/2012 | MacAdam et al. |
| 2012/0101398 A1 | 4/2012 | Ramanathan et al. |
| 2012/0123279 A1 | 5/2012 | Brueser et al. |
| 2012/0130263 A1 | 5/2012 | Pretorius et al. |
| 2012/0179055 A1 | 7/2012 | Tamil et al. |
| 2012/0184864 A1 | 7/2012 | Harlev et al. |
| 2012/0197151 A1 | 8/2012 | Schatz et al. |
| 2013/0006131 A1 | 1/2013 | Narayan et al. |
| 2013/0030314 A1 | 1/2013 | Keel et al. |
| 2013/0066221 A1 | 3/2013 | Ryu et al. |
| 2013/0109945 A1 | 5/2013 | Harlev et al. |
| 2013/0184569 A1 | 7/2013 | Strommer et al. |
| 2013/0245477 A1 | 9/2013 | Brodnick et al. |
| 2013/0345583 A1 | 12/2013 | Thakur et al. |
| 2014/0323848 A1* | 10/2014 | He ........................ A61B 5/046 600/411 |
| 2015/0238102 A1 | 8/2015 | Rubinstein et al. |
| 2016/0089048 A1 | 3/2016 | Brodnick et al. |

FOREIGN PATENT DOCUMENTS

| | | |
|---|---|---|
| WO | 199619939 A1 | 7/1996 |
| WO | 2005002669 A2 | 1/2005 |
| WO | 2011088043 A1 | 7/2011 |
| WO | 2012056342 A2 | 5/2012 |

OTHER PUBLICATIONS

Friesen G.M. et al. "A Comparison of the Noise Sensitivity of None QRS Detection Alogrithyms," IEEE Transactions on Biomedical Engineering, IEEE Inc. New York, US, Bd. 37, Nr. 1, 1990, Seiten 85-98.

* cited by examiner

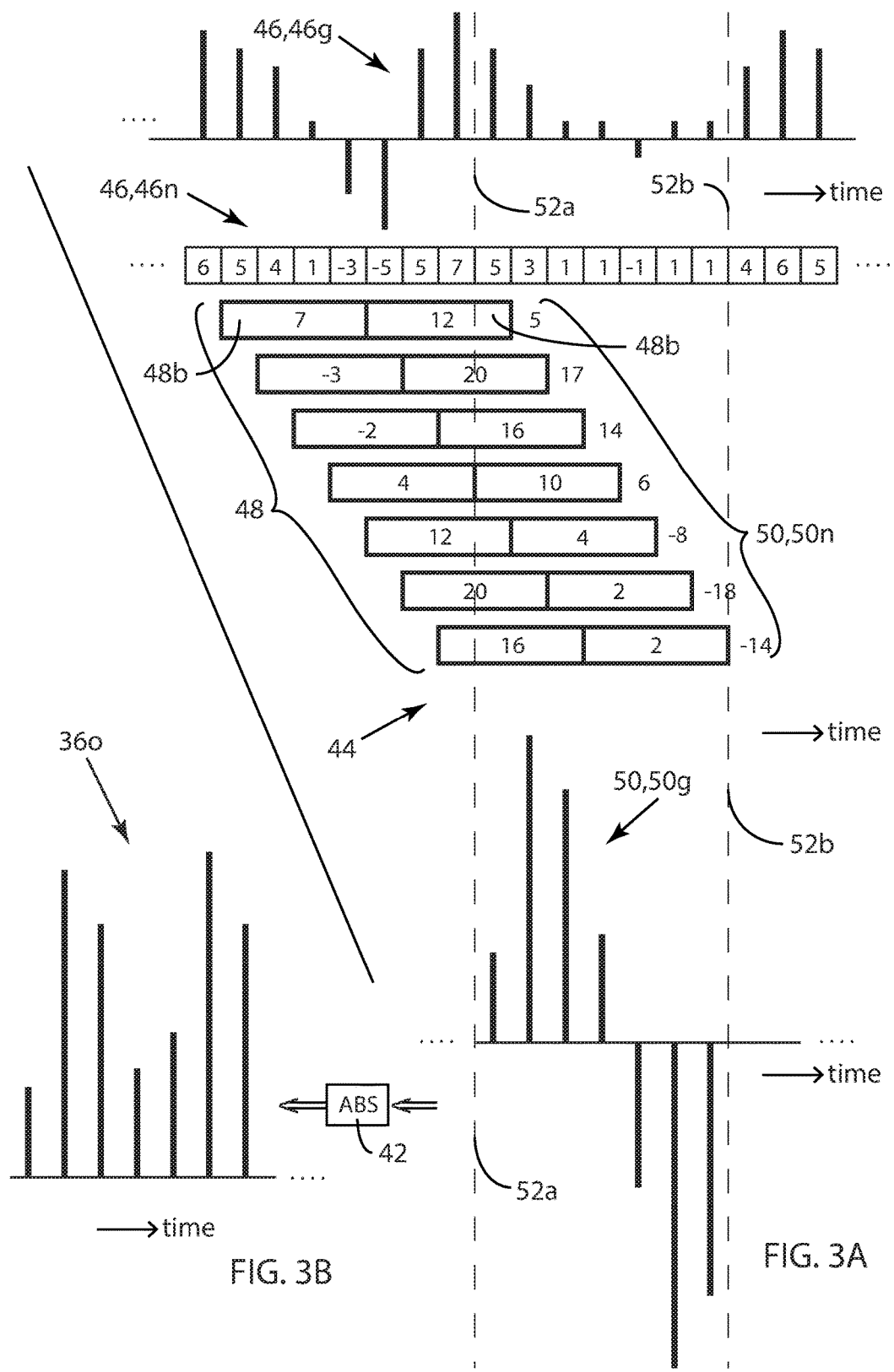

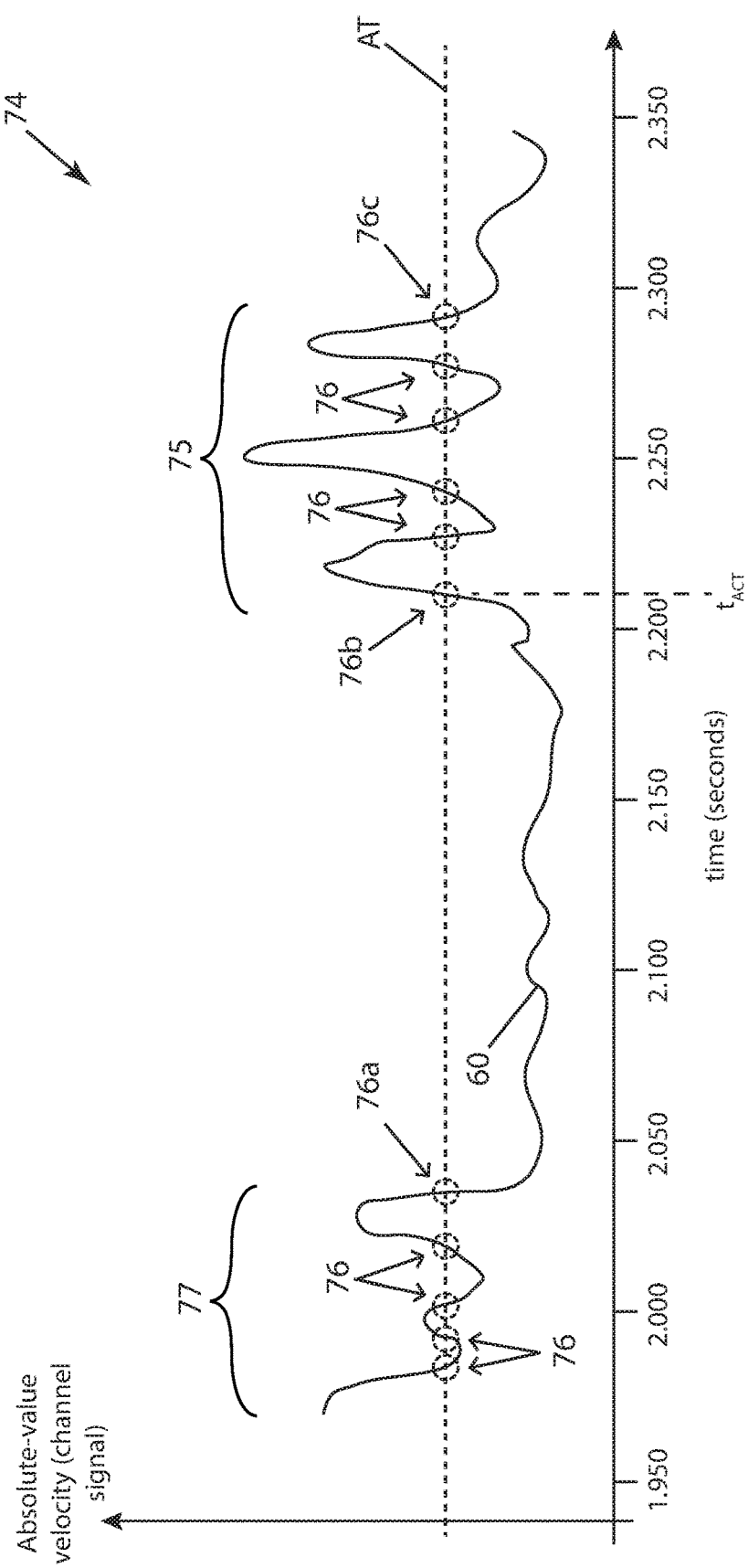

|   |   |   |   |   |   |
|---|---|---|---|---|---|
| | | CL = 341msec | | | |
| ACT | $t_{M-ACT}$ | $D_P$ | $D_F$ | $A_{SC}$ | Comment |
| 132a | | | | | Not detected; too early |
| 132b | 4382 | 41 | 9 | 50 | Beginning-of-data rule |
| 132c | 4732 | 9 | 15 | 24 | Selected activation |
| 132d | 5058 | 15 | 12 | 27 | |
| 132e | 5411 | 12 | 248 | 260 | End-of-data rule |
| 132f | | | | | Not detected; too small |

[all values in the table in msec]

TABLE LEGEND

CL = reference-channel cycle length $t_{M-ACT}(i)$ = mapping-channel activation times $D_P(i) = t_{M-ACT}(i) - t_{M-ACT}(i-1) - CL$ = deviation of prior interval from CL $D_F(i) = t_{M-ACT}(i+1) - t_{M-ACT}(i) - CL$ = deviation of future interval from CL

FIG. 7B

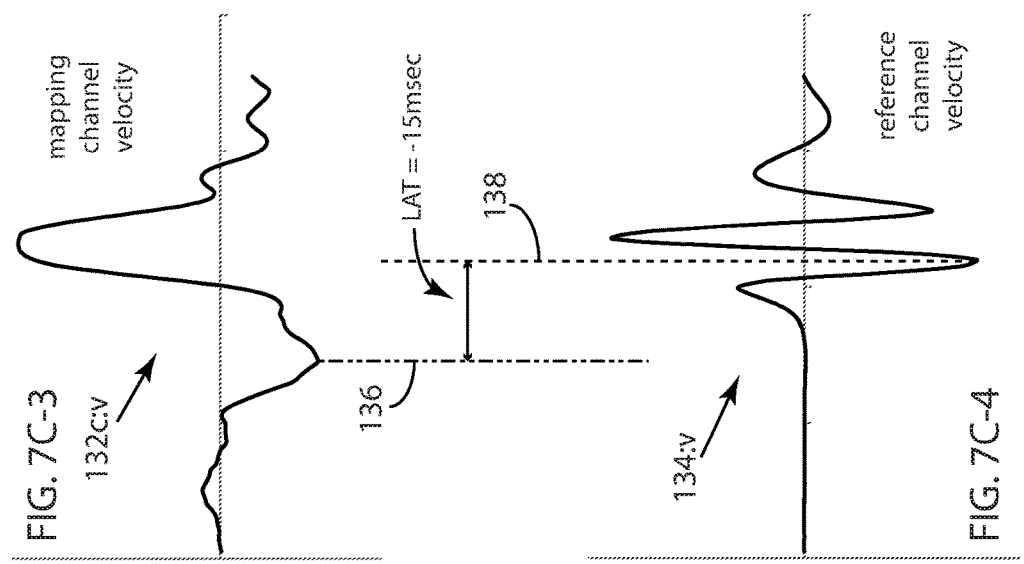
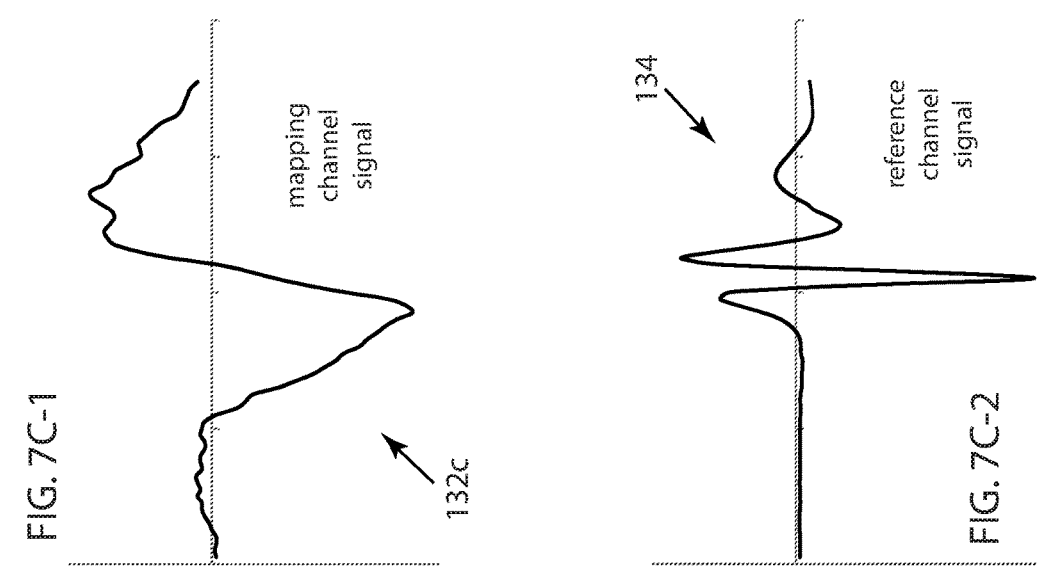

| | | | | | | | | | 214 | | | | |
|---|---|---|---|---|---|---|---|---|---|---|---|---|---|
| A: | 451 | 1594 | 1994 | 2333 | 2678 | 3024 | 3368 | 3703 | 4050 | 4387 | 4731 | 5069 | 5412 | 5749 |
| B: | 4884 | 4663 | 4722 | 4720 | 4724 | 4729 | 4732 | 4726 | 4732 | 4728 | 4731 | 4728 | 4730 | 4726 |
| C: | -168 | 53 | -6 | -4 | -8 | -13 | -16 | -10 | -16 | -12 | -15 | -12 | -14 | -10 |
| | | | | | | | | | | | | | | |
| D: | -168 | -16 | -16 | -15 | -14 | -13 | -12 | -12 | -10 | -10 | -8 | -6 | -4 | 53 |
| E: | | | | -15 | -14 | -13 | (-12) | -12 | -10 | -10 | | | | |

[All times in msec;    CL = 341 msec;    $t_M$ = 4716 msec]

TABLE LEGEND

Row A: fiducial times $t_R$ in reference channel of maximum negative velocity
Row B: adjusted fiducial times $t_{RA}$ (adjusted to within ±CL/2 of $t_M$ (CL = 341 msec; $t_M$ = 4716 msec)
Row C: intermediate LAT values = $t_M - t_{RA}$
Row D: ordered list of intermediate LAT values
Row E: interquartile set of intermediate LAT values measurement confidence interval = ±2.5msec (range is -15 to -10)

FIG. 7D

Automatic Reference-Channel Selection

309

| Timing Offset in msec | | two minute history stats | | before loss of timing stability | | after loss of timing stability | |
|---|---|---|---|---|---|---|---|
| Ref ch J | Ref ch K | mean | stdev | X | Z-score | X | Z-score |
| 1 | 2 | -22.5 | 4.85 | -24 | -0.3 | -17 | 1.1 |
| | 3 | 31.4 | 6.09 | 35 | 0.6 | 24 | -1.2 |
| | 4 | 42.3 | 8.80 | 48 | 0.6 | 45 | 0.3 |
| | 5 | 5.7 | 7.79 | 9 | 0.4 | 5 | -0.1 |
| | 6 | 1.0 | 8.71 | 0 | -0.1 | 2 | 0.1 |
| 2 | 3 | 58.0 | 6.76 | 61 | 0.4 | 60 | 0.3 |
| | 4 | 60.8 | 4.52 | 60 | -0.2 | 48 | -2.8 |
| | 5 | 33.0 | 4.92 | 32 | -0.2 | 27 | -1.2 |
| | 6 | 28.1 | 5.37 | 32 | 0.7 | 16 | -2.3 |
| 3 | 4 | 0.7 | 4.59 | 3 | 0.5 | -2 | -0.6 |
| | 5 | -22.4 | 6.44 | -12 | 1.6 | -19 | 0.5 |
| | 6 | -33.3 | 7.42 | -42 | -1.2 | -32 | 0.2 |
| 4 | 5 | -37.0 | 6.15 | -39 | -0.3 | -37 | 0.0 |
| | 6 | -54.4 | 5.38 | -50 | 0.8 | -56 | -0.3 |
| 5 | 6 | 0.2 | 5.51 | -5 | -0.9 | 3 | 0.5 |

FIG. 14

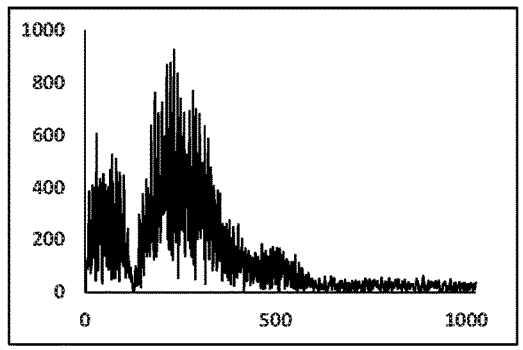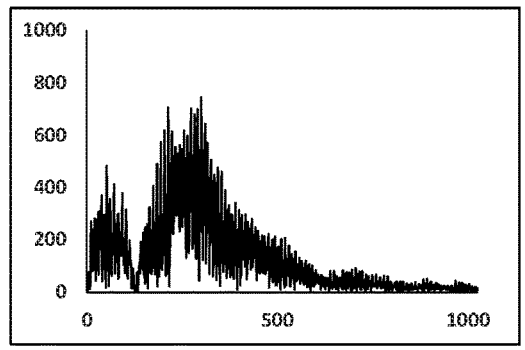
FIG. 15H  FIG. 15I
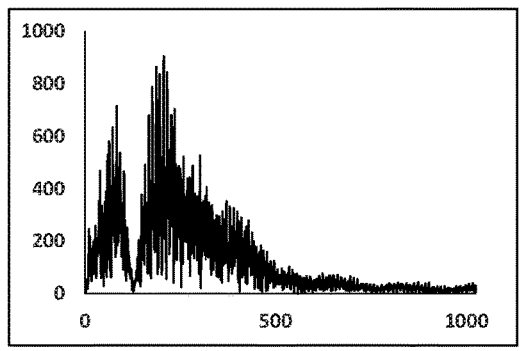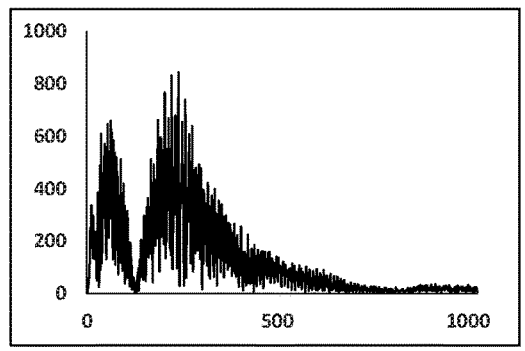
FIG. 15J  FIG. 15K
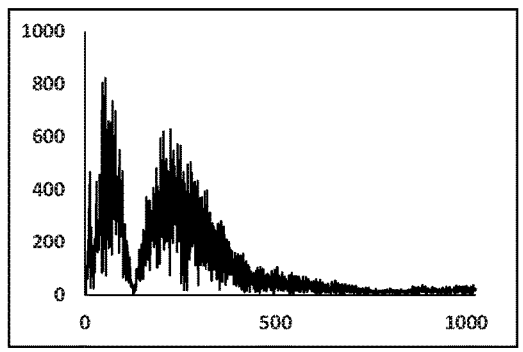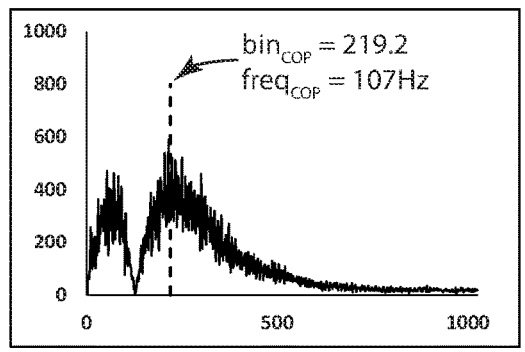
FIG. 15L  FIG. 15M

311

| Name | Wire | History mean | stdev | Current X | Isolated Z-score | Group Z-score | Combined Z-score |
|---|---|---|---|---|---|---|---|
| 1-HRA | 1 | 139.3 | 3.79 | 144 | 1.2 | 1.2 | 1.2 |
| 2-HIS | 2 | 203.5 | 1.05 | 201 | 2.4 | 2.4 | 2.4 |
| 3-A12 | 3 | 63.0 | 45.00 | 65 | 0.0 | 0.7 | 0.4 |
| 4-A34 | 3 | 21.3 | 16.96 | 10 | 0.7 | 0.7 | 0.7 |
| 5-A56 | 3 | 107.0 | 15.58 | 107 | 0.0 | 0.7 | 0.4 |
| 6-A78 | 3 | 13.5 | 8.27 | 31 | 2.1 | 0.7 | 1.4 |

Identifying Channels Causing Loss of Timing Stability

FIG. 15N

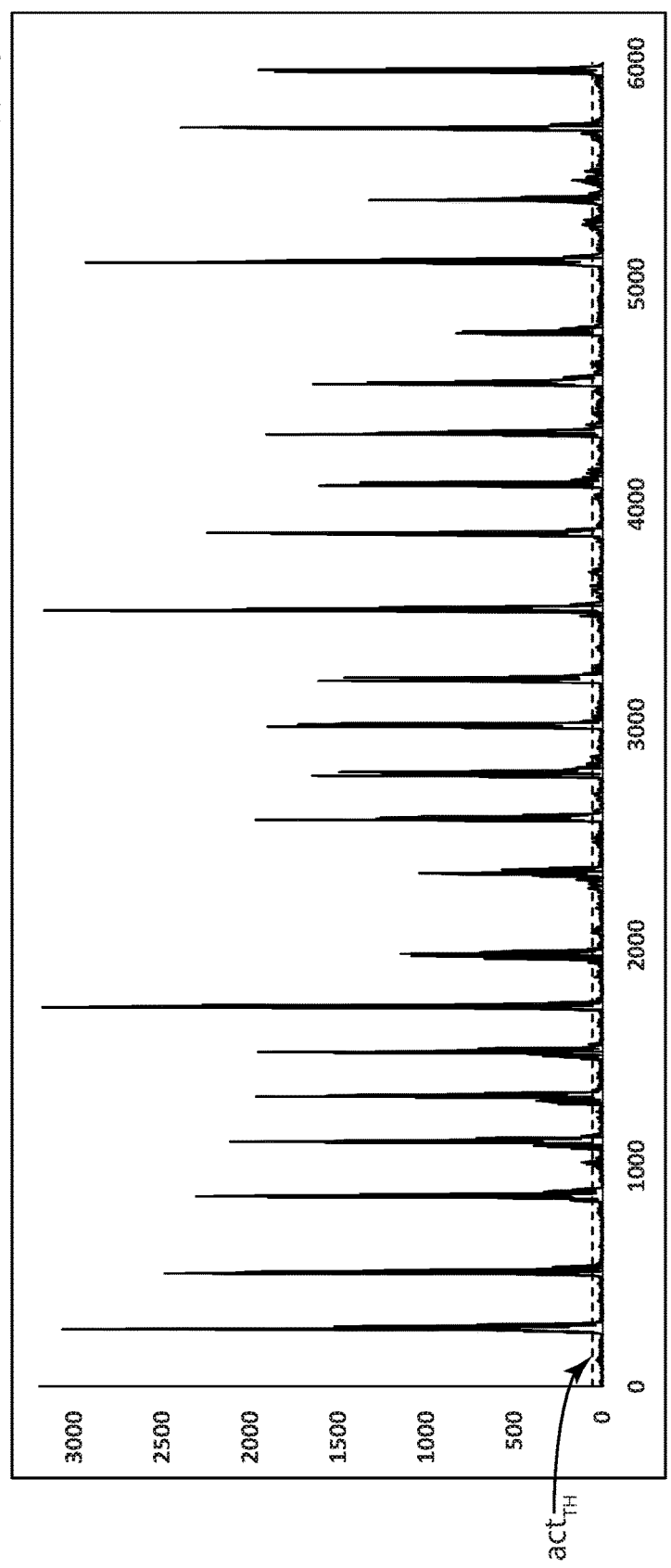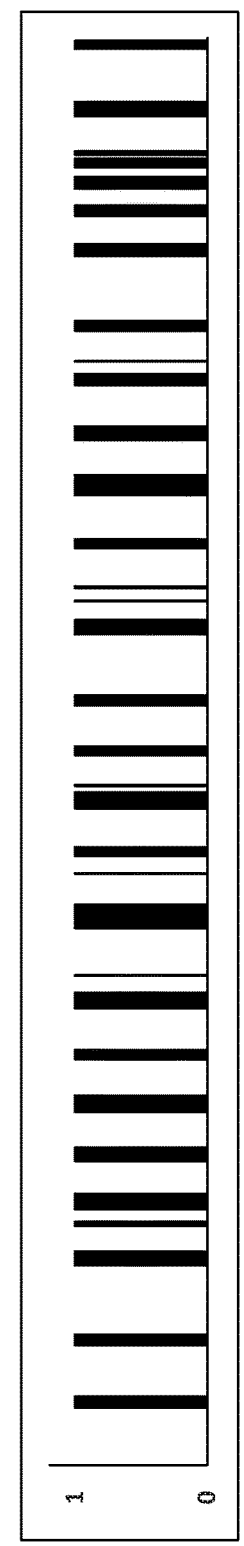

| | time (msec) | value (μvolts) |
|---|---|---|
| $max_E$ | 261 | -984 |
| $min_E$ | 3,521 | 747 | peak-to-peak = 1,731μvolts

| $H_1$ | $\Sigma$(all 2,048 signal values) |
|---|---|
| $H_2$ | $\Sigma$(2nd half of the signal values) - $\Sigma$(1st half of the signal values) |
| $H_3$ | $\Sigma$(2nd quarter of the signal values) - $\Sigma$(1st quarter of the signal values) |
| $H_4$ | $\Sigma$(4th quarter of the signal values) - $\Sigma$(3rd quarter of the signal values) |
| $H_5$ | $\Sigma$(2nd eighth of the signal values) - $\Sigma$(1st eighth of the signal values) |
| $H_6$ | $\Sigma$(4th eighth of the signal values) - $\Sigma$(3rd eighth of the signal values) |
| $H_7$ | $\Sigma$(6th eighth of the signal values) - $\Sigma$(5th eighth of the signal values) |
| $H_8$ | $\Sigma$(8th eighth of the signal values) - $\Sigma$(7th eighth of the signal values) |
| ⋮ | ⋮ |
| $H_{2047}$ | (2,046th signal value) - (2,045th signal value) |
| $H_{2048}$ | (2,048th signal value) - (2,047th signal value) |

FIG. 18G

|  | Aggregation | Frequency (Hz) |
|---|---|---|
| $A_1$ | $abs(H_2)$ | 0.488 |
| $A_2$ | $abs(H_3) + abs(H_4)$ | 0.977 |
| $A_3$ | $abs(H_5) + abs(H_6) + abs(H_7) + abs(H_8)$ | 1.953 |
| $A_4$ | $\Sigma [abs(H_9)$ through $abs(H_{16})]$ | 3.906 |
| $A_5$ | $\Sigma [abs(H_{17})$ through $abs(H_{32})]$ | 7.813 |
| $A_6$ | $\Sigma [abs(H_{33})$ through $abs(H_{64})]$ | 15.625 |
| $A_7$ | $\Sigma [abs(H_{65})$ through $abs(H_{128})]$ | 31.25 |
| $A_8$ | $\Sigma [abs(H_{129})$ through $abs(H_{256})]$ | 62.5 |
| $A_9$ | $\Sigma [abs(H_{257})$ through $abs(H_{512})]$ | 125 |
| $A_{10}$ | $\Sigma [abs(H_{513})$ through $abs(H_{1024})]$ | 250 |
| $A_{11}$ | $\Sigma [abs(H_{1025})$ through $abs(H_{2048})]$ | 500 |

FIG. 18H

TIME TRANSFORMATION OF LOCAL ACTIVATION TIMES

FIELD OF THE INVENTION

This invention is related generally to the field of electrophysiology, and more particularly to technology for accurate measurement of parameters within intracardiac and epicardial electrical signals such as heart rates and local activation times and the assessment of the quality of such measurements.

BACKGROUND OF THE INVENTION

The invention disclosed herein involves the processing of multiple channels of electrical signals produced by the heart. These channel signals include the signals from electrodes within the body, i.e., intracardiac signals from within vessels and chambers of the heart and epicardial signals from the outer surface of the heart. Throughout this document, the term "multi-channel cardiac electrogram" (or "MCCE") is used to refer to all of these types of channels; when specific types are appropriate, specific nomenclature is used. This terminology (MCCE) is used herein since the term "ECG" sometimes only refers to body-surface measurements of cardiac performance.

A major component in cardiac interventional procedures such as cardiac ablation is the display of cardiac data extracted from the MCCE signals captured by an array of electrodes placed within and on the structures of the heart itself. Among the important data displayed are intracardiac cycle length (time between the activations in arrhythmias (such as atrial fibrillation), relative time differences between related activations in two intracardiac channels to generate activation maps, and assessments of signal strength, variability and other measures of signal quality within MCCE signals.

Cardiac interventional electrophysiology procedures (e.g., ablation) can be extremely time-consuming, and the reliable determination and presentation of such cardiac parameters is an important element in both the quality of the procedures and the speed with which they can be carried out. Often the data presented to the electrophysiology doctor during such procedures exhibit high variability contributed not only by the performance of the heart itself but by unreliable detection of certain features of the MCCE signals. Therefore, there is a need for more reliable and more rapid algorithms to process intracardiac signals obtained during an electrophysiology (EP) procedure.

MCCE electrodes capture the electrical signals in the cardiac muscle cells. As mentioned above, some MCCE electrodes may be positioned inside cardiac veins, arteries and chambers (intracardiac) and on the outer surface of the heart (epicardial) as conductive elements at the tips or along the lengths of catheters introduced into the body and maneuvered into position by the EP doctor. The electrical signals within the heart muscles and which flow therefrom to other regions of the body have very low voltage amplitudes and therefore are susceptible to both external signal noise and internally-generated electrical variations (non-cardiac activity). In addition, cardiac arrhythmias themselves may be highly variable, which can make reliable extraction of cardiac parameters from MCCE signals difficult.

One important cardiac parameter used during such procedures is the time difference between the activations occurring within two channels, both of which contain the electrical signals of an arrhythmia. This measurement is called local activation time (LAT), and measurement of a plurality of values of LAT is the basis for the generation of an activation map. The map displays information about the sequence of activations of cardiac muscle cells relative to each other, and this sequence of information is combined with physical anatomical position information to form the map. An activation map then provides guidance to the EP doctor for the process of applying therapies to heart muscle cells which can terminate cardiac arrhythmias and permanently affect the heart to prevent recurrence of arrhythmias.

The entire process of determining LAT is referred to as mapping because all of the information generated by analysis of the MCCE signals is combined in a single computer display of a three-dimensional figure that has the shape of the heart chamber of interest and employs additional image qualities such as color which convey the sequence of electrical activity (activation map) or possibly other qualities of the electrical activity (e.g., voltage map). These images are similar in style to weather maps common today in weather-forecasting. Such a cardiac map becomes a focus of attention for the EP doctor as he directs the motion of catheters in the heart to new positions, and an algorithm which processes the MCCE signals produces measurements from the electrodes in new positions. As this process continues, the map is updated with new colored points to represent additional information about the electrical activity of the heart.

During a mapping procedure, the timing relationships of muscle depolarizations typically must be determined for hundreds of locations around a heart chamber which may be experiencing an abnormal rhythm. The locations are often examined, one at a time, by moving an exploring cardiac-catheter electrode (mapping-channel electrode) from location to location, acquiring perhaps only a few seconds of signal data at each location. To compare timing relationships, a different electrode (reference-channel electrode) remains stationary (at a single location) and continuously acquires a reference signal of the rhythm.

The collection of timing relationships and anatomical locations constitutes an activation map (LAT map). As described above, a relatively large number of individual LAT values are used to generate a useful LAT map. Many different locations may serve adequately as alternative reference locations, but it has been critical in the present state-of-the-art that whatever location is used as the reference, one activation map is committed for the entire duration to that reference location only.

U.S. Pat. No. 8,812,091 (Brodnick), titled "Multi-channel Cardiac Measurements" and filed on Jun. 20, 2013, discloses several aspects of improved methods for determining LAT. (Such patent and the invention of the present application are commonly-owned, and Donald Brodnick is also an inventor of the present invention.) The Brodnick patent discloses LAT-determination methods which include replacement of cardiac channels when the quality of such channel signals falls below a standard measure of channel-signal quality. Major portions of the disclosure of the Brodnick patent is included herein since it provides excellent background information for the improved LAT-determination methods disclosed herein.

Occasionally a reference electrode is bumped or becomes disconnected. In these cases, additional data cannot be collected to extend the map (add more LAT values to the map) because the timing relationships are no longer comparable (based on the same reference-channel signal). The EP doctor either makes his or her interpretation of the map based on an incomplete map or establishes a new reference and begins to create a new map, having lost the time and effort which to this point in the procedure had been expended. At a few seconds of signal acquisition per location, a few seconds of catheter motion between locations, and hundreds of locations, the amount of time and effort wasted if a map must be restarted can be very significant. Furthermore, extending the total procedure time adds more risk of complications for the patient.

Because the heart is constantly contracting and other catheters are continually being repositioned, a procedure may last for several hours, during which time the patient even may need to be moved. Occasionally a reference electrode either makes poor contact or may shift position, in which case the constant timing relationship is disrupted (timing stability is lost) and additional locations cannot be studied in relationship to the accumulated data. As described above, the resulting incomplete activation map may be worthless, requiring a new map, extending the procedure and adding cost and risk to the patient.

Thus there is a need for an automatic method of determining local activation time (LAT) from multi-channel cardiac electrogram signals which avoids substantial loss of LAT values in spite of losses of timing stability in reference channels during a local activation time mapping procedure.

The generation of position information and its combination with cardiac timing information is outside the scope of the present invention. The focus of the present invention is the processing of MCCE signals to measure time relationships within the signals, the two most important of which are cycle length (CL) and local activation time (LAT).

Currently-available MCCE-processing algorithms are simplistic and often provide inaccurate measurements which cause the activation map and many other cardiac parameter values to be misleading. A misleading map may either (1) compel the EP doctor to continue mapping new points until apparent inconsistencies of the map are corrected by a preponderance of new, more-accurately measured map points or (2) convince the EP doctor to apply a therapy to a muscle region which actually makes little or no progress in the termination of an arrhythmia, again prolonging the procedure while more points are mapped in an attempt to locate new regions where therapy may be effective.

Currently, computer systems which assist EP doctors in the mapping process have manual overrides to allow a technician, or sometimes the EP doctor himself, to correct the measurements made automatically by the system. This requires a person to observe a computer display presentation called the "Annotation Window" which shows a short length of the patient's heart rhythm, perhaps 3-5 heartbeats as recorded in 3-8 channels (signals from MCCE electrodes).

The channels of the annotation window are of several types. There is one channel, identified as a reference channel, the electrode of which ideally remains in a fixed position during the entire map-generating procedure, and there is at least one other intracardiac channel (the mapping channel) which senses the electrical signal at a catheter tip, the precise three-dimensional position of which is determined by other means. The electrical activity in the mapping channel is compared to the activity in the reference channel to determine the local activation time (LAT) which is used to color the map at that precise three-dimensional position.

Intracardiac channels may be of either the bipolar or unipolar recording types, and the inventive measurement method disclosed herein can be applied to both types of signals. Also, since it is possible during arrhythmias for some chambers of the heart to be beating in a rhythm different from other chambers of the heart, the annotation window often contains additional channels to aid in the interpretation of the data presented.

OBJECTS OF THE INVENTION

It is an object of this invention, in the field of electrophysiology, to provide an automatic method for accurate measurement of several parameters which characterize MCCE signals.

Another object of this invention is to provide an automatic method for such measurements which operates rapidly enough to not hinder an electrophysiologist performing procedures which utilize such a method.

Another object of this invention is to provide an automatic method for rapid and reliable measurement of cardiac parameters to reduce the length of time certain cardiac procedures require and also reduce the X-ray exposure times for the patients.

Another object of this invention is to provide an automatic method for rapid and reliable measurement of local activation times which are provided for the rapid generation of local activation time maps, determining the precise phase relationship between a reference channel and a mapping channel.

Still another object of this invention is to provide an automatic method for cardiac parameter measurement which can be used in real-time during certain interventional cardiac procedures.

Another object of this invention is to provide an automatic method for rapid and reliable activation mapping which can continue providing LAT measurement when a reference signal degrades in timing stability such that it is no longer useable as a reference signal.

Another object of the invention is to provide an automatic method for measuring cardiac parameters which is largely insensitive to the amplitude of the MCCE signals and almost entirely dependent on the timing information contained in such signals.

Another object of this invention is to provide an automatic method for measurement of local activation times which avoids the loss of LAT values that have been determined prior to a loss of timing stability of the reference-channel signal used to determine such LAT values.

Yet another object of the present invention is to provide an automatic method for generating a single map throughout an LAT mapping procedure even when all of a plurality of reference-channel signals fail intermittently at different times, as long as at least one reference channel is functioning properly at any time during the mapping procedure.

And yet another object of the inventive method is to provide reliable and accurate automatic determination of cardiac-channel timing stability and signal quality.

These and other objects of the invention will be apparent from the following descriptions and from the drawings.

SUMMARY OF THE INVENTION

The term "digitized signal" as used herein refers to a stream of digital numeric values at discrete points in time. For example, an analog voltage signal of an MCCE channel is digitized every millisecond (msec) using an analog-to-digital (A/D) converter to generate a series of sequential digital numeric values one millisecond apart. The examples presented herein use this sampling rate of 1,000 samples per second (sps), producing streams of digital values one millisecond apart. This sampling rate is not intended to be limiting; other sampling rates may be used.

The term "velocity" as used herein refers to a signal the values of which are generally proportional to the time-rate-of-change of another signal.

The term "velocity-dependent signal" as used herein refers to a set of possible signals which relate to the velocity of a channel signal, and in particular, retain certain properties of channel velocity. Channel signals are filtered to generate velocity-dependent signals which contain signal information which does not lose either the positive or negative activity in a channel signal. One such velocity-dependent signal is the absolute value of channel velocity; such a velocity-dependent signal is used in some embodiments of the inventive method to preserve the magnitude of the activity in a signal. Other possible velocity-dependent signals are even powers of velocity (squared, $4^{th}$ power, etc.) which retain both the positive and negative signal activity in a velocity signal; the relative magnitudes are not critical in the present invention as long as both positive and negative activity within the signals are not masked by the filtering. Numerous other possible filtering strategies may be used to generate velocity-dependent signals, such as comparison of positive portions of the velocity with respect to a positive threshold, and, similarly, comparison of negative portions of the velocity with respect to a negative threshold. With respect to their use in the present invention, all velocity-dependent signals as defined herein are fully equivalent to absolute-value velocity filtering in every relevant respect.

The term "two differenced sequential boxcar filters" as used herein refers to two boxcar filters which operate in tandem and then the difference between the two boxcar filter values is computed. Such a filtering operation is one embodiment by which a low-pass filter followed by a first-difference filter is applied. Two differenced sequential boxcar filters are illustrated in FIG. 3A and described in detail later in this document.

The term "normal median" as used herein refers to the numeric value determined from a set of numeric values, such numeric value (median) being computed according to the commonly-understood mathematical meaning of the term median. The normal median of a finite set of numeric values can be determined by arranging all the numeric values from lowest value to highest value and picking the middle value from the ordered set. If there is an even number of numeric values in the set, the normal median is defined to be the mean of the two middle values of the ordered set.

The term "set-member median" as used herein refers to the numeric value determined from a set of numeric values in a manner modified from the above-described method of median determination. In this modified determination, if there is an even number of numeric values in the set, the set-member median is either one of the two middle values in the ordered set such that the set-member median is always a member of the set of numeric values. As a practical matter, in almost all sets of real data, there is a very large number of data values near the median, and there is little if any difference between the two middle values.

The term "intracardiac channel" as used herein refers to a channel of a set of MCCE signals which is connected to an internal lead, i.e., connected to an internal-surface electrode such as is at the end or along the tip of a cardiac catheter. For example, such an electrode may be in a blood vessel or in a chamber of a heart.

The term "activation" as used herein refers to a time segment within an MCCE signal which represents the passage of a depolarization wavefront within muscle cells adjacent to an MCCE electrode. An activation may sometimes be referred to as an activity trigger. Note that the terms "activations" and "activation times" may herein be used interchangeably since each activation has an activation time associated with it.

The term "cycle length" as used herein refers to the time between neighboring activations in an MCCE signal, particularly in a reference-channel or mapping-channel signal.

As used herein, the terms "method" and "process" are sometimes used interchangeably, particularly in the description of the preferred embodiment as illustrated in the figures. The algorithms described as embodiments of the inventive automatic method of measuring parameters of multi-channel cardiac electrogram signals are presented as a series of method steps which together comprise processes.

As used herein, the terms "signal" and "channel" may be used interchangeably since the inventive automatic method described herein uses signal values in the channels of MCCE signals. For example, often as used herein, the term "channel" implies the addition of the word "signal" (to produce "channel signal") but for simplicity and textual flow, the word "channel" is used alone.

The term "timing stability" as used herein refers to the degree to which a timing parameter, such as LAT, changes from one value to the next value during a cardiac procedure, based on a standard for timing stability. For example, an LAT may be said to be stable if has not changed from its past value (or a composite of past values) by more than a predetermined percentage or by more than a multiple of its standard deviation. Measurement of a timing parameter may of course also be affected by noise in one or more of the MCCE signals such that a determination of such parameter is degraded beyond usefulness. Such an occurrence will also be seen as a loss of timing stability.

The term "substantial loss of LAT values is avoided" as used herein refers to largely preventing the loss of the time and effort invested by the EP doctor in capturing LAT values and not narrowly to whether or not specific numerical values for LAT are retained. Avoiding substantial loss of LAT values may mean (a) that specific LAT values are used in an unchanged form, (b) that specific LAT values are corrected in order to be useful, and/or (c) that specific LAT values are replaced by other LAT values determined from already-existing cardiac electrogram signals. In all of these situations, the LAT values, whether in changed or unchanged form, are still available to be used. Changed LAT values are herein referred to as having been transformed.

The term "base reference channel" as used herein refers to the reference channel used in an LAT computation. LAT is computed using a mapping channel and a reference channel, and the reference channel is sometimes referred to herein as the base reference channel.

The term "signal characteristic" as used herein refers to a metric of a signal by which differences between signals may be distinguished.

The term "center-of-power frequency" as used herein refers to the first moment of power computed from a signal frequency spectrum.

The term "frequency-selective aggregate magnitude" as used herein refers to a value formed by combining multiple Haar transformation coefficients having differences based on the same time scale into a single value.

The present invention is an automatic method of determining local activation time (LAT) from at least three multi-channel cardiac electrogram signals which include a mapping channel and a plurality of reference channels. The method comprises: (a) storing the cardiac channel signals; (b) using the mapping-channel signal and a first reference-channel signal to compute LAT values at a plurality of mapping-channel locations; (c) monitoring the timing stability of the first reference-channel signal; and if the timing stability of the monitored signal falls below a stability standard, using a second reference-channel signal to determine LAT values and avoid substantial loss of LAT values in spite of loss of timing stability.

Some preferred embodiments of the inventive automatic LAT-determining method include computing one or more timing offsets using pairs of the plurality of reference-channel signals, a timing offset being $LAT_K(J)$, the local activation time of a reference channel J based on a reference channel K and used to transform an LAT value based on reference channel J to an LAT value based on reference channel K.

In certain preferred embodiments, using the second reference-channel signal to determine LAT values includes transforming future LAT values such that they are based on the first reference channel. In some of these embodiments, $LAT_2(M)$ is a future LAT value of mapping channel M based on the second reference channel, and future transformed values $LAT_1(M)$ of mapping channel M based on the first reference channel are equal to a timing offset $LAT_1(2)$ plus $LAT_2(M)$.

Some other preferred embodiments using the signal of a second reference channel to determine LAT values by transforming LAT values include transforming past LAT values such that they are based on the second reference channel. In some of these embodiments, $LAT_1(M)$ is a past LAT value of mapping channel M based on the first reference channel, and past transformed values $LAT_2(M)$ of mapping channel M based on the second reference channel are equal to a timing offset $LAT_2(1)$ plus $LAT_1(M)$.

In some highly-preferred embodiments, the one or more timing offsets are computed at a plurality of times, and the value of each timing offset is replaced with its average over the plurality of times. In some of these embodiments, the average is computed over a predetermined number of times.

In highly-preferred embodiments of the inventive automatic LAT-determining method, monitoring the timing stability of the first reference-channel signal includes monitoring multiple timing offsets $LAT_1(X)$ where X represents the channels with which timing offsets with the first reference channel are computed. Some of these embodiments further include computing a signal characteristic for the plurality of reference channels and determining therefrom which one or more channels among these reference channels has/have not lost timing stability. Some embodiments also include selecting the second reference-channel signal from channels which have not lost timing stability, and in some of these embodiments, selecting the second reference-channel signal from channels which have not lost timing stability includes computing signal quality.

In some preferred embodiments, computing a signal characteristic includes computing the frequency content of the signal. In some of these embodiments, computing the frequency content of the signal includes computing a fast Fourier transform (FFT) for a predetermined time period of the signal. In some such embodiments, the computed signal characteristic is the first moment of the signal power determined from the computed fast Fourier transform.

In some highly-preferred embodiments, computing frequency content of a signal includes segmenting the signal into a plurality of time-overlapping segment signals. In some of these embodiments, weightings are applied to each of the segment signals. In some such embodiments, computing the fast Fourier transform of the signal includes (a) computing a signal-segment fast Fourier transform for each segment signal and (b) averaging each such signal-segment fast Fourier transform to form the fast Fourier transform of the signal. In some of these embodiments, the computed signal characteristic is the first moment of the signal power determined from the fast Fourier transform of the signal.

In other embodiments, computing the frequency content of the signal includes computing a Haar transform for a predetermined time period of the signal, and in some such embodiments, the computed signal characteristic is the first moment of the signal power determined from the computed Haar transform. In some of these embodiments, the signal is segmented into a plurality of substantially-sequential segment signals. In some embodiments, computing the Haar transform of the signal includes (a) computing Haar transform coefficients for each segment signal, (b) computing absolute values of the coefficients, (c) computing a set of frequency-selective aggregate magnitudes for each segment signal by summing signal-segment Haar transform coefficients having like time scales, and (d) averaging the sets of frequency-selective aggregate magnitudes to form a single set of frequency-selective aggregate magnitudes for the signal. In some of these embodiments, the computed signal characteristic is the first moment of the signal power determined from the frequency-selective aggregate magnitudes.

In certain other embodiments of the inventive automatic LAT-determining method, the computed signal characteristic is the fraction of time within a predetermined time period of the signal at which the absolute value of signal velocity is above a predetermined threshold.

In certain other embodiments, the computed signal characteristic is the maximum signal amplitude minus the minimum signal amplitude within a predetermined time period of the signal.

BRIEF DESCRIPTION OF THE DRAWINGS

FIG. 3A is an illustration of the operation of the filtering which occurs by applying two differenced sequential boxcar filters to a digitized signal.

FIG. 3B depicts the absolute value of the output signal of the filtering operation illustrated in FIG. 3A.

FIG. 4B illustrates the process of identifying activations in an example absolute-value velocity channel signal as processed by the process of FIG. 4A.

FIG. 7B is a table which illustrates the process by which a specific mapping-channel activation is selected for the determination of LAT for the example of FIG. 7A.

FIG. 7C-1 through FIG. 7C-4 are a set of plots illustrating in detail a selected mapping-channel activation and its corresponding portion of the reference-channel signal which, as illustrated in FIGS. 7A and 7B, are used to determine LAT for a single mapping point.

FIG. 7D is a table illustrating an embodiment of a method to assess measurement confidence in the method of FIG. 1, using the examples of FIG. 7A through FIG. 7C-4. FIG. 7D also illustrates a second alternative method embodiment to determine an LAT value for a single mapping point.

FIG. 14 is a table showing exemplary values for timing offsets computed in one step within the embodiment of the inventive method for determining local activation time shown in FIG. 13. The table of FIG. 14 also presents an example determination of whether or not a loss of timing stability has occurred in the example of the method embodiment of FIG. 13.

FIGS. 15H-15L are five plots illustrating the segment spectra computed with a fast Fourier transform of the five weighted segment signals of FIGS. 15C-15G.

FIG. 15M is a plot of the average signal spectrum of the five segment spectra of FIGS. 15H-15L and from which an epoch center-of-power frequency is computed.

FIG. 15N is a table illustrating a method embodiment of the determination of which particular channel(s) have caused the loss of timing stability which was determined to have occurred in the example of FIG. 14. The signal characteristic used in this example embodiment is the FFT-based signal characteristic computation alternative of FIG. 15.

FIG. 16A is a plot illustrating the application of an absolute-value velocity filter to the exemplary six-second epoch cardiac channel electrogram signal of FIG. 15A.

FIG. 16B is a plot illustrating the computation of an activity duration signal characteristic for the absolute-value velocity epoch signal of FIG. 16A.

FIG. 18G is a table detailing the computation of a Haar transformation of a cardiac electrogram signal consisting of 2,048 signal values and resulting in 2,048 Haar transformation coefficients $H_i$.

FIG. 18H is a table detailing the computation of a set of eleven frequency-selective aggregate magnitudes $A_i$ from the 2,048 Haar transformation coefficients $H_i$ of FIG. 20G.

DETAILED DESCRIPTION OF PREFERRED EMBODIMENTS

Figure 1:
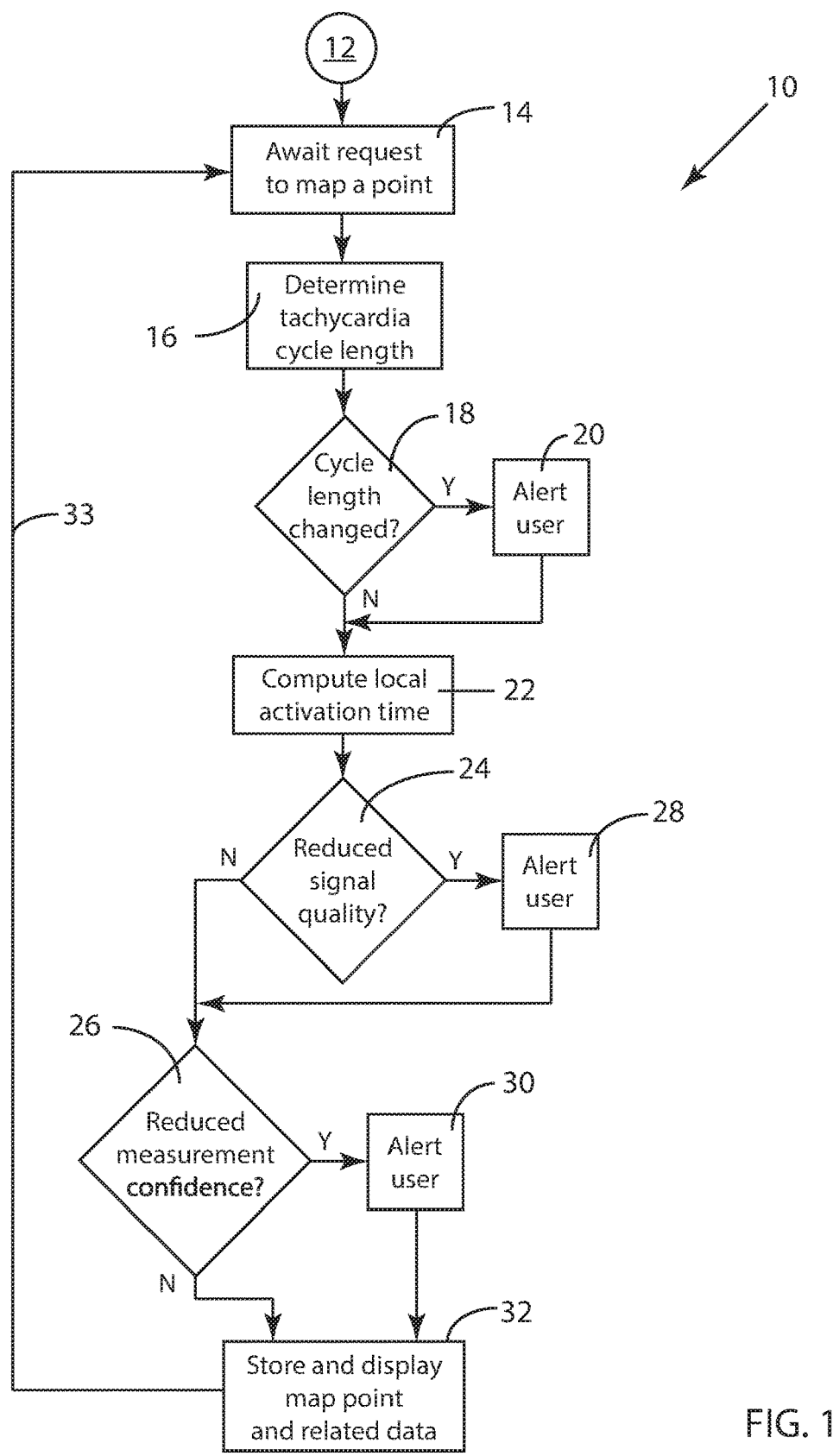
FIG. 1 is a schematic block diagram of a method for measuring parameters of MCCE signals, including intracardiac cycle lengths and local activation times and estimates of signal and measurement quality. The steps of the method as illustrated in the block diagram of FIG. 1 are further detailed in several other schematic block diagrams.

FIG. 1 illustrates one embodiment of a method for measuring parameters of multi-channel ECG signals. FIG. 1 is a high-level schematic block diagram of a method which measures intracardiac cycle lengths and local activation times on a near-real-time basis as part of a system to generate maps (e.g., computer displayed 3D presentations of the distribution of voltages and activation times across cardiac structures) and provides feedback regarding signal quality and measurement confidence.

Several other figures in this document relate to the method of FIG. 1, and the steps presented in the schematic block diagrams of these other figures are nested within the high-level schematic block diagram of FIG. 1, as will be described below. In addition, the method also includes initial channel selection steps which occur prior to the steps of FIG. 1. These are illustrated and described later in this document, in FIGS. 8 through 9B.

Referring to FIG. 1, an embodiment 10 of the method includes a flow loop of method steps which is initiated by a request 12 to map a point, and each time a mapping-point request 12 is generated, the method proceeds through the steps shown in FIG. 1. The flow chart element labeled with reference number 14 indicates that the flow loop waits to receive request 12. During a procedure in which the method is used, an electrophysiologist (EP doctor) is maneuvering an electrode-tipped catheter (mapping catheter) through and around the chambers, arteries and veins of a patient's heart. The electrode on this maneuvered catheter provides the mapping-channel signal. When the EP doctor determines that the maneuvered catheter electrode is in a desired position, the EP doctor activates a signal as request 12 to map a point. A plurality of map points constitute the map.

Generating the map during this procedure involves time measurements made between the MCCE signals of the mapping electrode and a reference electrode. (As used herein, electrodes are positioned to provide signals to channels. Thus, for example, the mapping electrode provides the signal for the mapping channel.) The reference electrode is positioned before mapping begins in a location that is expected to remain constant during the mapping process and that will generate stable and repetitive electrical signals.

Each electrode develops an electrical signal when muscle cells in contact with the electrode change their cell membrane potentials. These electric potentials change as the cells mechanically contract. Nerve cells, which do not contract, also can be in contact with electrodes and produce electrical signals.

The map being generated represents a particular heart rhythm being studied, such as tachycardia. The reference-channel and mapping-channel signals are both cyclical and have substantially the same cycle length (CL). The reference-channel signal represents a zero-phase or index moment of the particular cardiac cycle, and the local activation time (LAT) measurements (time difference between mapping and reference-channel signals) indicate the sequence of muscle and nerve cell activation of various points (map points) in the cardiac structure. This time sequence and its physical course around the anatomy of the heart are the information the EP doctor needs to determine how to apply therapy. The term "local" refers to the fact that the measurement applies to the heart cells in contact with the electrode and to signals with respect to a reference-channel signal, and this information is translated to a position on a three-dimensional (3D) image of the heart chamber.

Activation time is measured relative to one or more activations at the reference electrode and may be positive or negative. A local activation time which is negative by more than a half of one cycle length may also be recognized as being positive at a corresponding time less than a half of one cycle length. Local activation times may be defined as being relative to the nearest activation in the reference channel.

Positioning of the mapping catheter is guided at times by fluoroscopic imaging. At a position of interest, the EP doctor generates request 12 to trigger the system to make measurements from the MCCE signals available from the maneuvered catheter and other more stationary catheters and body surface electrodes. These measurements at mapping points are represented graphically, usually by color, on a 3D image of the heart chamber of interest. These points may be requested at irregular intervals of several seconds to perhaps minutes, depending on when the EP doctor maneuvers the mapping catheter to a point at which measurements should be taken.

When request 12 is received, measurements are made using an "epoch" of the most recent 6 seconds of MCCE signals. In embodiment 10, the 6-second length of this epoch should not be taken as limiting. The epoch is a preset time window of MCCE signals, and its 6-second length is chosen here in embodiment 10 such that selected signals during the preset time window contain a suitable number of electrical events to permit the analysis to be performed. During such mapping procedure, at least one mapping channel and at least one reference channel are used. At some points within embodiment 10, as will be described later in this document, the epoch is divided into three equal periods of time, and six seconds is chosen here since a 2-second period will almost always contain at least one heartbeat (or cell activation) for all heart rates above 30 beats per minute.

As the mapping catheter is moved, it is important that its electrode be in place at the selected location for a period of time (dwell time) long enough to obtain a suitable signal. In embodiment 10, such dwell time is about 2 seconds. Thus, when request 12 is received, the epoch consists of 6 seconds of data on other channels being used and 2 seconds of data on the mapping channel. (The 6 seconds of data may consist of the immediate past 4 seconds of the data plus 2 seconds of data generated after request 12 occurs. The 6 seconds of data in an epoch may also be the 6 seconds of data immediately preceding the request 12, since it may be that the mapping catheter has already been in a stable position for the 2 seconds prior to the triggering of request 12. Other possible strategies for acquiring the epochs of data are also possible.)

In the high-level schematic block diagram of FIG. 1, after request 12 is received, ending the wait in method step 14, a determination 16 of the intracardiac cycle length in the reference channel is performed. (Method step 16 is shown in FIG. 1 as determining tachycardia cycle length since the method is intended primarily for monitoring cardiac parameters in the treatment of patients in tachycardia. The use of the term "tachycardia" is not intended to be limiting. The method is applicable to measurement of all types of cardiac arrhythmias as well as normal heart rhythms.) Details of intracardiac cycle length determination 16 are detailed in the schematic block diagrams and example signals of FIGS. 2 through 5, all of which will be described later in this document.

Decision step 18 follows determination 16 such that the cycle length determined in step 16 is compared to a cycle-length-change criterion in decision step 18, and if the cycle length has not exceeded the cycle-length-change criterion, the method proceeds. If, however, the cycle-length-change criterion is exceeded, the EP doctor is alerted in method step 20 in order that steps may be taken by the EP doctor during the mapping procedure to evaluate the impact of such a change.

A cycle-length-change criterion applied in method step 18 may be based on an absolute time difference in cycle length from a previous cycle length or on the average of a plurality of previous cycle lengths. Or it may be based on a percentage change from such quantities. One useful previous cycle length is the initial or starting cycle length of the reference channel, established at the beginning of the mapping procedure.

A local activation time map is related to a particular rhythm so that if there is too great a change in cycle length, the EP doctor may choose to start a new map, or in fact may determine that mapping is no longer appropriate at such time. A value for the percentage change which triggers an alert in method step 20 may be that the current reference-channel cycle length (determined in method step 16) is found to differ from the starting cycle length by more than 10%. Such value is not intended to be limiting; other values may be found to provide adequate warning to the EP doctor.

Embodiment 10 of the method then proceeds to a computation 22 of the local activation time (LAT) associated with the map point being analyzed. Details of local activation time computation 22 are detailed in the schematic block diagram of FIGS. 6A-6C which will be described later in this document, and examples of such determination are illustrated in FIGS. 7A through 7D.

Embodiment 10 of the method for measuring parameters of MCCE signals includes steps for evaluation 24 of signal quality and evaluation 26 of measurement confidence, both of which are applied within embodiment 10 to monitor the measurement process. In each case, that is, reduced signal quality as determined in step 24 and reduced measurement confidence in step 26, the EP doctor is alerted (user alerts 28 and 30, respectively) that such conditions have been detected. One embodiment of a method to measure signal quality in method step 24 is included in the steps illustrated in FIG. 4A and will be discussed later in this document. One embodiment of a method to assess measurement confidence in method step 26 is illustrated in the example of FIG. 7D described later in this document.

As shown in FIG. 1, the method of embodiment 10 provides (in step 32) the map point and its related measurement data to a computer at least for display to the EP doctor during the procedure and for storage in memory for later analysis. The system then returns via loop path 33 to wait for the next mapping point request 12 at step 14.

Figure 2:
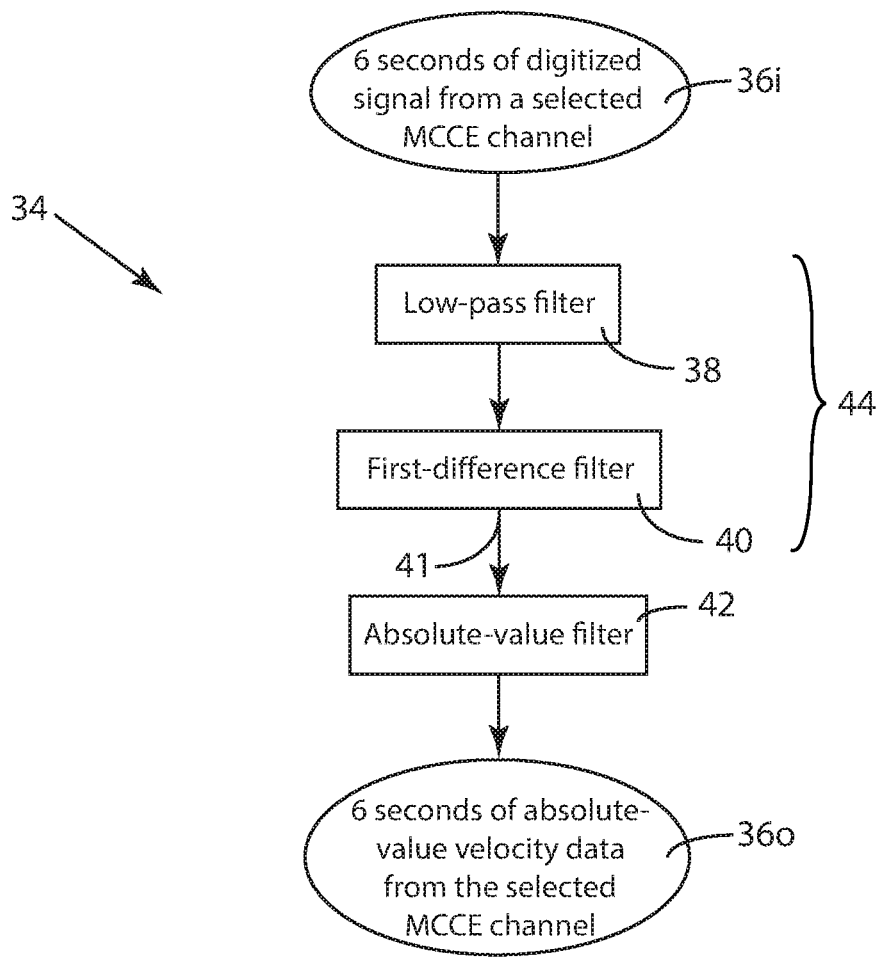
FIG. 2 is a schematic block diagram illustrating steps of a method to generate absolute-value velocity data of a selected digitized MCCE signal.

FIGS. 2, 3A and 3B illustrate an embodiment of a portion of the steps of the method further detailed in FIGS. 4A-9B. FIG. 2 is a schematic block diagram illustrating detailed steps within embodiment 10 by which a selected digitized MCCE channel signal 36i is filtered to generate a corresponding absolute-value velocity signal 36o. The steps of FIG. 2 are applied to various signals within method embodiment 10, as indicated later in the description below.

In FIG. 2, the combined steps, low-pass filter 38, first-difference filter 40, and absolute-value filter 42, are together shown as an absolute-value velocity filter 34. The first two steps of absolute-value velocity filter 34, low-pass filter 38 and first-difference filter 40, are together shown as a bandpass filter 44 which generates a filtered velocity signal 41 of an input signal.

As shown in FIG. 2, an input signal 36i is a 6-second preset time window (epoch) of digitized data from a selected MCCE signal. Low-pass filter 38 operates on input signal 36i followed by first-difference filter 40, and together these two filters generate a digital stream of data 41 which corresponds to the filtered velocity (first derivative) of input signal 36i with certain low and high frequencies filtered out. That is, filter 44 is a bandpass filter. Absolute-value filter 42 simply applies an absolute-value operation (rectification) to filtered velocity signal 41 from first-difference filter 40 to generate output signal 36o which is an absolute-value velocity signal of input signal 36i.

One embodiment of applying a combination 44 of low-pass filter 38 and first-difference filter 40 to a digitized signal is what is called herein "two differenced sequential boxcar filters," and such filtering embodiment is illustrated in FIG. 3A, in which an example digitized signal 46 is shown both graphically (46g) and numerically (46n). Seven pairs of "boxcars" 48b illustrate the sequential operation of boxcar filter 48.

Referring to FIG. 3A, each pair of boxcars 48b in boxcar filter 48 is four time samples in length, and two boxcars 48b are such that one follows the other immediately in time. (Only two of the 14 boxcars 48b are labeled.) The sum of the four time samples of digitized signal 46 in each boxcar 48b is calculated. Thus, for example, the left boxcar 48b of the uppermost (first in time) pair as shown holds the sum of the four time samples it subtends, and the right boxcar 48b of this pair holds the sum of the four time samples it subtends. These two sums are 7 and 12, respectively, and the difference between the right boxcar value and the left boxcar value is 12−7=5. This differenced value 5 is shown to the right of the uppermost boxcar 48b pair, and seven such values, indicated by reference number 50, are shown to the right of the seven example sequential boxcar 48b pairs. This output signal 50 is shown both numerically as 50n and graphically as 50g. Filter output signal 50 is shown for the seven time samples between the dotted lines labeled 52a and 52b. In the example of FIG. 3A, each boxcar 48b has a boxcar-width $w_B$ of four samples. The value of $w_B$ determines the frequency response of boxcar filter 48, or the amount of smoothing provided by boxcar filter 48. Larger values of $w_B$ produce a lower central frequency of boxcar filter 48 and therefore more smoothing of the signal on which it operates. Such relationships are well-known to people skilled in the art of digital filtering. Any specific value for $w_B$ used herein is not intended to be limiting. However, for the embodiments exemplified herein, it has been found that values of $w_B$ of around 4 are appropriate for use on intracardiac signals. For MCCE signals digitized every one millisecond and for sequential four-sample-long boxcar filters 48 ($w_B$=4) illustrated in FIGS. 3A and 3B, the resulting bandpass filter has a center frequency of 125 Hz.

The operation of the two differenced sequential boxcar filters 48 performs low-pass filtering and differentiation to input signal 46 such that filter output 50 is proportional to the velocity of bandpass-filtered digitized signal 46. No scaling has been applied in this example, but such lack of scaling is not intended to limit the meaning of the term two differenced sequential boxcar filters.

FIG. 3B, shown below and to the left of FIG. 3A, simply graphically illustrates the absolute value of output signal 50 as exampled in FIG. 3A. The absolute value of output signal 50 is processed by absolute-value filter 42 as shown in FIGS. 3A and 3B. This absolute-value velocity signal is output signal 36o of FIG. 2.

Some steps of the method as illustrated in embodiment 10 include the identification of activations or activity triggers within one or more channel signals of MCCE signals. Activations (activity triggers) are the electrical activity associated with the initiation of the depolarization of the heart muscle cells which occurs during a heartbeat, progressing like a wave through the various portions of the cardiac structure and causing the heart to pump.

Figure 4A:
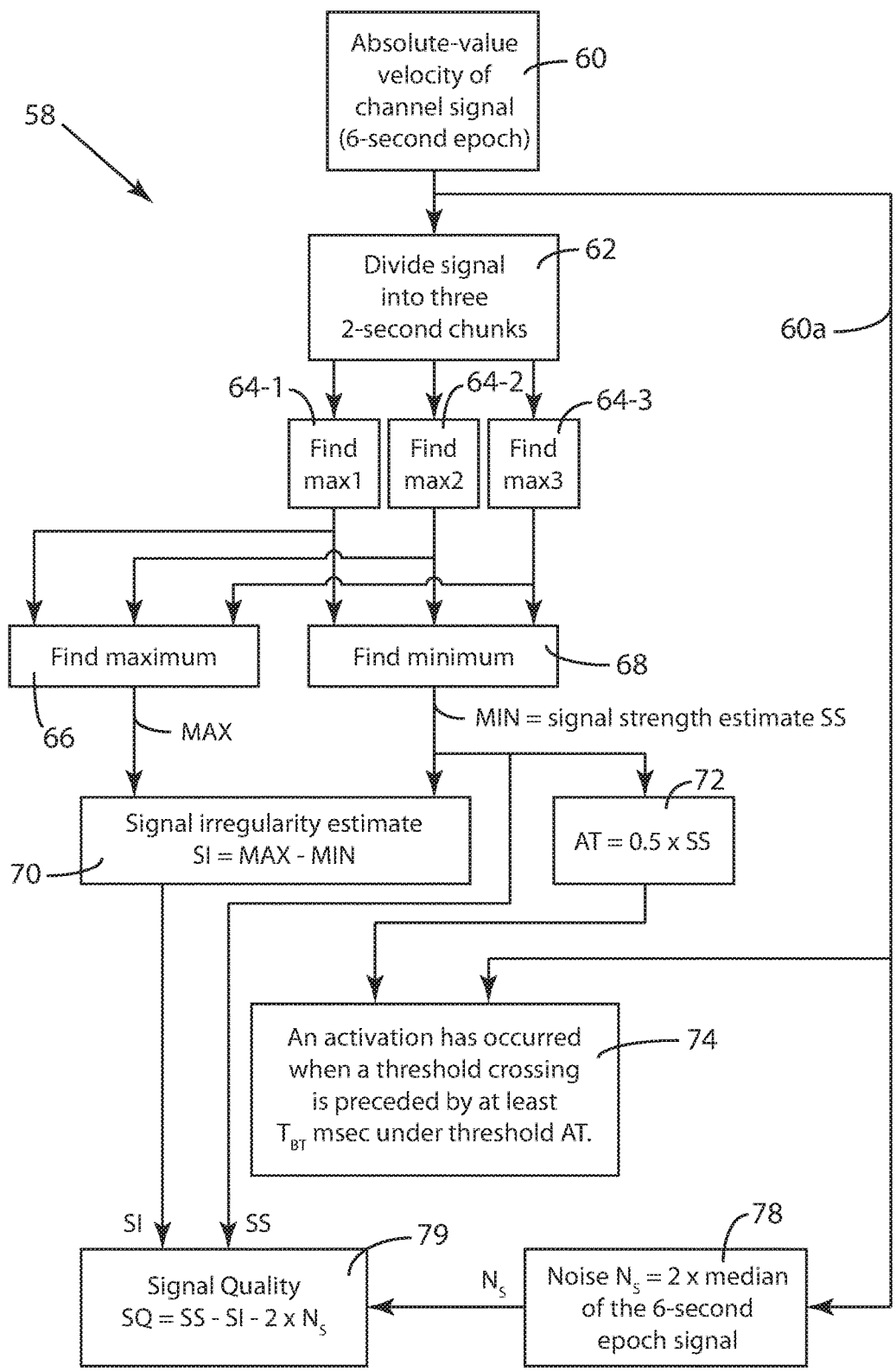
FIG. 4A is a schematic block diagram of the process of determining activations (activity triggers) in the absolute-value velocity signal from an MCCE channel. The steps of this process are applied to more than one channel signal in the method.

FIG. 4A is a schematic block diagram of a process 58 of determining activations (activity triggers) in an absolute-value velocity signal. The steps of process 58 may be applied to more than one channel signal.

In the embodiment of FIG. 4A, a signal 60 which is 6 seconds in duration (6-sec epoch) and is the absolute-value velocity of an MCCE channel signal, is divided into three 2-second "chunks" in method step 62. In method steps 64-1, 64-2 and 64-3, these three chunks are processed to find three signal maxima (max1, max2, and max3), one for each of the three signal chunks. These three values (max1, max2, and max3) are inputs to method step 66 which selects the maximum MAX among the three inputs and method step 68 which selects the minimum MIN among the three inputs. The values MAX and MIN are in turn inputs to method step 70 which determines an estimate SI for signal irregularity. In method step 70, signal irregularity SI is estimated as SI=MAX−MIN. A larger difference between the maximum (MAX) and minimum (MIN) values of the chunk maxima (max1, max2, and max3) indicates that there is more irregularity among the heartbeats within epoch 60 being processed. Signal irregularity SI is related to the variations in the "shape" of the activations in MCCE signals while other measurements described later in this document relate to variations in the time of activations.

The value MIN represents an estimate SS of signal strength. SS is multiplied by 0.5 (threshold factor) in method step 72 to determine a value for an activation threshold AT to be used in step 74 to determine the occurrence of activations within the MCCE signal being processed. The value (0.5) of the threshold factor applied in method step 72 of this embodiment is not intended to be limiting. Other values for the threshold factor maybe be applied in embodiments of the method.

Signal irregularity SI and signal strength SS are used in conjunction with an estimate of signal noise $N_S$ to provide an estimate of signal quality SQ in method step 79. In method step 78, signal 60 (provided by flow path 60a) is processed to compute its median over the entire six-second epoch, and such median is multiplied by 2 to produce estimate $N_S$ of signal noise. In method step 78, the calculation of the median of signal 60 may be done using a normal median or a set-member median. For such large data sets (e.g., 6 seconds at 1,000 sps), it has been found that using the set-member median is computationally convenient and highly suitable. In step 79, signal quality SQ is computed as SQ=SS−SI−2$N_S$.

The factor of 2 applied in method step 78 and the factor of 2 applied in method step 79 are both not intended to be limiting. Other values for such factors may be used. The size of the factor in step 78 is related to ensuring that the estimate of noise $N_S$ in signal 60 is a good representation of the noise level in signal 60. The size of the factor in step 79 is related to the relative weight given to noise estimate $N_S$ compared to those given to signal strength SS and signal irregularity SI in generating the estimate for signal quality SQ. The values of 2 for both of these factors have been found to provide good performance for estimating noise $N_S$ and signal quality SQ.

FIG. 4B illustrates method step 74 of FIG. 4A, the process of identifying activations in an example absolute-value velocity channel signal 60 as processed by the method steps of FIG. 4A. The signal of epoch 60 being processed is an input to method step 74 as indicated by the signal flow path 60a. A portion of example epoch 60 is illustrated in FIG. 4B. Activation threshold AT is shown as a dotted line AT parallel to the time axis and intersecting signal 60 at points 76. (Eleven signal crossings are shown; one such point is labeled 76a, one is labeled 76b, and one is labeled 76c).

As indicated in method step 74 of FIG. 4A, activations in epoch 60 being processed are indicated by identifying threshold crossings 76 before which signal 60 does not cross activation threshold AT for at least $T_{BT}$ milliseconds. The value of before-threshold time $T_{BT}$ chosen may vary according to the type of MCCE signal 60 being processed. For example, it has been found that $T_{BT}$=90 msec is an appropriate value when an intracardiac channel is being analyzed. This value for $T_{BT}$ is not intended to be limiting; the selection of a value for $T_{BT}$ is based on choosing a value by which a reliable differentiation between subsequent activations and among threshold crossings 76 within an individual activation can be achieved.

In the example of FIG. 4B, the activation labeled 75 shown includes six threshold crossings 76 as indicated by dotted circles occurring in rapid succession, the first being threshold crossing 76b and the last being threshold crossing 76c. A portion of a previous activation 77 within signal 60 is also shown in FIG. 4B. In activation 77, five threshold crossings 76 occur in rapid succession, the last of which is labeled 76a.

The time difference between threshold crossing 76a associated with activation 77 and threshold crossing 76b associated with activation 75 is about 185 msec as shown in FIG. 4B. In this example, 185 msec is longer than either of the example values for $T_{BT}$; thus threshold crossing 76b is determined to be the leading edge of activation 75, and the time at which threshold crossing 76b occurs is determined to be activation time $t_{ACT}$. In this example, threshold 76b is the only such threshold crossing illustrated in FIG. 4B.

Figure 5:
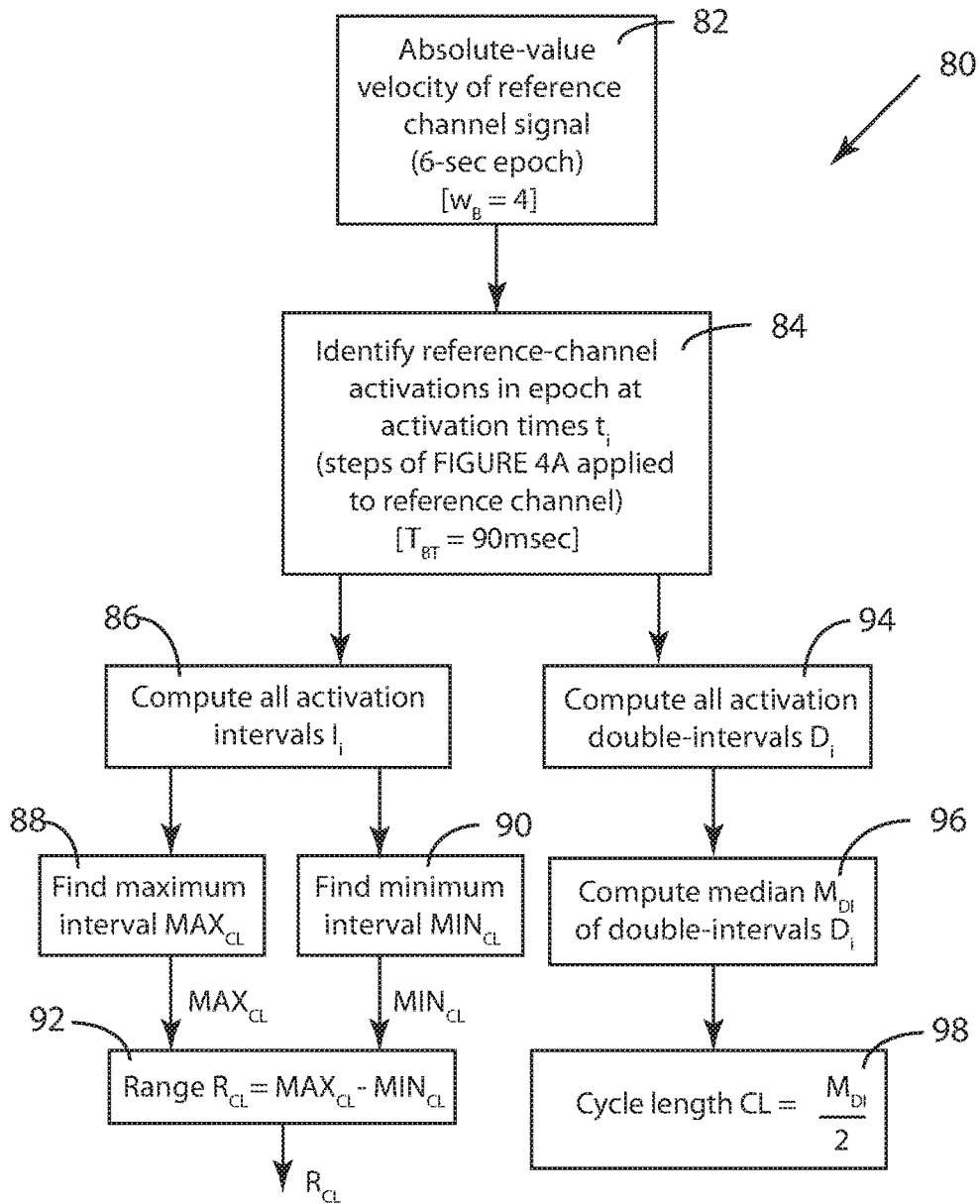
FIG. 5 is a schematic block diagram of the process of determining the reference-channel cycle length in the embodiment of FIG. 1.

FIG. 5 is a schematic block diagram of an embodiment 80 of a process of determining the reference-channel cycle length. The steps of embodiment 80 of FIG. 5 analyze an absolute-value velocity reference-channel signal epoch 82, again 6 seconds in duration. In method step 84, activations within epoch 82 are identified by applying steps 58 as illustrated in FIG. 4A. As indicated in method steps 82 and 84 of FIG. 5, the values for boxcar-width $w_B$ and before-threshold time $T_{BT}$ are $w_B$=4 and $T_{BT}$=90 msec.

Activations identified in method step 84 each have an activation time $t_i$, and for purposes of description, there are n such activation times. In method step 86, all activation intervals $I_i$ are computed. There are n−1 activation intervals $I_i$ computed as follows:

$$I_1 = t_2 - t_1$$

•

$$I_i = t_{i+1} - t_1$$

•

$$I_{n-1} = t_n - t_{n-1}$$

In method step 88, a maximum interval $MAX_{CL}$ of the n−1 activation intervals $I_i$ is computed, and in step 90, the minimum interval $MIN_{CL}$ of the n−1 activation intervals $I_i$ is computed. In method step 92, a range $R_{CL}$ for activation intervals $I_i$ is computed as the difference between $MAX_{CL}$ and $MIN_{CL}$.

The n activation times $t_i$ are also used in method step 94 to compute all double-intervals $D_i$ of reference-channel signal epoch 82. There are n−2 double-intervals $D_i$, and such double-intervals $D_i$ are computed as follows:

$$D_1 = t_3 - t_1$$

•

$$D_i = t_{i+2} - t_i$$

•

$$D_{n-2} = t_n - t_{n-2}$$

In method step 96, the normal median $M_{DI}$ of all double-intervals $D_i$ is computed, and in step 98, the estimate of reference-channel cycle length CL is computed as $$CL = M_{DI}/2$$

Thus, method steps of process 80 generate an estimate of reference-channel cycle length CL and provide an estimate of the range $R_{CL}$ over which CL varies. (For computational convenience in step 96, a set-member median calculation may be used in place of the normal median calculation.)

Occasionally a heart rhythm can be affected by a condition known as bigeminy in which the interval between beats alternates between slightly longer and shorter values. It is therefore desirable that the estimate of CL be the average of the two intervals, especially if the value of CL is used to extrapolate several cycles back in the past or into the future.

Figure 6A:
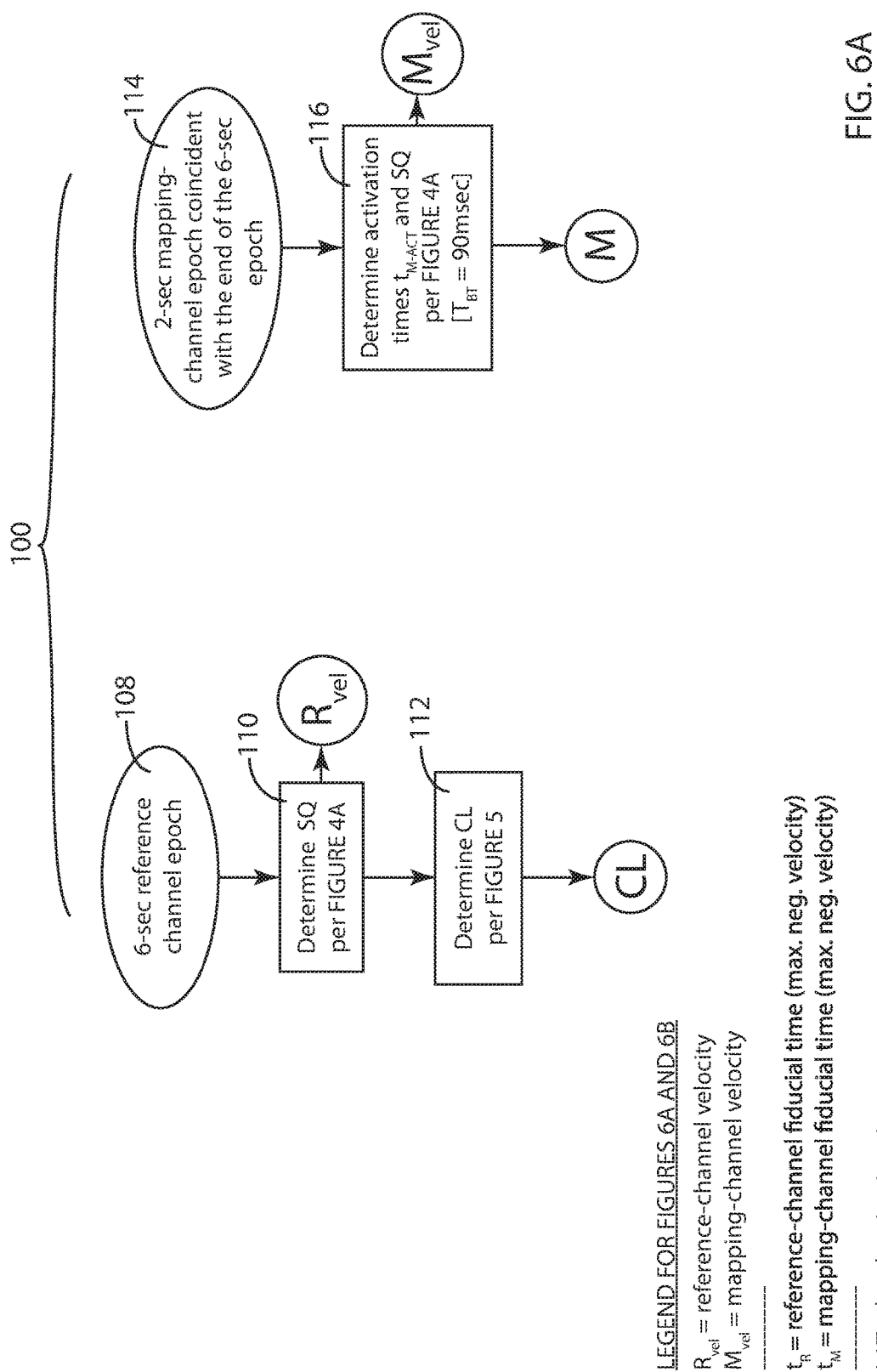
FIGS. 6A and 6B together are a schematic block diagram of the process of determining local activation time (LAT) for a single mapping point in the embodiment of FIG. 1.
Figure 6B:
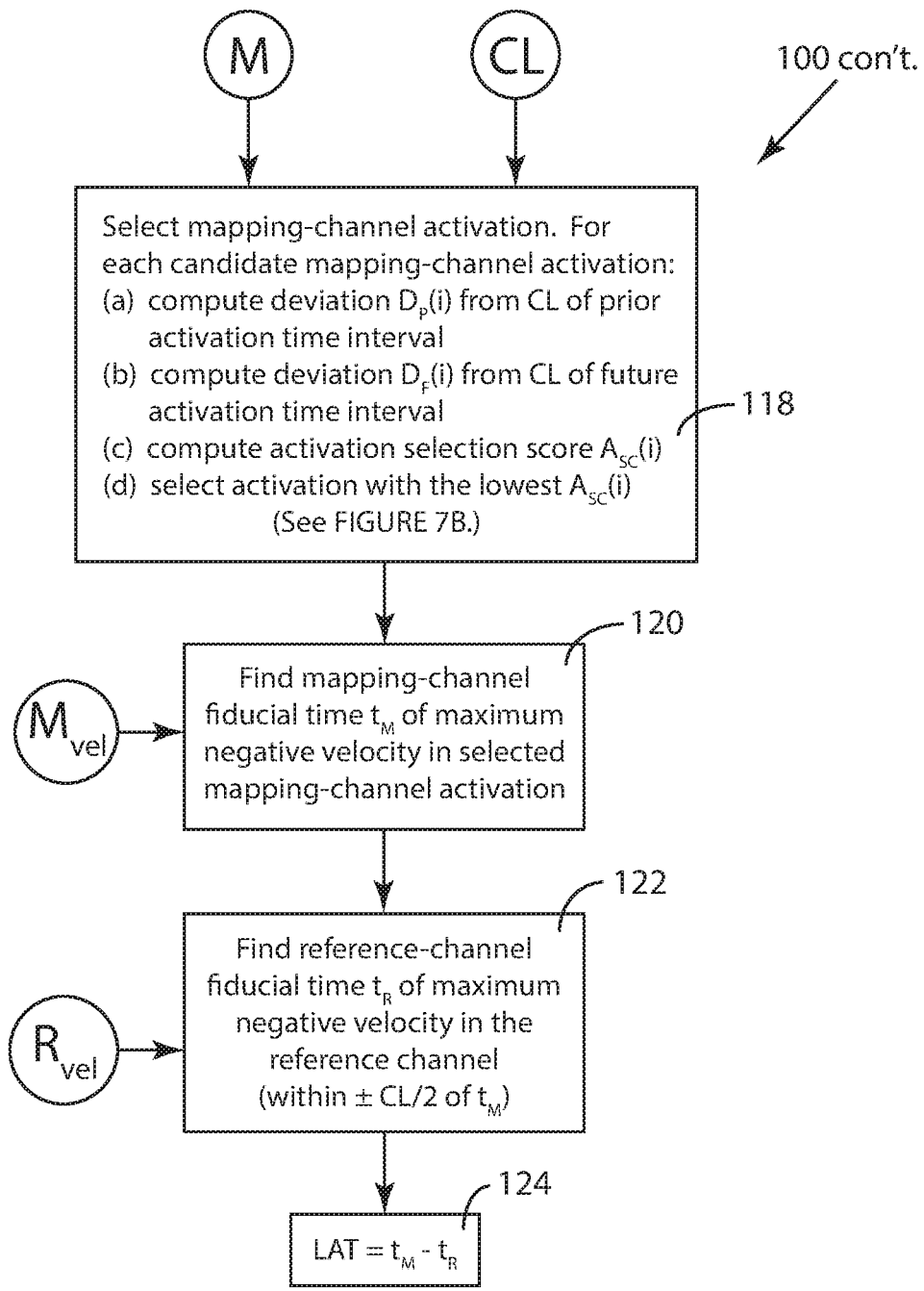

FIGS. 6A and 6B together are a schematic block diagram of an embodiment 100 of the process of determining local activation time (LAT) for a single mapping point in the method of measuring parameters of MCCE signals. FIG. 6A illustrates two MCCE signals on which computations are performed, as has been described above, in order to provide results which are used in the determination of LAT for a single mapping point. These are a reference-channel 6-second epoch 108 and a mapping-channel 2-second epoch 114 in which 2-second epoch 114 is coincident with the last 2 seconds of epoch 108. FIG. 6A includes a legend which defines the terminology used in FIGS. 6A and 6B.

In method step 110, reference-channel epoch 108 is processed with the steps of FIG. 4A and produces estimates of signal quality SQ and signal irregularity SI for epoch 108. Within the method steps of FIG. 4A, a velocity signal for the reference channel is computed, and it is used in the determination of LAT as indicated by the circle labeled $R_{vel}$ which is common with the same such circle in FIG. 6B. In method step 112, reference-channel cycle length CL is determined using the steps shown in FIG. 5, and reference-channel cycle length CL is used in the determination of LAT as indicated by the circle labeled CL which is common with the same such circle in FIG. 6B.

In method step 114, mapping-channel epoch 114 is processed with the steps of FIG. 4A and produces a set of mapping-channel activation times $t_{M-ACT}$ and estimates of signal quality SQ for epoch 114. (Epoch 114 is not sufficiently long to determine a useful estimate of signal irregularity SI. However, if a longer epoch length is used, SI may be estimated in method step 116.) Mapping-channel activation times $t_{M-ACT}$ are used in the determination of LAT as indicated by the circle labeled M which is common with the same such circle in FIG. 6B. Within the steps of FIG. 4A, a velocity signal for the mapping channel is computed, and it is used in the determination of LAT as indicated by the circle labeled $M_{vel}$ which is common with the same such circle in FIG. 6B.

FIG. 6B shows a continuation of the flow chart of embodiment 100. Inputs to the method steps of FIG. 6B have been computed in the method steps of FIG. 6A, and these inputs are illustrated by the circles labeled as described above. In method step 118, a mapping-channel activation for LAT determination is selected from among the activations and corresponding mapping-channel activation times $t_{M-ACT}$ determined in method step 116. The selection of such activation in step 118 includes the maximization of an activation selection score $A_{SC}$, a value for which is computed for each candidate activation among the set of mapping-channel activations. Details of method step 118 are described later in this document in the discussion of the example of FIGS. 7A and 7B.

After selecting the specific mapping-channel activation to be used to determine LAT in method step 118, a mapping-channel fiducial time $t_M$ is found in method step 120. In determining LAT, a more precise representation of event times is required than the threshold-crossing determination of activation detection in method step 74. In this document, "fiducial time" is the term used to indicate such a more precise determination of an event (activation) time. "Fiducial time" as used herein represents the instant within an MCCE signal at which a depolarization wavefront passes below the positive recording electrode in either a bipolar or unipolar MCCE signal.

As is well-known to those skilled in the field of electrophysiology, one good representation of fiducial time is the instant at which a signal exhibits its maximum negative velocity. Thus, one embodiment of method step 120 includes determining mapping-channel fiducial time $t_M$ as the time at which the maximum negative velocity occurs within the selected activation of the mapping channel. In a similar fashion, a reference-channel fiducial time $t_R$ is found in method step 122. Reference-channel fiducial time $t_R$ is the time at which the maximum negative velocity occurs within $\pm CL/2$ of mapping-channel fiducial time $t_M$. Alternatively, a user may choose to define the fiducial time $t_R$ to be the time of maximum negative velocity from $+\alpha$ to $-\beta$ of cycle time CL with the constraint that $\alpha+\beta=1$.

The use of the time of maximum negative velocity as the fiducial time is not intended to be limiting. Other indications of precise depolarization event times may be used in determining the fiducial times.

In method step 124, the local activation time LAT for a position at which the mapping-channel electrode is located within the heart is computed as $LAT = t_M - t_R$. Local activation time LAT is determined relative to the selected reference channel, and values of LAT at a plurality of locations within the region of the heart being mapped are determined during the process of building an LAT map. If the quality of the channel signals being processed degrades before mapping is complete such that mapping cannot be continued, a new map must be generated. Local activation times may be positive or negative times (occurring after or before the corresponding activation event in the reference channel).

Figure 6C:
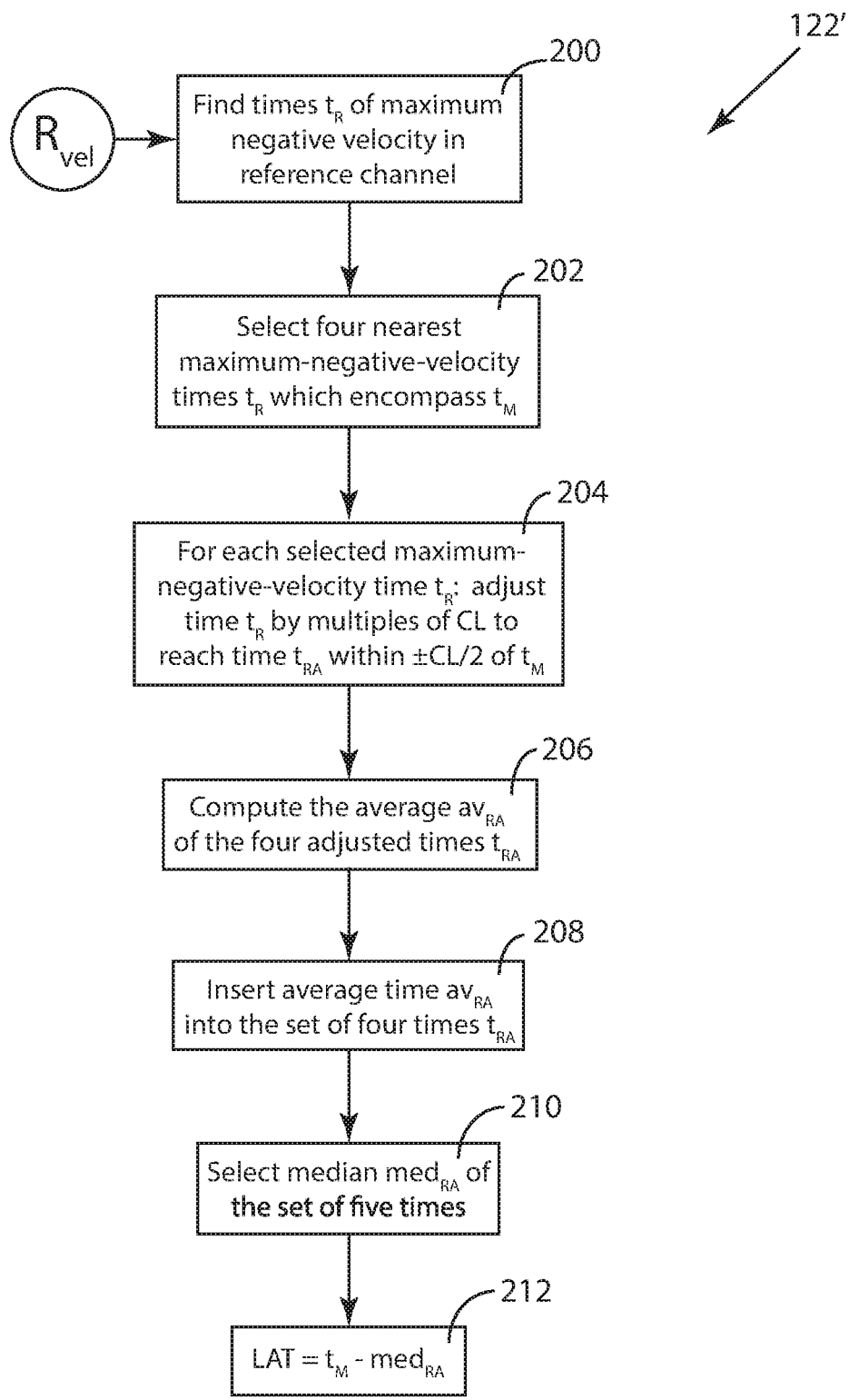
FIG. 6C is schematic block diagram of an alternative embodiment to determine LAT for a single mapping point, using additional fiducial times within a reference-channel signal.

FIG. 6C is a schematic block diagram of an alternative embodiment 122' of the process by which an LAT value is determined for a single mapping point. (Embodiment 122' of FIG. 6C is an alternative embodiment to method steps 122 and 124 of FIG. 6B.) FIG. 6C will be described later in this document, after the example of FIGS. 7A-7D is described.

Figure 7A:
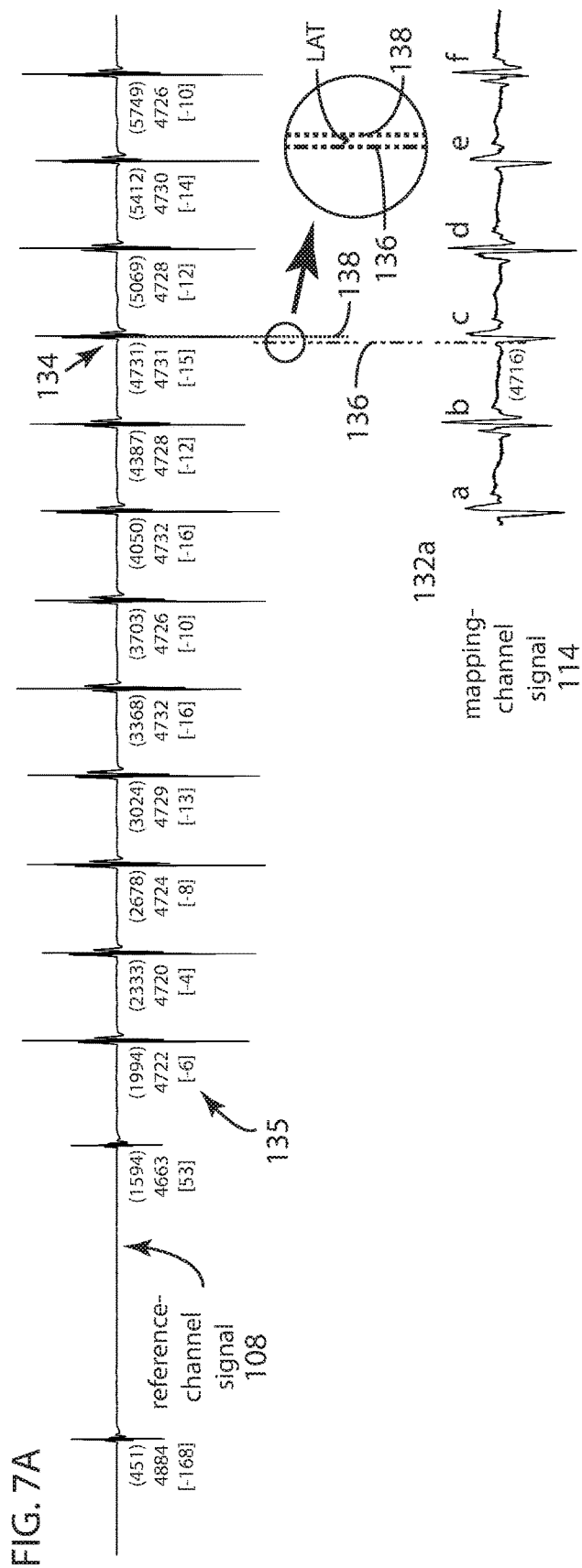
FIG. 7A is a set of MCCE signal plots illustrating an example of the process of determining LAT for a single mapping point as shown in FIGS. 6A and 6B.

FIG. 7A through FIG. 7D together illustrate in more detail the process of determining LAT for a single mapping-channel electrode location. FIG. 7A shows two exemplary MCCE signal plots. At the top of FIG. 7A is a 6-second epoch of an ECG reference-channel signal 108. Below and to the right of signal 108 is a 2-second epoch of an MCCE mapping-channel signal 114 which is time-coincident with the final 2 seconds of reference-channel signal 108. (Note that in FIG. 7A, the signal traces illustrated are the MCCE voltage signals, not absolute-value velocity signals created during signal processing represented in the steps 100 of FIG. 6A.)

As described above, method step 84 of FIG. 5 identifies activations within the reference channel, and within reference-channel signal 108 shown in FIG. 7A, activations were identified at times (in milliseconds) within the 6-second reference-channel epoch at: 1,993; 2,332; 2,677; 3,023; 3,359; 3,702; 4,049; 4,386; 4,730; 5,068; 5,411; and 5,748. In method step 98 of FIG. 5, the reference-channel cycle length CL was found to be 341 msec.

Four mapping-channel activation times 130 are shown in FIG. 7A; four mapping-channel activations were identified in method step 116. Note that in this example, the first and last activations in the 2-second epoch of mapping-channel signal 114 were not identified by the threshold-crossing activation detection process of method step 74 of FIG. 4A. (For description purposes, all six activations in mapping-channel signal 114 are labeled 132a through 132f in FIG. 7A even though only four such activations were detected. The number 132 is not repeated with the letters a-f for simplicity in the figure. Activations 132a and 132f were not detected.)

FIG. 7B presents a table detailing method steps 118 by which a specific mapping-channel activation is selected for the determination of LAT for the example of FIG. 7A. FIG. 7B includes a legend further defining the terms utilized in construction of and computations within the table for this example. The reference-channel cycle length CL of 341 msec is shown in FIG. 7B at the top of the table.

As mentioned above, local activation time (LAT) is measured by the time difference between a fiducial time $t_M$ in an activation in the mapping channel and its corresponding fiducial time $t_R$ in the reference channel. As part of this determination, an activation within the mapping-channel signal 114 must be selected for such computation, in method step 118 of FIG. 6B. This selection process includes: (a) for each mapping-channel activation i, determining the deviation $D_P(i)$ from CL of the time to the previous mapping-channel activation i−1; (b) for each mapping-channel activation i, determining the deviation $D_F(i)$ from CL of the time to the next (future) mapping-channel activation i+1; (c) computing an activation selection score $A_{SC}(i)$; and (d) selecting the activation with the lowest activation selection score $A_{SC}(i)$. The mathematical representations of these determinations are shown in the legend of FIG. 7B.

To generate a full map of local activation times, often a large number of individual points must be determined. This can be a time-consuming process. It is therefore desirable to determine each individual value of LAT as quickly as possible once a new position of the mapping-channel electrode being manipulated by the EP doctor is established. It has been found that about 2 seconds is often required to make a good determination. At typical intracardiac heart rates being measured, only a few activations occur in the mapping channel during a 2-second epoch period, so it is helpful to increase the number of candidate activations by adapting to situations where an activation is "missing" due to a failed activation detection or to a simple epoch-end timing situation. The method includes a beginning-of-data rule and an end-of-data rule to increase the number of candidate mapping-channel activations. These special rules are as follows:

Beginning-of-data rule: In some cases, the first detected activity may be very near the beginning of available data. If the expected previous activity to a detected activity would be located before the beginning of the mapping-channel epoch, then there is no evidence that detections failed and the value for deviation $D_P(i)$ from CL of the prior activation time interval for such a candidate activation is presumed to be 0. However, if the amount of time in the available data in the mapping-channel epoch is longer than the expected cycle length CL, then it is likely that an activation failed to be detected due to some kind of noise in the mapping-channel signal, an irregular signal, or an insufficiency in the detection algorithm. In this case, deviation $D_P(i)$ is set to $t_{M\text{-}ACT}(i)$−CL−4000, but not less than 0, where CL is the reference-channel cycle length. (The constant term 4,000 accounts for the fact that the 2-second mapping-channel epoch is coincident with the end of the 6-second reference-channel epoch as noted in element 114 in FIG. 6A.)

End-of-data rule: This rule is symmetrical to the beginning-of-data rule and is created to handle the same available-data constraint at the end of the data. Deviation $D_F(i)$ from CL of the future activation time interval for only the last candidate mapping-channel activation is set to 0 if the last detected activity is within one reference-channel cycle length CL of the end of data. However, there may be more time in the available mapping-channel epoch data than one CL after the last detected activation. In this case, it is very likely that some kind of noise in the mapping-channel signal, an irregular signal, or an insufficiency in the detection algorithm caused a failed activation detection. In this case, the value of deviation $D_F(i)$ is set to the length of available following data minus CL or $D_F(i)=t_{ME}-t_{M\text{-}ACT}(i)-CL+4000$, but not less than 0, where $t_{ME}$ is the mapping-channel epoch length and CL is the reference-channel cycle length. (Again, the constant term 4,000 accounts for the fact that the 2-second mapping-channel epoch is coincident with the end of the 6-second reference-channel epoch as noted in element 114 in FIG. 6A.) Two such situations are illustrated in the example of FIGS. 7A and 7B.

The mapping-channel activation which is selected is the activation for which activation selection score $A_{SC}(i)$ is a minimum. As shown in FIG. 7B, $$A_{SC}(i)=D_P(i)+D_F(i).$$

It is desirable that the selected mapping-channel activation have neighboring cycle lengths close to reference-channel cycle length CL. This mathematical construction of the activation selection score $A_{SC}(i)$ accomplishes this desired relationship.

The computations outlined above and represented in FIG. 7B were carried out for the four candidate mapping-channel activations 132b through 132e (having activation times labeled 130). The activations labeled 132a and 132f were not detected; activation 132a occurred too close to the beginning of epoch 114, and activation 132f was not large enough to trigger the threshold in activation detection step 74. Thus, as shown FIG. 7B, both the beginning-of-data rule and the end-of-data rule were applied in this example to determine values for activations 132b and 132e. In the row of data in the table for mapping-channel activation 132b, the value of $D_F=41$ (indicated by reference number 118b) was determined by application of the beginning-of-data rule, and in the row of data in the table for mapping-channel activation 132e, the value of $D_F=248$ (indicated by reference number 118e) was determined by application of the end-of-data rule.

Mapping-channel activation 132c is selected based on its minimum activation selection score $A_{SC}=24$ (indicated by reference number 118a) among the candidate mapping-channel activations.

FIGS. 7C-1 through 7C-4 are a set of plots illustrating in detail method steps 120, 122, and 124 in which LAT is computed based on selected mapping-channel activation 132c and a reference-channel activation 134. Reference-channel activation 134 is near in time to $t_M$. As indicated above, in this example, fiducial times $t_M$ and $t_R$ are the instants in the mapping-channel and reference-channel activations at which the maximum negative velocity occurs. FIG. 7C-1 illustrates an expanded signal of mapping-channel activation 132c, and FIG. 7C-3 illustrates an expanded signal of mapping-channel activation velocity 132c:v. Mapping-channel fiducial time $t_M$ is indicated by the dotted line labeled 136. The value of $t_M$ in this example is 4716 msec as indicated to the left of mapping-channel activation 132c in FIG. 7A.

Reference-channel activation 134 is the activation in reference-channel signal 108 which is located within within $\pm CL/2$ of $t_M$ along the time axis of reference-channel signal 108. FIG. 7C-2 illustrates an expanded signal of reference-channel activation 134, and FIG. 7C-4 illustrates an expanded signal of reference-channel activation velocity 134:v. Reference-channel fiducial time $t_R$, indicated by the dotted line labeled 138, is clearly located within $\pm 171$ msec ($\pm CL/2$) of $t_M$. (CL/2 is rounded up from 170.5 to 171 to ensure that extrapolated time falls within the appropriate interval.)

In this example, reference-channel activation 134 occurs after mapping-channel activation 132c, and the local activation time $LAT=t_M-t_R=-15$ msec. This value of LAT provides a single point in the generation of an LAT map. As mentioned above, an LAT map is based on a single reference channel with its electrode placed at the same point in the cardiac structure throughout the entire generation of the map. A plurality of LAT measurements is used to generate an LAT map, each such point being made available for display by the system.

In FIG. 6C, an alternative embodiment 122' for LAT determination is illustrated. Alternative embodiment 122' takes advantage of the fact that multiple fiducial times $t_R$ are available in reference-channel signal 108 to which mapping-channel fiducial time $t_M$ may be compared. In method step 200, the times $t_R$ of maximum negative velocity generated in method step 110 of FIG. 6A are identified in reference-channel signal 108. As described above, activations in the reference channel are detected using a threshold-crossing technique, and a simple numerical search method may be used to find the fiducial times $t_R$ of local relative negative-velocity maxima in signal 108. In method step 202, the four nearest values $t_R$ to mapping-channel fiducial time $t_M$ are selected from among the values of $t_R$, and in method step 204, each of these four times $t_R$ are adjusted by adding or subtracting multiples of reference-channel cycle length CL until each adjusted value $t_{RA}$ is within $\pm CL/2$ of $t_M$ so that $t_{RA}$ now represents its relative time position within one cycle length CL. In method step 206, these four values are averaged and this average $av_{RA}$ is included with the set of four values of $t_{RA}$ in method step 208, creating a set of five time values. In method step 210, the median $med_{RA}$ of this set is found and in method step 212, LAT is determined as $LAT=t_M-med_{RA}$.

Referring again to FIG. 7A, reference-channel signal 108 is shown with a set of numerical values 135 next to each activation in signal 108. (Only one such triplet 135 of values is labeled with reference number 135 to avoid clutter within FIG. 7A.) There are 14 such triplets 135 of values, and each triplet consists of (1) a fiducial time $t_R$ of the maximum negative velocity in signal 108 (the number in parentheses), (2) the adjusted time $t_{RA}$ by adding or subtracting multiples of cycle length CL to place $t_{RA}$ within $\pm CL/2$ of $t_M$, and (3) the time difference between $t_M$ and $t_{RA}$, also referred to as intermediate LAT values. This set of time values is also shown in the table of FIG. 7D.

Referring to FIG. 7D, rows A, B, and C correspond to the time value triplets described in the above paragraph. Row D is an ordered list of the intermediate LAT values in row C. Due to variations in measurement conditions or sources of variability, outlier values may be present at either end of this ordered list. To avoid such outliers (such as the two highest values in row D of 44 and 161), an interquartile set of values is selected in row E, dropping the lowest and highest 25% of values from the ordered list. This interquartile list may then be used to provide an estimate of a measurement confidence interval for method step 26 in FIG. 1. The range of this interval is indicated by the end values of row E which range from −15 to −10, or a ±2.5 msec LAT measurement confidence interval. Further, a measurement-confidence criterion for method step 26 in FIG. 1 may be as follows: if the width of the measurement confidence interval (in this example, 4) is greater than some percentage of cycle length CL, then alert the EP doctor in method step 30. This width percentage criterion may be about 5%, but this specific value is not intended to be limiting. An absolute width, say 15 msec, may also be used as the criteria; again such absolute width criterion value is not intended to be limiting.

Referring to FIG. 7D to illustrate the alternative method of LAT determination described in FIG. 6C, the four values of $t_R$ indicated by reference number 214 are the four nearest times $t_R$ which encompass mapping-channel fiducial time $t_M$, forming a set 214 of four values $t_R$ (in row A) as described in method step 202. The four values are adjusted as described above and form the set of four values $t_{RA}$ (in row B) described in method step 204. The average of these four values $t_{RA}$ is computed in method step 206 ($av_{RA}=4730.25$ msec), This value $av_{RA}$ is added to set 214 to form a set of five values as indicated in method step 208. The set of five values is now the set (4727, 4729, 4730.25, 4731, 4734). The median $med_{RA}$ of this set is 4730.25 as found in method step 210, and LAT is determined by $LAT=t_M-med_{RA}$, or $LAT=4716-4730.25=-14.25$ msec. One advantage of such an embodiment is that some additional computational precision occurs with the use of the averaging step.

The use of the four nearest times $t_R$ which encompass $t_M$ is not intended to be limiting. Other choices for the number of values $t_R$ used in the LAT determination may be employed.

Additionally, the steps described with respect to FIG. 7D also form a second alternative embodiment for LAT determination, potentially taking into account even more reference-channel fiducial times $t_R$ in the estimate of LAT. In this second alternative embodiment, the median value of the interquartile set of intermediate LAT values may be used as the LAT value for the current mapping point. As shown in FIG. 7D, the interquartile median value in row E is −12 msec, the LAT value for this second alternative method of LAT determination. Note that this value for LAT is more representative of the heart rhythm than the single-beat determination of −15 msec which appears best to represent only every other beat (bigeminy) in the rhythm. Again as above, other choices may be made for the number of values of $t_R$ used in the determination of LAT.

Signal quality SQ as determined in method step 79 of FIG. 4A is also applicable for use within method step 24 of FIG. 1 in which signal quality is monitored to provide alert 28 when signal quality SQ degrades. One criterion by which to assess signal quality in method step 79 of FIG. 1 is simply to determine if the two signal quality values (reference channel and mapping channel) are positive. The signal quality SQ determination for the mapping channel differs from that of the reference channel; it does not include a signal irregularity SI term (i.e., $SQ=SS-2N_S$ for the mapping channel) since the 2-second epoch of the mapping channel is too short to generate a meaningful value for signal irregularity SI. The decision of method step 79 is in the affirmative if either of the two signal quality SQ values is negative, at which time an alert is given to the EP doctor. Other criteria may be used in method step 24 to trigger user alert 20.

As described above, activation maps are used during certain cardiac procedures. But during such procedures, a variety of other cardiac parameters may advantageously displayed. Among these may be: (1) a value for starting reference-channel cycle length; (2) a value for current reference-channel cycle length CL with a confidence interval; and (3) a value for LAT with a confidence interval. Each of these quantities is generated by the method disclosed herein. For example, a confidence interval for current reference-channel cycle length CL may be determined as the cycle-length range $R_{CL}$ from the method steps of FIG. 5. Cycle-length range $R_{CL}$ provides an indication of the amount of variability within cycle-length CL. A confidence interval for the LAT measurement may be ±0.5 the interquartile range as described above.

As described above, an activation map comprises a plurality of LAT measurements all of which are made relative to a particular reference-channel signal. One aspect of the inventive automatic method of measuring parameters of multi-channel cardiac electrogram signals includes the ability to compensate for signal degradation in the reference channel during the creation of an activation map. Since LAT maps are made relative to a specific reference channel, if the reference-channel signal being used degrades during mapping below a useful level of signal quality, the inventive method enables another reference channel to be selected and recreates the set of LAT measurements based on the new reference channel and generates a new map. This is possible since the inventive method computes reference-channel parameters as described above for several reference channels in real-time and stores the necessary parameters for use if needed. Very fast computation available with present computing equipment enables these "extra" channels to be recorded and analyzed in real-time without hindering the operation of the "current" channels being used to create a map.

Figure 8:
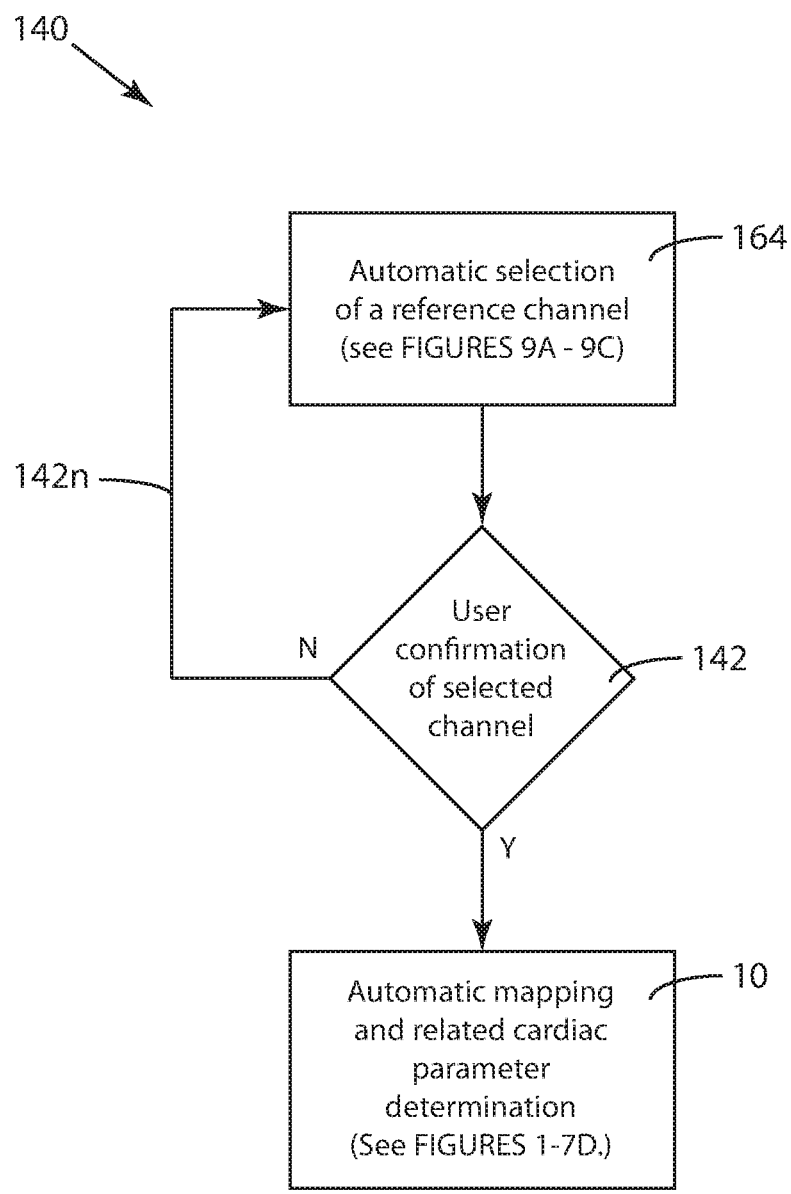
FIG. 8 is a schematic diagram illustrating the inclusion of automatic selection of the reference channels in the automatic method of measuring parameters of MCCE signals.

As seen above, the process of selecting a reference channel automatically is among the various aspects of the inventive automatic method. FIG. 8 is a schematic diagram illustrating the inclusion of automatic selection of a reference channel in the inventive automatic method of measuring parameters of MCCE signals. The steps of this overall combination are indicated by reference number 140.

Figure 9A:
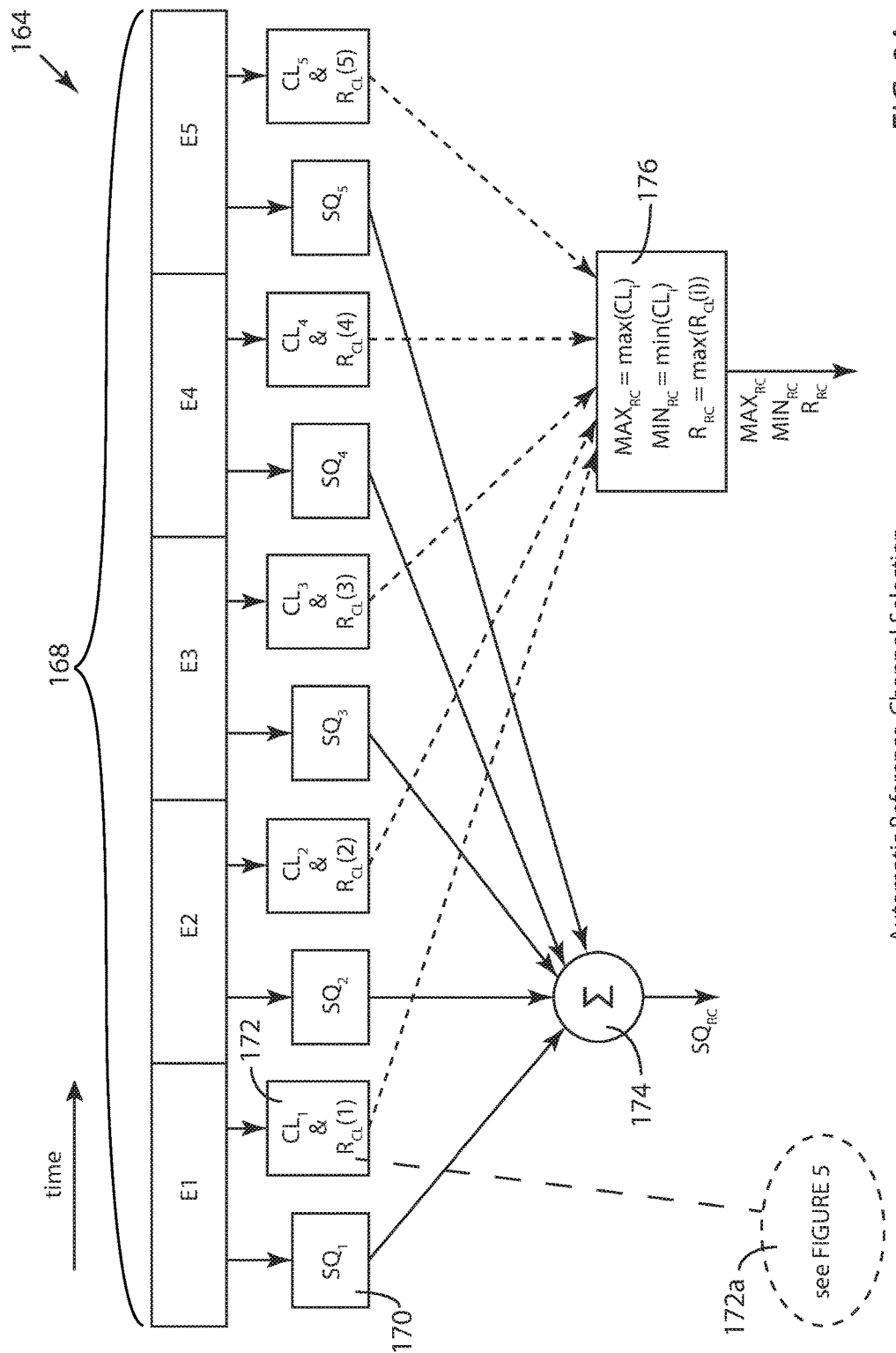
FIG. 9A is a schematic block diagram of the process of automatically selecting a reference channel from a set of candidate MCCE channels, specifically illustrating the determination of parameters for a single candidate reference channel.
Figure 9B:
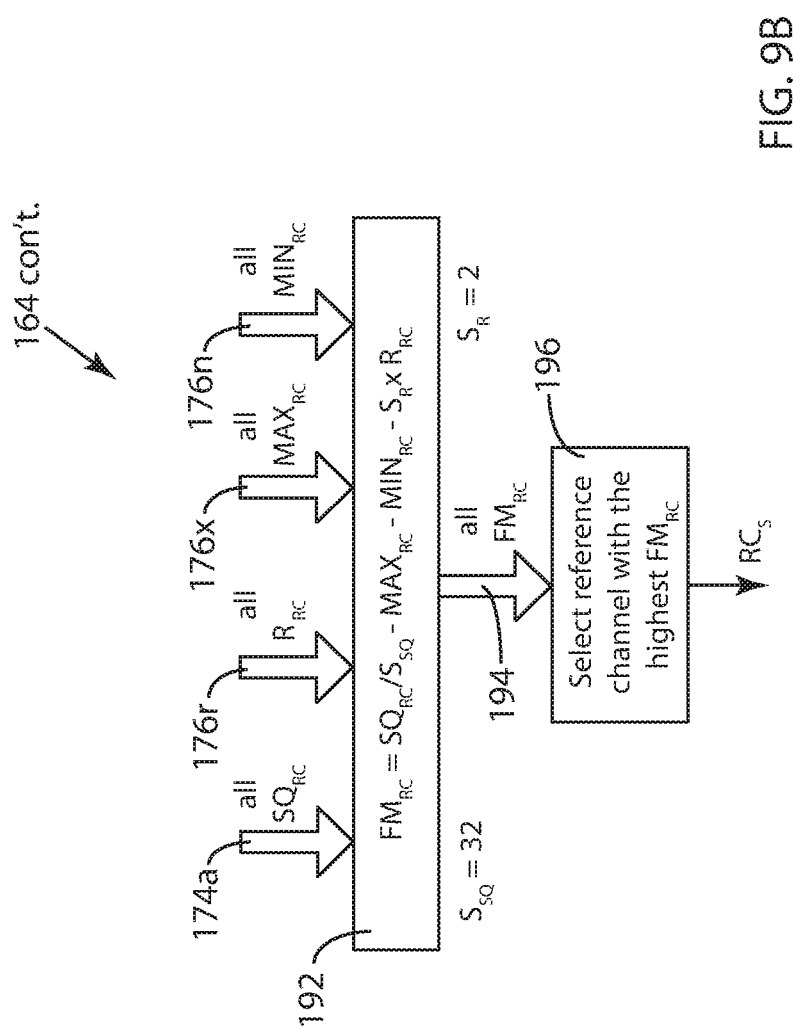
FIG. 9B is a schematic block diagram of the process of automatically selecting a reference channel from a set of candidate MCCE channels, specifically illustrating the automatic selection from among candidate reference channels which have had parameters determined in the automatic process of FIGS. 5 and 9A.

Referring to FIG. 8, this automatic initialization step includes automatic selection of a reference channel as indicated by reference number 164, and the method steps of an embodiment of automatic process 164 are illustrated in FIGS. 9A-9B.

The entire automatic method of the invention disclosed herein is under the control of the EP doctor, as indicated above. At the time of a medical procedure, there may be overriding medical or technical reasons for the EP doctor to reject a channel or the channels which have been automatically selected, so automatic method 140 includes a confirmation step 142 in which the EP doctor performing the procedure may accept or reject channels which have been automatically selected. If the EP doctor rejects a channel, indicated by the "N" option on confirmation step 142, channel selection may be done manually or a channel may be selected automatically as indicated by pathway 142*n*.

Upon final selection of a reference channel, automatic process 140 continues with the method steps of mapping as indicated by reference number 10 and as described in detail above.

FIGS. 9A and 9B are schematic diagrams of embodiment 164, 166 of the process of automatically selecting a reference channel from a set of candidate channels. It is desirable that the reference channel selected be a channel which exhibits high signal quality and low cycle-length variability and also which exhibits a fast heart rate. For physiological reasons related to the cardiac measurements for which the present invention is intended to be used, it is also desirable that the selected reference channel indicate the shortest cycle length CL. All of these criteria are used to select a reference channel from among the set of candidate reference channels.

Referring to FIG. 9A, in automatic process 164 for selection of the reference channel, an initial time period for capturing and assessing signal characteristics from all candidate channels is employed. Data are captured during the time period represented by five epochs, labeled E6 through E10. (Epochs E1 through E5 are also called sub-signals E1 through E5.) In the embodiment of FIG. 9A, this additional initial period is 30 seconds long. The signal from each candidate reference channel is an absolute-value velocity signal generated as described above. During the reference-channel selection process, there may be numerous possible channels being evaluated. What specific channels are candidate reference channels for cardiac mapping are well-known to those skilled in electrophysiology. The process illustrated in FIG. 9A is applied to the waveform signals of each candidate channel individually, generating for each channel two measures by which the reference-channel selection is made.

Referring again to FIG. 9A, a 30-second signal 168 from each candidate channel is divided into five six-second epochs (sub-signals) E1 through E5. The 30-second period, six-second epoch length and number of epochs in the initial period are not intended to be limiting in any way. FIG. 9A illustrates the process for just one such candidate channel; a plurality of candidate channels is processed concurrently within reference-channel selection process 164.

As illustrated in FIG. 9A, the signals in each epoch E1-E5 are processed to determine the corresponding signal quality SQ1 in method step 170. (Five such separate signal quality calculations are performed; only one is labeled with reference number 170, but the marking SQ1 indicates this calculation being performed sequentially five times, each producing a value SQ1 for the signal quality of the corresponding epoch $E_i$.) Signal quality calculation 170 is carried out as illustrated in the steps of FIG. 4A.

In method step 174, the five signal quality values SQ1 are summed to produce an overall signal quality value $SQ_{RC}$ for each candidate reference channel.

Also illustrated in FIG. 9A, the signals in each epoch E1-E5 are processed in method steps 172 to determine a cycle length $CL_i$ and a value $R_{CL}(i)$ for cycle-length range for each of the five epochs. The cycle length determination (and cycle-length range) is performed using the method steps described in detail above and illustrated in FIG. 5. Five such cycle length and cycle-length range calculations as illustrated in FIG. 5 are performed; one is labeled with reference number 172a, but the markings of each such element in FIG. 9A indicate that this calculation is performed sequentially five times, each producing a value of cycle-length $CL_i$ and cycle-length range $R_{CL}(i)$ for the corresponding epoch.

Referring again to FIG. 9A, in method step 176, three additional values (in addition to $SQ_{RC}$) are determined for each epoch E1 through E5 by which to select from among the candidate reference channels: $R_{RC}$; $MAX_{RC}$; and $MIN_{RC}$. $MAX_{RC}$ is the maximum cycle length $CL_i$ among the five cycle-length values. $MIN_{RC}$ is the minimum cycle length $CL_i$ among the five cycle-length values. $R_{RC}$ is the maximum cycle-length range $R_{CL}(i)$ among the five range values.

At this stage in the automatic reference-channel selection process, each reference channel in the set of candidate reference channels has a channel signal quality assessment value $SQ_{RC}$, a channel cycle-length range $R_{RC}$, and maximum and minimum cycle length values $MAX_{RC}$ and $MIN_{RC}$ which will be used to complete the automatic reference-channel selection process.

FIG. 9B illustrates the final portion of reference-channel selection process 164 for this embodiment. In general, it is desirable to select a reference channel with high signal quality, low variability, and short cycle length, as indicated above. FIG. 9B illustrates an embodiment which selects the channel with these characteristics.

In FIG. 9B, the wide arrows labeled 174a, 176r, 176x, and 176n each represent a plurality of values as indicated. Wide arrow 174a represents all values of $SQ_{RC}$ from the candidate reference channels; wide arrow 176r represents all values of $R_{RC}$ from the candidate reference channels; wide arrow 176x represents all values of $MAX_{RC}$ from the candidate reference channels; and wide arrow 176n represents all values of $MIN_{RC}$ from the candidate reference channels.

In method step 192, a figure-of-merit $FM_{RC}$ is evaluated for each candidate reference channel. $FM_{RC}$ for each candidate reference channel is computed as follows:

$$FM_{RC}=SQ_{RC}/S_{SQ}-MAX_{RC}-MIN_{RC}-S_R \cdot R_{RC}$$

where $S_{SQ}$ and $S_R$ are arbitrary scale factors. The two scale factors are chosen such that a useful tradeoff within the figure-of-merit $FM_{RC}$ is created. When signal quality values $SQ_{RC}$ are in microvolts and cycle lengths are in milliseconds, a value of $S_{SQ}$ of 32 and a value of $S_R$ of 2 have been found to yield a useful tradeoff among cycle lengths, variability, and signal quality and also to be computationally convenient.

The $FM_{RC}$ values for each candidate reference channel are output from method step 192 as indicated by wide arrow 194. In method step 196, the channel with the highest value of $FM_{RC}$ is the selected reference-channel $RC_S$.

Other computational assessments of signal quality, cycle length and cycle-length range for each channel are of course possible. The specifics of these assessment embodiments, including the exemplary parameter values mentioned above, are not intended to be limiting.

As described above, one aspect of the inventive automatic method of measuring parameters of multi-channel cardiac electrogram signals includes the ability to compensate for signal degradation in the reference channel during the creation of an activation map by selecting a new reference channel and recreating the set of LAT measurements based on the new reference channel and generating a new map. During the initial selection process for the reference channel, the inventive method keeps track of the reference channels which have values for $FM_{RC}$ just below the selected reference channel $RC_S$ so that if necessary, these "second best" reference channels can be substituted for the selected reference channel and the mapping process can continue without losing the valuable time and effort that has already been spent on the mapping process.

In another aspect of the inventive method, multiple mapping channels may also be employed, and the processing steps outlined herein applied to multiple mapping channels as well as multiple reference channels. Some catheters used in cardiac procedures may include multiple electrodes in a variety of configurations. In addition, multiple catheters may be employed. The speed of computer processing available enables numerous calculations to be done very rapidly such that multiple mapping channels may be supported to generate a plurality of maps as the EP doctor moves the mapping electrodes throughout chambers and vessels of the heart.

Figures 10, 11:
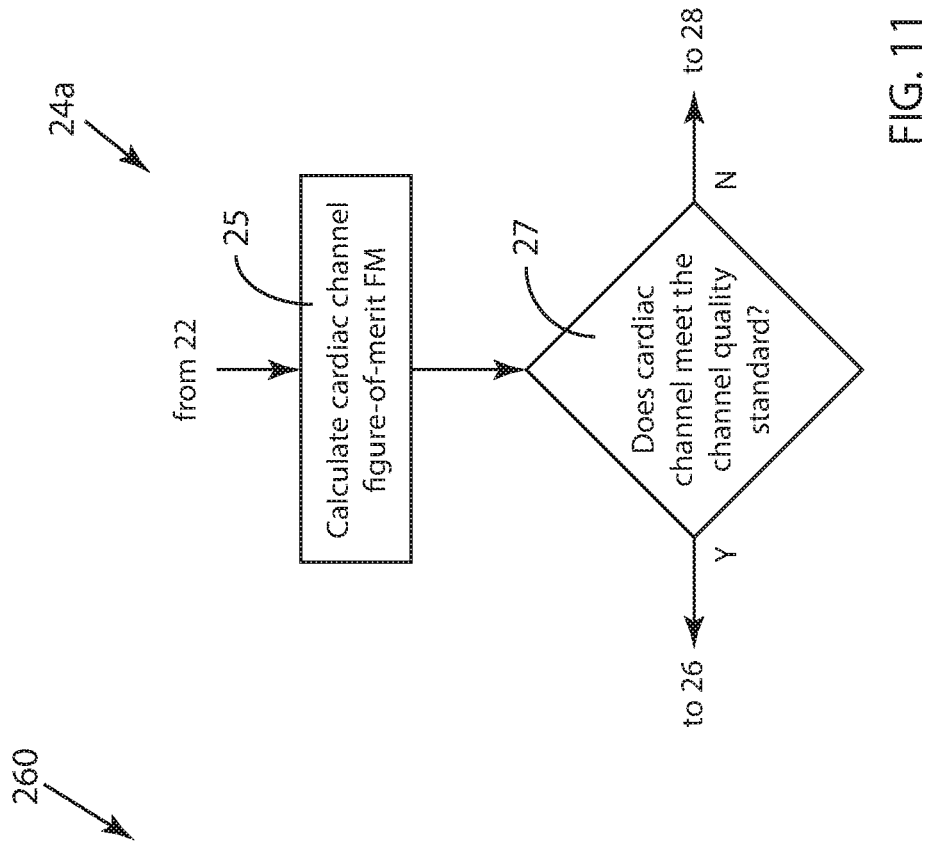
FIG. 10 is a matrix which schematically illustrates a series of channels used for reference or mapping among a set of MCCE signals which in an aspect of the inventive method may be processed in parallel to generate multiple LAT maps by various combinations of reference and mapping channels.
FIG. 11 is a schematic block diagram illustrating an alternative embodiment of the monitoring of cardiac channel quality. The alternative embodiment replaces a portion of the schematic block diagram of FIG. 1.

FIG. 10 is a matrix which schematically illustrates a series of reference channels and mapping channels from among a set of MCCE signals which in an aspect of the inventive method may be processed in parallel to generate multiple LAT maps as well as track the other cardiac parameters measured with the inventive method in a variety of combinations of reference and mapping channels. Some channels may be displayed for the EP doctor in parallel while others may serve as possible backups in case of signal degradation as explained above.

Referring to FIG. 10, the table 260 shown is an 8×8 matrix (eight channel signals which can be used as reference channels $R_1$ through $R_8$ and/or mapping channels $M_1$ through $M_8$. The number of channels illustrated is not intended to be limiting, but rather to illustrate the concept of flexible configuration combinations of reference and mapping channels. In fact, a set of MCCE signals is typically much larger than the eight illustrated here. Eight channels in the MCCE set of signals is only for purposes of illustration.) The "✓" symbol indicates that the mapping channel and reference channel at such an intersection together can generate a map. In other words, as shown in table 260 of FIG. 10, each channel $M_1$ through $M_8$ can be paired with any other channel $R_1$ through $R_8$, and any combination of these pairings can be created. The "-" simply indicates redundancy in table 260. The "-" symbol is located along the diagonal of table 260 indicating that any channel is not usefully paired with itself.

The advantages of such multiple-channel processing configurations are that procedure time may be shortened but also that a much richer array of measurements may be obtained to provide better information to the EP doctor to ameliorate the cardiac deficiency being treated. Further, as described above, backup channels can be available to deal with lost or degraded signals during a procedure without the need to start the procedure over again.

It is possible in some multi-channel configurations that certain information may be shared among several parallel computations. And many other combinations other than those exampled here are possible with the multi-channel processing of the inventive method described herein.

In embodiment 10 of the inventive automatic method of measuring parameters of multichannel cardiac signals described in detail above, contiguous six-second epochs of MCCE signal data are used. Alternatively, a moving-window format of selecting epoch starting and end points may be used, such as the next epoch in a series of epochs consisting of the last 5 seconds of the previous epoch and a new sixth second. Other epoch-forming strategies may be used, depending on the computational advantages which may be possible and on the desired speed of analysis.

FIG. 11 is a schematic block diagram illustrating an alternative embodiment of the monitoring of cardiac channel quality. The alternative embodiment replaces a portion of the schematic block diagram of FIG. 1. As previously described and as illustrated in FIG. 1 and in FIG. 4A, signal quality is defined as a quantity dependent on signal strength, signal irregularity and noise. In addition to such a specific assessment of signal quality, an overall channel-quality assessment may include information on the variability of the cycle length. Such an overall assessment for a reference channel is represented by a figure-of-merit which reflects the fact that higher signal quality values and lower cycle-length variability are desirable.

In order to make an assessment of overall channel quality during ongoing operation of the inventive method, one embodiment of such a system includes applying the steps of automatic channel selection for initialization in real-time to monitor channel quality. These channel selection steps are fully described above and illustrated in FIGS. 8-9B. As described in these embodiments, assessment of overall channel quality includes calculation of various signal quantities over a plurality of epochs. In these embodiments, five contiguous six-second epochs are evaluated as shown in FIGS. 9A and 9B. The number of epochs may vary and the length of the epochs may also differ from 6 seconds. Further, signal parameters may be computed over moving time windows rather than sequential (contiguous) epochs. The epochs may be of fixed-length or of various lengths. Any number of variations of time periods are possible in the computation of the elements of channel figures-of-merit, signal quality and cycle-length variability.

The schematic of FIG. 11, labeled with reference number 24a, replaces element 24 in FIG. 1 in the alternative embodiment of FIG. 11. The connections to the block diagram are shown as connections with elements 22, 26 and 28 of FIG. 1. The functional elements 25 and 27 represent the alternative functions of calculating a figure-of-merit FM (element 25) and using figure-of-merit FM in comparison to a channel quality standard (element 27). Such a standard may be a preset threshold value that figure-of-merit FM must exceed or it may be a dynamically-determined standard such as being the highest figure-of-merit FM among a set of candidate channels. Other standards are also possible such as, for example, a combination of a preset threshold value and the maximum among a set of channels. In such a case, a channel has acceptable overall quality when it has a figure-of-merit FM which is both the highest in a set of channels and is above a preset threshold value.

The calculation of figure-of-merit FM as illustrated in FIG. 11 involves the application of the steps of FIGS. 9A and 9B for the assessment of the overall quality for candidate reference channels. As described above, various strategies for determining the timing of signals used are possible.

In this inventive method, a plurality of channels are stored and processed such that the monitoring of overall channel quality is possible for cardiac channels as desired. The inventive method includes a variety of strategies for monitoring overall cardiac channel quality, including (a) performing the necessary calculations in real-time for only one or more of the "active" channels (the currently used mapping and reference channels for LAT determination), (b) performing the necessary calculations in real-time for the entire plurality of cardiac channels, and (c) performing such calculations for a subset of cardiac channels. Since channel signal data is stored, if a strategy such as (a) is chosen, overall channel quality of other ("non-active") channels can be performed when necessary to determine which channel will replace the current cardiac channel. If a strategy such as (c) is employed, the inventive method monitors every cardiac channel, making an up-to-date assessment of the overall channel quality for every cardiac channel in the system available at any time.

Figure 12:
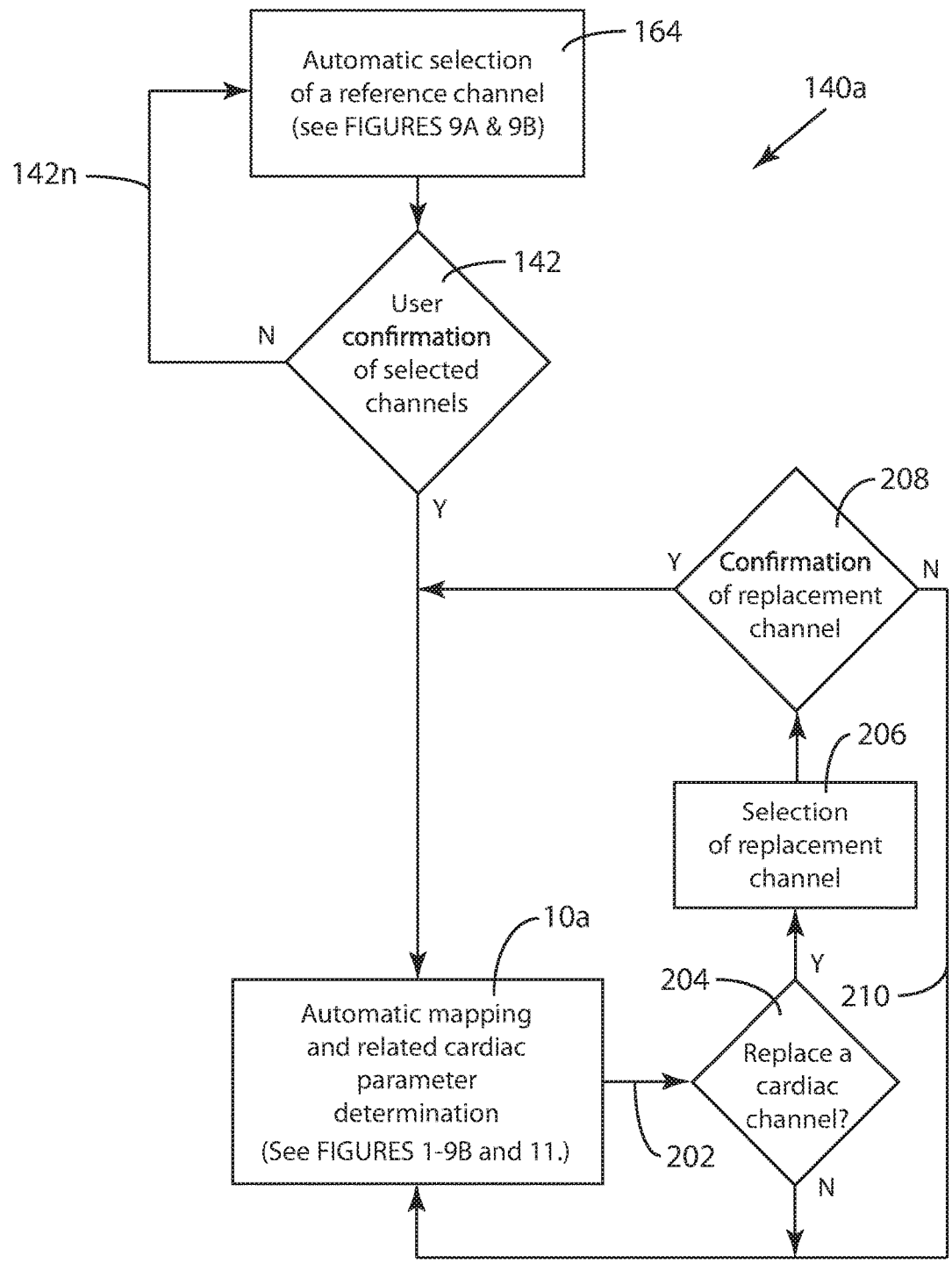
FIG. 12 is a schematic block diagram illustrating an alternative embodiment of the channel selection method illustrated in FIG. 8, adding elements of the automatic channel selection steps within initialization to the real-time operation of the inventive method for measuring parameters of MCCE signals such that cardiac channels may be replaced when the quality of a channel signal degrades during operation of the inventive method.

FIG. 12 is a schematic block diagram illustrating an alternative embodiment of the channel selection method illustrated in FIG. 8, adding to real-time operation the steps of automatic channel selection which in the embodiment of FIG. 8 operate only within the initialization process. The method steps of FIG. 12, indicated together as 140a, include not only the initialization steps from the embodiment of FIG. 8 but also elements 202 through 210. Element 10a, as shown, is a modification of element 10 in FIG. 8, modified to include the now real-time automatic steps embodied in FIGS. 9A, 9B and 11. Elements 202 through 210 describe an embodiment which carries out cardiac channel replacement during real-time operation of the inventive method, replacing a reference channel when the overall quality of such channel degrades during operation.

Method element 10a encompasses the running (real-time) operation of the inventive method as detailed in FIGS. 1-9B and 11. Connection 202 and method element 204 illustrate the step of deciding if a cardiac channel needs to be replaced, the result of calculating figure-of-merit FM in step 25 and making a comparison with a channel-quality standard in step 27 of FIG. 11. A user alert is generated in step 28 (see FIG. 1), and decision step 204 may proceed in a completely automatic fashion if the user chooses such automatic functioning. In such a case, an alert at step 28 is still provided to the user. However, it is anticipated that the user may intervene in the automatic steps of channel replacement to exercise more control over the replacement process. An "N" decision in decision step 204 returns the process to overall running-time operation represented in element 10a.

The inventive method in embodiment 140a proceeds to method element 206 in which a replacement channel is selected, either automatically or manually by the user, based on assessments of possible replacement cardiac channels. Embodiment 140a proceeds then to method step 208 in which confirmation of the channel replacement is carried out, either automatically or by user intervention. With a "Y" decision at decision step 208, the process continues channel replacement and updating in element 210 and then the process continues with overall running-time operation represented in element 10a. An "N" decision at decision step 208 returns the process to overall running-time operation represented in element 10a without channel replacement and updating.

Transformation of Local Activation Times

Figure 13:
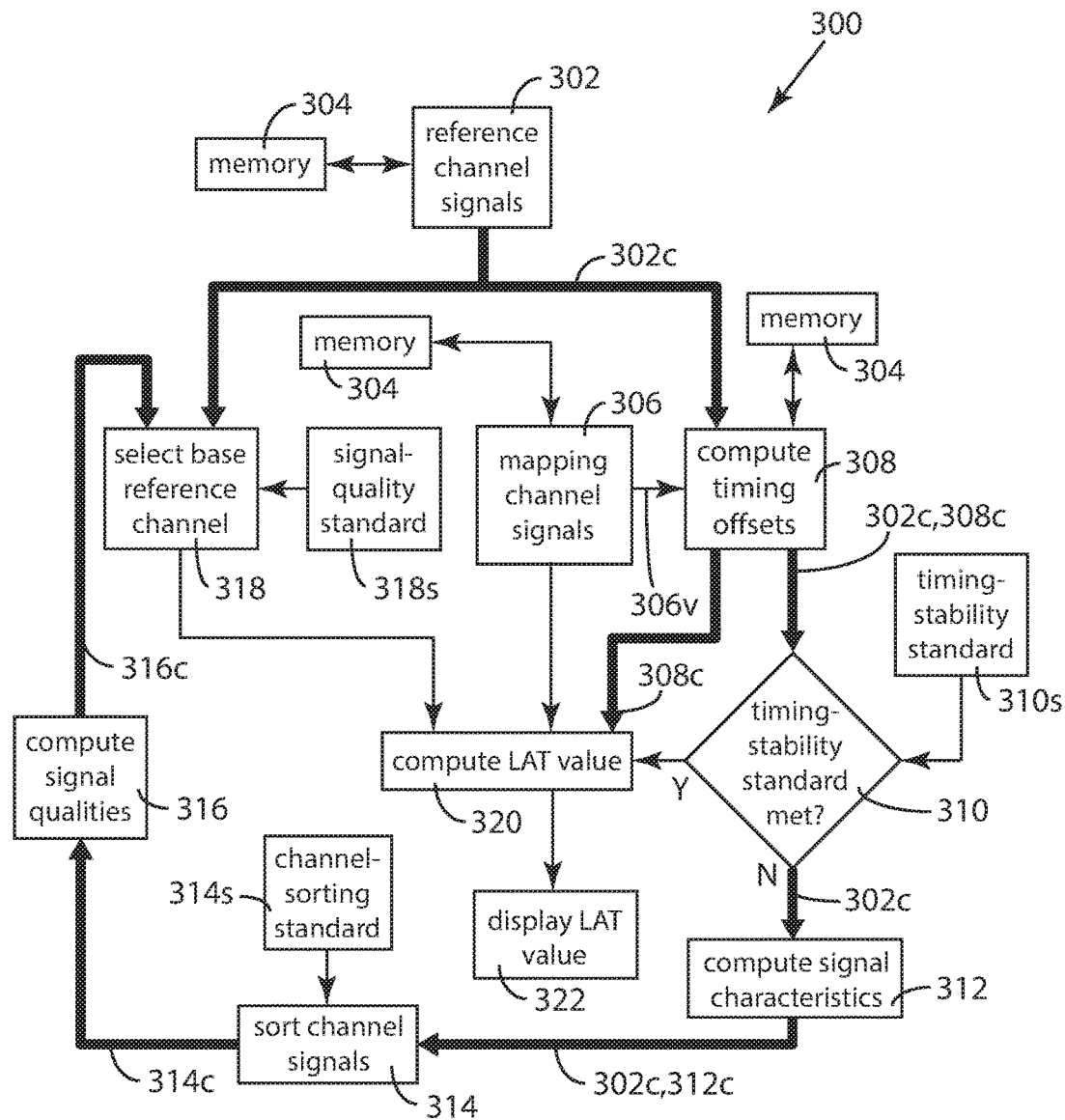
FIG. 13 is a high-level schematic block diagram illustrating the steps of an embodiment of the inventive method for transforming LAT values using a second reference-channel signal when the timing stability of a first reference-channel signal degrades below a stability standard, in order to avoid substantial loss of LAT values in spite of the loss of timing stability.

FIG. 13 is a high-level schematic block diagram illustrating the steps of an embodiment 300 of the inventive method for transforming LAT values using a second reference-channel signal when the timing stability of a first reference-channel signal degrades below a timing-stability standard, in order to avoid substantial loss of LAT values in spite of the loss of timing stability. Method element 302 represents a plurality of reference-channel signals among the MCCE electrogram signals available for processing. Mapping-channel signals 306 are also among this set of available MCCE signals.

Method elements 304 (three shown) represent the step of storing these cardiac signals. Method embodiment 300 may be realized within a computer programmed to carry out the steps as described herein, and the divisions between the method elements may vary based on the programming generated to carry out such steps. Other quantities in addition to the cardiac electrogram signals may be captured in computer memory, although not shown in FIG. 13 (other than timing offsets in method element 308), in order to enable other computed values to be generated as desired, either during a procedure or retrospectively.

Connection 302c is drawn as a wider arrow to represent that the plurality of reference channels 302 are available within the method structure along a connection 302c as shown. A connection labeled 302c is shown in three other locations within the schematic block diagram of FIG. 15 to indicate that reference channels 302 are also available at these points within the block diagram of embodiment 300. In similar fashion, other connections are indicated by reference numbers ending with the letter "c" to indicate that multiple quantities are available thereon as indicated by the reference number of the method element and/or the nature of the multiple quantities available at such connections. For example, method element 314, to be described later, is the source for the quantities available on connection 314c.

Three method elements in FIGS. 13 (310, 314 and 318) involve the application of a standard by which a determination is made within embodiment 300 of the inventive automatic LAT-determining method. These standards are indicated by reference numbers ending with the letter "s" and which include the reference number of the method element in which such a determination is made.

A first reference channel is established as the base reference channel for the LAT computation carried out in method element 320. Method element 320 is shown as having the two requisite channel signals (mapping and reference) as indicated by connections from method elements 306 and 318. LAT computations are carried out in method element 320 using a number of possible ways of determining parameters within these signals. One such approach to LAT computation is described in this document in FIGS. 6A and 6B, their related figures, and the accompanying description. However, this example approach is not intended to be limiting; numerous other approaches for determining the necessary quantities for an LAT computation are within the scope of the present invention.

In method element 308, timing offsets are computed to be used in the determination of LAT values as required and also for a determination in method decision element 310 of whether or not the timing stability of the first reference-channel signal (base reference-channel signal) has fallen below a timing-stability standard 310s. (Timing-stability standard 310s will be described later in this document.) In embodiment 300, the timing offsets used to transform local activation times are themselves also local activation times and are defined as $LAT_K(J)$ where $LAT_K(J)$ is the local activation time of a reference channel J based on a reference channel K. In method element 308, timing offsets are computed for pairs of the plurality of reference channels 302.

For example, if there are five reference channels 302, then there are ten pairs within reference channels 302 for which timing offsets may be calculated. (In general, with n possible reference channels available, there are $(n^2-n)/2$ timing offsets which may be computed.) Note that $LAT_J(K)=-LAT_K(J)$ so that in this case there are 20 timing offsets which may be available for later use if each pair has had a period of time during which the timing stability of both signals has been satisfactory. It is most desirable that all possible pairs may be used for such timing offsets computations, but alternatively only a subset of the available pairs may be used.

In method decision element 310, if it is determined that timing-stability standard 310s has been met, method embodiment 300 simply proceeds along the "Y" branch of method decision element 310 to process the next epoch of electrogram signal data in method element 320 without replacing the first reference channel (the base reference channel) with a second reference channel. However, if it is determined that timing-stability standard 310s has not been met (i.e., there likely has been a disruption caused, for example, by electrode displacement, degraded electrode contact or noise), the method of embodiment 300 proceeds along the "N" branch of method decision element 310 to method element 312 in which certain characteristics of the reference-channel signals 302 are computed to enable embodiment 300 to make a determination of which channels among the reference-channel signals 302 have been disrupted.

Method decision element 310 as described here, while determining that timing stability has been degraded below timing-stability standard 310s, does not determine which channel(s) has/have caused this loss of timing stability. Such determination is made in method elements 312 and 314. Note that four specific embodiments of signal characteristic computations 312 are described later in this document. These four embodiments are not intended to be limiting; other computations of signal characteristics may be used within the intent of method element 312. Connection 312c indicates that the signal characteristic results of method element 312 are available to method element 314.

Method element 314 represents the method step of sorting reference channels 302 according to whether or not specific channels have been disrupted and are therefore not available to be selected in method step 318 as the second reference channel. This sorting is accomplished by comparison of computed signal characteristics with a channel-sorting standard 314s. The output of method element 314 is a subset of reference channels available along connection 314c which may be selected as the second reference channel (new base reference channel for LAT determination).

In method step 316, the signal qualities of each available reference channel are determined, and in method step 318, a selection is made of the second reference channel based on a signal-quality standard 318s. A number of signal quality computations may be made in method element 316, examples of which are high signal amplitude, low signal noise, low signal amplitude variability, low cycle-length variability and short cycle length. Some approaches to computing signal quality are described earlier in this document, such as in sections related to automatic selection of channel signals. None of these specific measures of signal quality are intended to be limiting to the scope of this invention; other computations of signal quality are possible within the intent of method element 316. Connection 316c indicates that the signal characteristic results of method element 312 are available to method element 318.

During a cardiac mapping procedure, the electrodes of the reference channels 302 ideally remain stationary. Since the reference-channel electrodes ideally remain stationary, a set of timing offsets $LAT_J(K)$ are computed in method element 308 using pairs from among the reference channels 302, the values of the timing offsets being computed in advance of their being needed.

MCCE signals are by their very nature noisy from a number of sources, and thus the determination of LAT values, and of course, timing offsets, is a statistical process. Transformation factors may be established by averaging a set of $LAT_J(K)$ values for the pair of reference channels (J,K) over a period of time during a cardiac mapping procedure, and the statistical variations in $LAT_J(K)$ may be used as part of a determination as to whether a reference channel is suitable to remain as the first (base) reference channel or to be available to be selected as the second (new base) reference channel. Among the causes of stability degradation is of course the physical movement of a reference-channel electrode such that its location has changed and therefore cannot be relied upon as a suitable reference.

When a new base channel (second reference channel) has been selected in method element 318, the computation of LAT values in method element 320 changes from the straightforward use of the mapping channel and the base reference channel to include the use of one or more timing offsets. The availability of the timing offsets in method element 320 is indicated by the timing offsets being inputs along connection 308c.

The transformation process triggered by a change from the first reference channel to the second reference channel is represented by the equation $LAT_A(C)=LAT_A(B)+LAT_B(C)$ where timing offset $LAT_B(C)$ is the local activation time of reference channel C based on a reference channel B, and such timing offset $LAT_B(C)$ transforms values $LAT_A(B)$ into LAT values $LAT_A(C)$. As indicated, computation of LAT values in method element 320 may include a straightforward calculation of an LAT value without the application of a timing offset or it may include transforming a past or current LAT value with the appropriate timing offset. Method element 322 represents that LAT values may be displayed in a map or other form as desired by the EP doctor.

One important aspect of the inventive automatic method is that it is able to transform both past and future LAT values so that an LAT map, once it has been started and considerable investment of time (both patient and medical personnel) has been undertaken along with possible exposure to X-ray radiation, the LAT map is able to be completed without the loss of such investment made in the capturing of LAT values.

As an example, an LAT map is partially generated based on the first reference signal, such LAT values of mapping channel M being represented by $LAT_1(M)$. Then, during this procedure the quality of the first reference signal degrades, and the first reference-channel signal is replaced by a second reference-channel signal. Each of the past LAT values $LAT_1(M)$ may be transformed into LAT values $LAT_2(M)$ by $LAT_2(M)=LAT_2(1)+LAT_1(M)$. New LAT values $LAT_2(M)$ may continue to be captured based on the second reference-channel signal, and the completed map in this case is now based on the second reference channel. However, all of the points $LAT_1(M)$ that were captured based on the first reference channel have been used to build the new map without having to be recaptured. The timing offset $LAT_2(1)$ has been established over time during periods in which both the first and second reference-channel signals were signals having suitable timing stability and quality.

In another example, an LAT map is partially generated based on the first reference signal, such LAT values of mapping channel M being represented by $LAT_1(M)$. Then, during this procedure the quality of the first reference signal degrades, and the first reference-channel signal is replaced by a second reference-channel signal. New LAT values $LAT_1(M)$ may be determined by computing LAT values $LAT_2(M)$ based on a second reference signal and then transformed into LAT values $LAT_1(M)$ by $LAT_1(M)=LAT_1(2)+LAT_2(M)$. The completed map in this case is still based on the first reference channel, and all of the points $LAT_1(M)$ that were captured based on the first reference channel have been used in the map with new LAT values added to the map having been transformed into LAT values based on the same (first) reference signal. The timing offset $LAT_1(2)$ has been established over time during periods in which both the first and second reference-channel signals were signals having suitable timing stability and quality.

In the high-level schematic block diagram of FIG. 13, a number of more detailed steps are implicitly embedded in the method elements shown in embodiment 300. For example, among these functions are: (1) the logic and control within method element 320 to determine whether a future-value transformation or a past-value transformation is appropriate for the LAT computation; (2) the sequential processing of the channel signals (e.g., from epoch to epoch); and (3) the logic and control necessary to capture an LAT value when the EP doctor decides that such a value should be captured. The automatic nature of the inventive method of determining LAT is not compromised by the manual intervention of the EP doctor to "take a point" for mapping. The method proceeds automatically, computing LAT values, monitoring timing stability, and selecting replacement channels as described herein, with a "take point" process operating over the top of such automatic method.

Also implicitly included in the method elements of embodiment 300 is logic control of the automatic method whereby after a reference channel has been replaced due to a loss of timing stability, a period of time is provided during which the statistics of the timing offsets are reestablished with the new set of electrode conditions such as might have been caused by a reference-channel electrode having shifted its position. For example, if six-second epochs are being used and twenty data points are regarded as sufficient, a period of two minutes would be required to reestablish such statistics.

FIG. 14 is a table 309 showing exemplary mean values for timing offsets as computed in method element 308 of FIG. 13. This example is of a reduced set of six cardiac channels. As described above, the timing offsets are local activation times $LAT_J(K)$, the local activation time of a reference channel K based on a reference channel J where channels J and K are reference channels within a set of possible or candidate reference channels in the reduced set of MCCE channels. In this example, none of these channels would intentionally be used as an exploring catheter (mapping channel).

The first two columns from the left of table 309 indicate the channel numbers for the timing offset calculations. Each entry in the third column of table 309 contains an LAT value to be used as a timing offset for the activation delay from one possible reference electrode to another possible reference electrode. As such, reference channel K takes the role of the mapping channel within an LAT calculation in method element 308, and a negative LAT value indicates that the activation arrives first at the channel K electrode which is filling the role of mapping channel. As mentioned above, $LAT_J(K)=-LAT_K(J)$; thus, half of the available timing offsets need not be shown in table 309. Since six possible reference channels are available in this example, fifteen timing offsets are computed, and thirty offsets are available.

The timing offset values shown in the third column in table 309 are the mean values of each computed timing offset, averaged over a predetermined number of computed values. For this example, the timing offsets are computed for six-second epochs of signal data over a period of two minutes; therefore, 20 timing offset values are averaged to produce the mean values shown in table 309. The predetermined number (20) of epochs and the 6-second length for each epoch are not intended to be limiting; other values for these two variables may be used.

It is assumed that repeated measurements of the timing offset between two channels with stationary electrodes will populate a Gaussian distribution with a mean and standard deviation (stdev). The fourth column of table 309 shows the standard deviation of each of the 15 timing offset values over the 20-sample (two-minute) history of computed timing offset values. The statistics of the third and fourth columns are determined on a two-minute moving window to be used in the determination of method element 310 as to whether or not timing stability has been lost. Data from the epoch immediately following the two-minute window are used in conjunction with the statistics of the two-minute moving window to make determination 310. If it is determined in method element 310 that timing stability has not been lost, the means and standard deviations for the new two-minute moving window are updated and are ready for the data from the next six-second epoch to be processed.

The data in the fifth and sixth columns represent a next epoch (epoch following the updating of the moving-window statistics). These two columns represent data taken from an epoch in which timing stability has not been lost, i.e., before loss of timing stability. The fifth column of data, labeled X, contains 15 individual computed timing offset values, one for each pair of channels in the set of timing offset pairs. For example, the timing offset $LAT_1(2)=-24$ msec and the timing offset $LAT_3(6)=-42$ msec.

Method element 310s indicates the use of a timing-stability standard (also indicated by reference number 310s) in the determination of method element 310. Since it is assumed that the timing offsets have Gaussian distributions, one example of a useful timing-stability standard 310s is to compute Z-scores for the timing offsets X for the epoch immediately after the current two-minute moving window for which the statistics have been calculated. This statistical test quantity is computed as $$Z\text{-score}=(X-\text{mean})/\text{stdev}$$

and values for the fifth column of timing offsets X are shown in the sixth column. A Z-score exceeding ±2 indicates that a new timing offset (in the set of values labeled X) has significantly (with 95% confidence) deviated from the expected distribution, thereby indicating that some change has occurred. As can be seen in the sixth column, none of the Z-scores exceeds ±2, indicating that it is unlikely that timing stability has been lost as defined by this example timing-stability standard 310s.

The seventh and eighth columns of table 309 are outlined in bold. The data in the seventh column of table 309 illustrates an example of an epoch before which timing stability has likely been lost. As method embodiment 300 proceeds and an epoch has been found not to have indicated a loss of timing stability, the two-minute moving-window statistics would be updated with the latest data before proceeding to the next epoch data. In the simplified example of table 309, the timing offset values X in the seventh columns are assessed against the statistics in columns three and four to illustrate the detection of the loss of timing stability.

The eighth column shows the Z-scores for the timing offset values in the seventh column, and it can be seen that two timing offset values, $LAT_2(4)$ and $LAT_2(6)$, have Z-scores which exceed −2, indicating that timing stability is very likely to have been lost prior to this epoch. (These two Z-scores are highlighted by gray shading.) Because timing offsets represent a relationship between two channel signals, when a timing offset changes, it is not known which channel (or both) have shifted or otherwise have lost a satisfactory signal. In method element 312 of embodiment 300, signal characteristics of reference-channel signals are computed for the purpose of determining which channel(s) has/have caused the loss of timing stability as detected in method element 310.

When timing stability has been found to have been lost, it may become necessary to provide extra time during which the statistics of some computed timing offsets are reestablished. This could be achieved by enabling a timer to prevent such channels from use during, for example, a two-minute period.

The timing stability standard 310s exampled in table 309 is not meant to be limiting; other indications of loss of timing stability may be used and are within the scope of the claimed invention.

Figure 15:
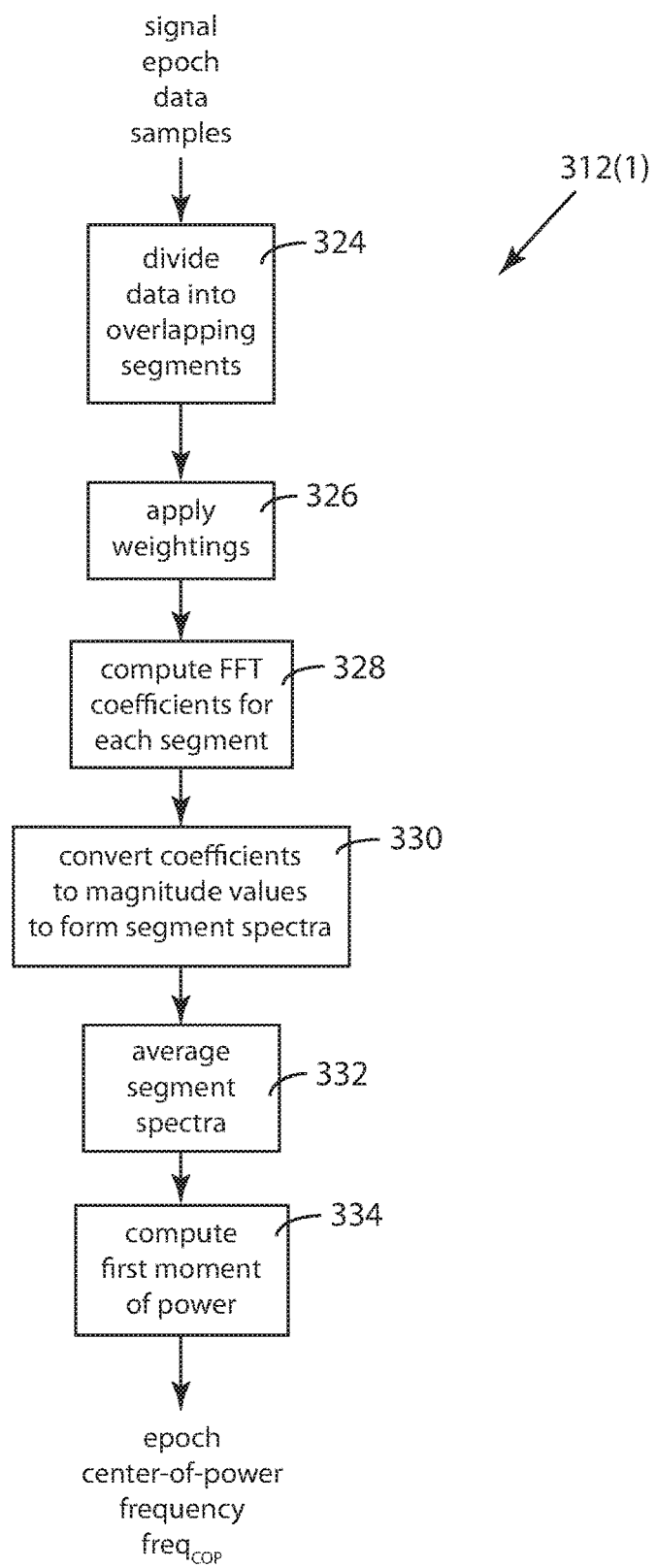
FIG. 15 is a schematic block diagram illustrating the steps of a method for computation of a signal characteristic for use within the method embodiment of FIG. 13. This signal characteristic computation generates an FFT-based (fast Fourier transform-based) parameter called herein the epoch center-of-power frequency.

FIG. 15 is a schematic block diagram illustrating the steps of an FFT-based method embodiment 312(1) for computation of a signal characteristic for use within method embodiment 300. This signal characteristic computation 312(1) generates an FFT-based parameter called the epoch center-of-power frequency $\text{freq}_{COP}$ and is used within the example of FIGS. 14 through 15N illustrating embodiment 300. In the method steps of embodiment 312(1), a fast Fourier transform (FFT) is computed for each relevant channel signal in an epoch. Computation of an FFT is well-known to those skilled in the art of signal processing and is not detailed herein.

Figure 15A:
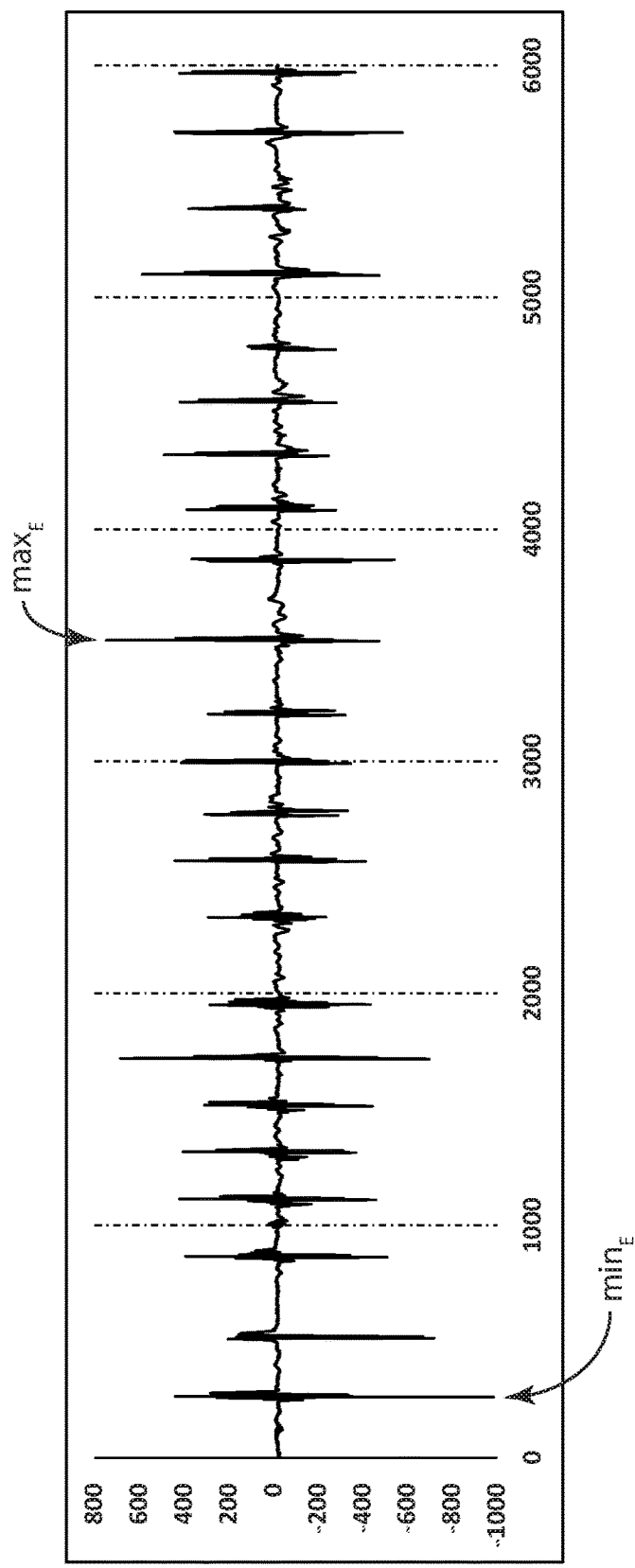
FIG. 15A is an exemplary six-second epoch of a representative cardiac channel electrogram signal.

FIG. 15A is an exemplary six-second epoch of a representative cardiac channel electrogram signal which is used to illustrate method embodiment 300, and in particular, to illustrate four alternative methods 312(1)-312(4) for computation of a signal characteristic for use within method embodiment 300. (The abscissa for the exemplary epoch of FIG. 15A is in millisecond (msec) or sample index for the 6,000 signal values in a six-second epoch.) In method element 324 of FIG. 15, each such channel signal is divided into overlapping segments of data for the purpose of a more time-efficient computation of the FFT—by computing an FFT for each of a plurality of shorter overlapping segments which span the time range of the signal. (This method for estimating the power of a signal as a function of frequency is similar to Welch's method or Welch's periodogram.)

Figure 15B:
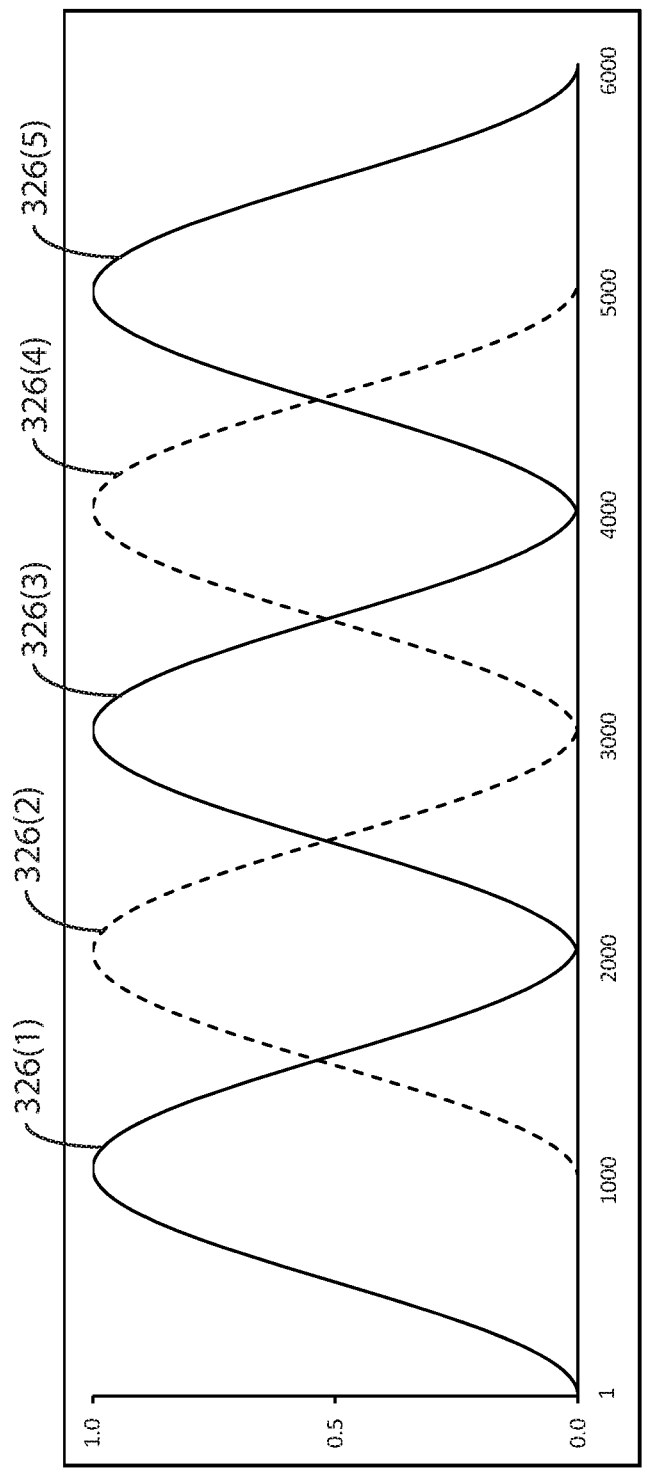
FIG. 15B is a plot illustrating one embodiment of weightings used to divide signal epoch data samples into overlapping segments of data. The weightings are applied to the signal data of FIG. 15A for use within the FFT-based signal characteristic computation of FIG. 15.
Figure 15C:
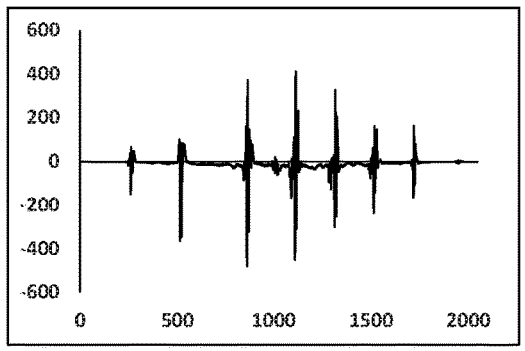
FIGS. 15C-15G are five plots illustrating the resulting segments having weightings applied to the cardiac channel signal of FIG. 15A, to be used in the computation of an epoch center-of-power frequency as illustrated in FIG. 15.
Figure 15D:
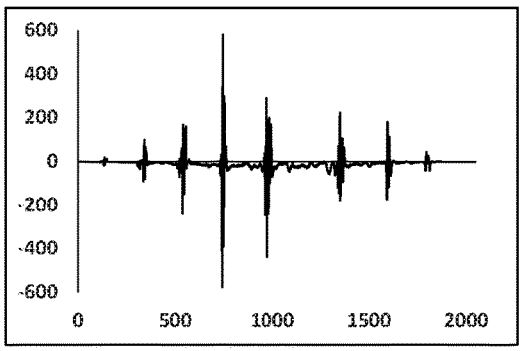
Figure 15E:
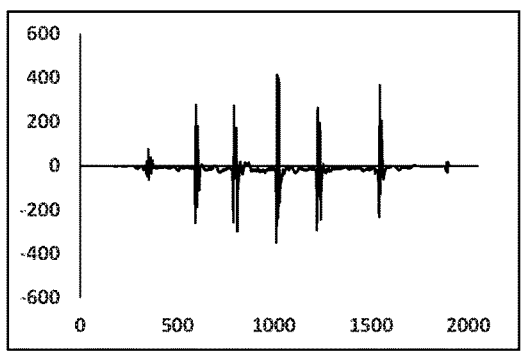
Figure 15F:
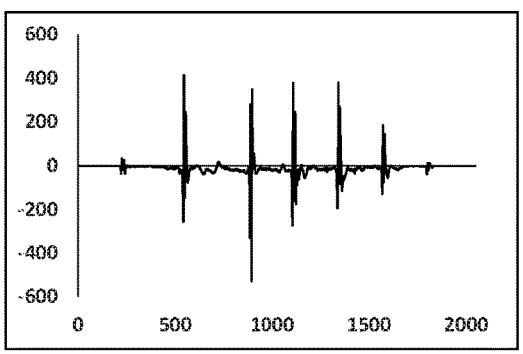
Figure 15G:
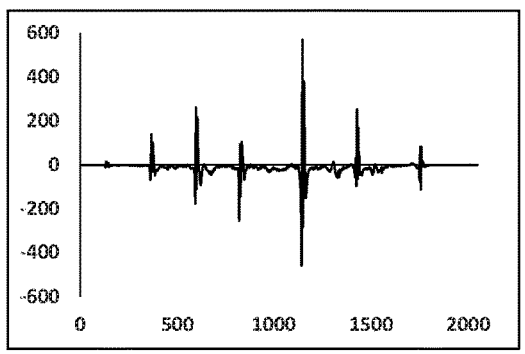

A six-second window of signal data with a sampling rate of 1,000 sps is divided into five overlapping blocks of 2,048 values of the signal which span the entire 6,000 data values in the six-second epoch, as illustrated in FIG. 15B. Each of the five curves 326(1)-326(5) is a raised and scaled sinusoidal curve also illustrating the weightings applied in method step 326. The weightings 326(1)-326(5) are applied individually to segments of the signal data. Each curve has 2,048 non-zero values. In FIG. 15B, curve 326(1) spans between data values 1 and 2,048; curve 326(2) spans between data values 977 and 3,024; curve 326(3) spans between data values 1,977 and 4,024; curve 326(4) spans between data values 2,977 and 5,024; and curve 326(5) spans between data values 3,953 and 6,000.

FIGS. 15C-15G are plots of the resulting weighted segments of signal data. (Note that the abscissa of each of the five plots in FIGS. 15C-15G span from 1 through 2,048 since the fast Fourier transform to be performed is on each segment individually although the weighted signal data are taken from different segments of the epoch as indicated above.) The segmenting and the application of weightings as illustrated in this example causes a net attenuation of the total power in each segment since the maximum weighting in each segment is 1.0 and the average across each segment is less than 1.0. However, since the same computation is applied to each epoch, the relative relationship of the resulting values is preserved, and the computation is much more time efficient.

In method element 328, an FFT is computed for each of the weighted signal segments. Each of the five segment FFT's computed in method element 328 is a 1,024-point FFT, i.e., there are 1,024 frequency coefficients (bins) each being 0.488 Hz wide (1,000/2,048). With a sampling rate of 1,000 sps, frequencies of up to 500 Hz can be measured. The resulting FFT coefficients are complex numbers, and in method element 330, these complex coefficients are converted to magnitudes to form 1,024 real coefficients.

FIGS. 15H-15L show the five resulting segment spectra for the weighted segment signal data of FIGS. 15C-15G, respectively, including the conversion of the FFT coefficients to magnitudes in method element 330. The average of these individual spectra is computed in method element 332 and results in the spectrum of FIG. 15M for the entire six-second epoch of signal data. (For computational efficiency, a sum could also be computed in method element 332 instead of an average, the only difference being the scale factor; these approaches are equivalent.)

In method element 334, the first moment of power is computed in order to determine the center-of-power frequency ($\text{freq}_{COP}$), as follows:

$$\text{freq}_{COP} = 0.488 \cdot [\Sigma(c_i^2 \cdot i)] / \Sigma c_i^2$$

where the $c_i$'s equal the 1,025 spectral coefficients (the 0 Hz and 0.488 Hz coefficients are set to 0 to remove these frequencies), i equals the bin number of the frequency bin in the spectrum, ranging from 0 to 1,024, and the sums are computed over the range of 1,025 bins (the abscissa of each plot is bin number). (i=1 is the 0.488 Hz bin number.) Conceptually, this center-of-power frequency can be thought of as the average of the bin distances (bin number) from 0 Hz with the bin distances being weighted by the power at the corresponding frequency of the bin. The corresponding frequency of each bin is 0.488 times the bin number so the maximum frequency available in the 1,000 sps signal is 500 Hz (the Nyquist frequency). Note that the 0 Hz and 0.488 Hz (bin numbers 0 and 1) coefficients are set to zero since these frequencies are substantially adulterated by the use of the raised-cosine segmentation process and therefore are not useful for determining the power spectrum.

The value of $\text{freq}_{COP}$ found for the spectrum of FIG. 15M is 107 Hz. Note that the exemplary signal epoch data of FIG. 15A has been captured through a 60 Hz notch filter as is often the case for cardiac electrogram signals. This can be seen in FIGS. 15H-15M as indicated by the deep V cut into the spectra around 60 Hz. As long as the filter remains in place throughout a procedure, its use is of little consequence to the ability of the inventive method to discriminate between signals.

It has been determined that center-of-power-frequency $\text{freq}_{COP}$ provides an excellent indication that a change has occurred in a cardiac channel signal. FIG. 15N shows a table 311 of the results of computations in method element 312 of the FFT-based $\text{freq}_{COP}$ signal characteristic for the example reduced-channel set of FIG. 14. In the first column of table 311, further specifics of the six channels are given. Cardiac electrogram channel 1 is shown as HRA (high right atrium) and channel 2 as HIS (bundle of His). These two channels are independent of all of the cardiac channels. (The bundle of His is a slender bundle of modified cardiac muscle that passes from the atrioventricular node in the right atrium to the right and left ventricles by way of the septum and that maintains the normal sequence of the heartbeat by conducting the wave of excitation from the right atrium to the ventricles. It is also called the atrioventricular bundle.)

The remaining four channels (A12, A34, A56, and A78) are all bipolar signals between two adjacent electrodes of an octo-polar catheter. (The signal epoch data of FIG. 15A is data from a representative six-second epoch from channel 5-A56.) The electrodes are at fixed spacings on the catheter and therefore are generally constrained to move together. The second column of table 311, labeled "Wire," shows an index of wires. Channels having the same wire index are on the same wire or catheter, and all channels having the same wire index are likely to be disrupted if the wire or catheter is disrupted.

The third and fourth columns of table 311 present the statistics (mean and standard deviation stdev) of each channel, the mean and standard deviation of the signal characteristic $\text{freq}_{COP}$ over a two-minute moving window (20 six-second epochs). The fifth column of table 311 presents current values of the $\text{freq}_{COP}$ (labeled X) for the epoch immediately after the current two-minute moving window for which the statistics have been calculated. This $\text{freq}_{COP}$ characteristic has units of Hertz (Hz) and is the frequency at the center of the bulk of signal power.

Table 311 of FIG. 15N also includes an embodiment of method elements 314 and 314s. After computing signal characteristics for the signals in method element 312, method element 314 sorts the channels based on the results of method element 312 to provide an automatic determination of which channel or channels caused the loss of timing stability detected in method element 310. A channel-sorting standard 314s is applied in the sorting of method element 314. Since it is assumed that the FFT-based $\text{freq}_{COP}$ values for each channel have Gaussian distributions, one example of a useful channel-sorting standard 314s is to compute Z-scores for the $\text{freq}_{COP}$ values X for the epoch immediately after the current two-minute moving window for which the statistics have been calculated. A Z-score exceeding 2 indicates that a new $\text{freq}_{COP}$ (in the set of values labeled X) has significantly (with 95% confidence) deviated from the expected distribution, thereby indicating that some change has occurred.

The sixth, seventh and eighth columns of table 311 contain absolute values of three different computed Z-scores. The isolated Z-score is computed for each channel based only on the statistics of that channel, as follows:

$$\text{Isolated Z-score} = \text{abs}[(X - \text{mean})/\text{stdev}]$$

The Group Z-score is the average of the isolated Z-scores of all the channels that share a common wire index, and the combined Z-scores are the averages of the isolated and group Z-scores for each channel.

In table 311, the channel 2-HIS and channel 6-A78 signals (see grayed entries) both indicate a significant change in the current measurement of the FFT-based freq$_{COP}$; each has shifted by more than two standard deviations. (The 2-HIS isolated Z-score is 2.4, and the 6-A78 Z-score is 2.1.) However, the 6-A78 channel is on a wire that constrains the 6-A78 electrode from moving much differently than the electrodes capturing three other signals. Because the three other signals have much lower Z-scores, there is a strong indication that the channel 6-A78 isolated Z-score, especially being only a little over the threshold of 2, may simply be due to natural variation and not of practical significance. (Even with a criterion like abs(Z)>2, one in 20 measurements are expected to be over the threshold simply by random chance.) The additional information about companion signals on the same wire (the four "A" channels) therefore assists in the recognition of a disrupted channel if the characteristic for that channel (6-A78) is near the Z>2 criterion, if many of the other companion signals less ambiguously satisfy the criterion, i.e., Z is much less than 2. Thus, in this particular example, the conclusion is that channel 2 (2-HIS) is the disrupted reference channel.

The specific computations illustrated in tables 309 and 311 are not intended to be limiting with respect to the ways in which the loss of timing stability and the detection of which channel or channels have caused such loss; other specific computational approaches may be used within the scope of the inventive automatic method of determining local activation time disclosed herein.

As indicated by the highlighted portion in gray shading in table 311, cardiac electrogram channel 2-HIS is the channel which embodiment 300 of the inventive automatic method applied to this reduced channel-set example has identified as having caused the loss of timing stability. In this case, if channel 2-HIS is the current base reference channel, it will be replaced with a new reference channel selected from the remaining set of candidate reference channels, and such replacement channel is selected based on signal quality computations in method element 316 which provide method element 318 measures of signal qualities to be compared based on a signal-quality standard 318s.

As indicated above, the qualities that may recommend a signal for use as a reference channel are: 1) high signal amplitude, 2) low signal noise, 3) low signal amplitude variability, 4) low cycle-length variability, and 5) shorter cycle length. Since several signal-quality measures determined in method element 316 and assessed in method element 318 using corresponding signal-quality standards 318s have been described above in this document, no further examples are presented here. For the purpose of selecting a new best replacement reference channel, these five channel qualities may be assessed over a longer time period since in embodiment 300 of the inventive method, such assessments occur in the background, not causing any delay in the LAT mapping function. In this case, the assessment could be over a longer period such as two minutes. The most recent epoch may be incorporated into the assessment since only non-disrupted channels will be considered.

Figure 16:
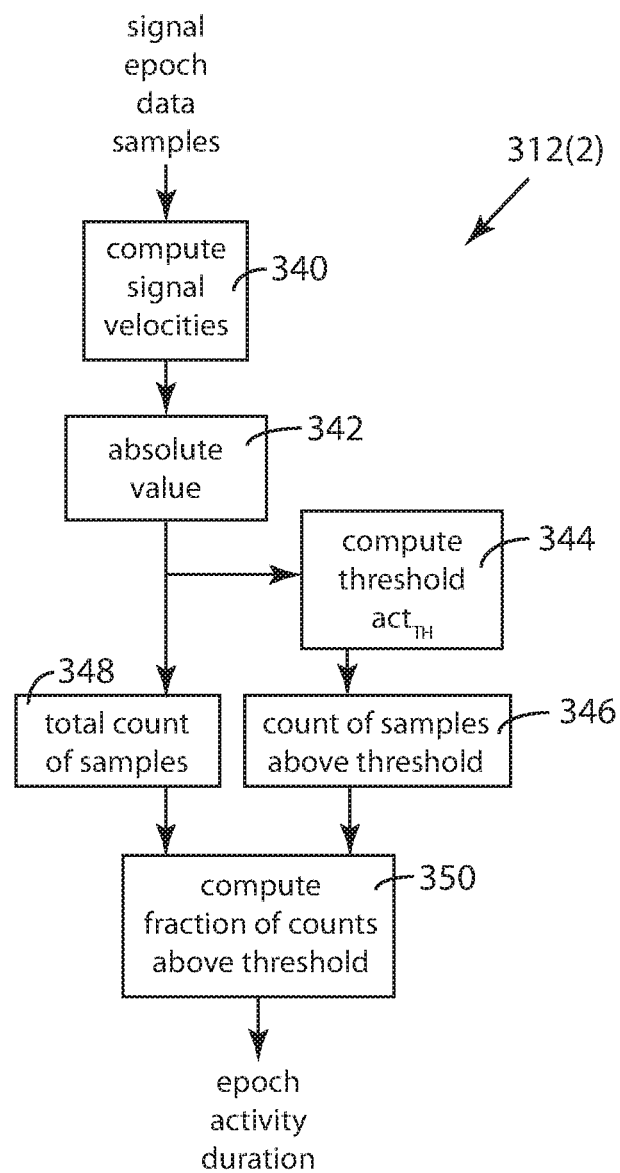
FIG. 16 is a schematic block diagram illustrating a first alternative method for computation of a signal characteristic for use within the method embodiment of FIG. 13. This alternative signal characteristic computation generates a signal characteristic called epoch activity duration.

FIG. 16 is a schematic block diagram illustrating an embodiment 312(2) of a first alternative method for computation of a signal characteristic for use within the method embodiment of FIG. 13. This alternative signal characteristic computation 312(2) generates a signal characteristic called epoch activity duration. In method element 340, values for the velocities of signal epoch data samples are computed using a method such as described above with respect to FIGS. 2-3B. The use of such method for computing signal velocities is not intended to be limiting. A number of approaches for signal velocity computation are well-known by those skilled in the art of signal processing, and such approaches are applicable within the inventive method claimed herein.

In method element 342, the absolute values of the velocities are determined, and in method element 344, an activity threshold act$_{TH}$ is computed. Since all MCCE signals contain some noise, it is necessary to define signal activity as occurring with signal levels above a threshold in order to avoid such noise corrupting the determination of activity duration. One useful definition of threshold act$_{TH}$ is four times the median of the data across the entire six-second epoch. Such threshold definition is not intended to be limiting to the present invention; other useful definitions of act$_{TH}$ may be used.

A signal is said to be active when the absolute value of the velocity is greater than act$_{TH}$. This comparison with act$_{TH}$ occurs within method element 346 which also counts the number of signal data values which exceed act$_{TH}$. Method element 348 counts the total number of signal data values, and in method element 350, the epoch activity duration is computed as the fraction of the total signal data values exceeding act$_{TH}$.

FIG. 16A is a plot illustrating the application of an absolute-value velocity filter to the exemplary six-second epoch cardiac channel electrogram signal of FIG. 15A. The median of the epoch signal data of FIG. 15A is 15 μvolts resulting in a value of act$_{TH}$ of 60 μvolts. The plot of FIG. 16A indicates the value of act$_{TH}$ used, and FIG. 16B is a plot illustrating computation of the activity duration signal characteristic for the absolute-value velocity epoch signal of FIG. 16A. Of the 6,000 total signal data values, 1,103 values were found to exceed act$_{TH}$=60, resulting in a value of activity duration of 0.184 for the exemplary signal epoch data of FIG. 15A.

It has been found that such an activity duration measurement is a useful signal characteristic by which to determine which cardiac channel or channels has/have been disturbed. Another such useful signal characteristic is simply a peak-to-peak measure across an epoch of cardiac channel data, and such a determination is described in FIG. 17 in method embodiment 312(3). Method elements 352 and 354 find the minimum and maximum signal values, respectively, across an epoch of signal data. Method element 356 computes the difference between the maximum and minimum values to yield the peak-to-peak signal characteristic.

Figures 17, 17A:
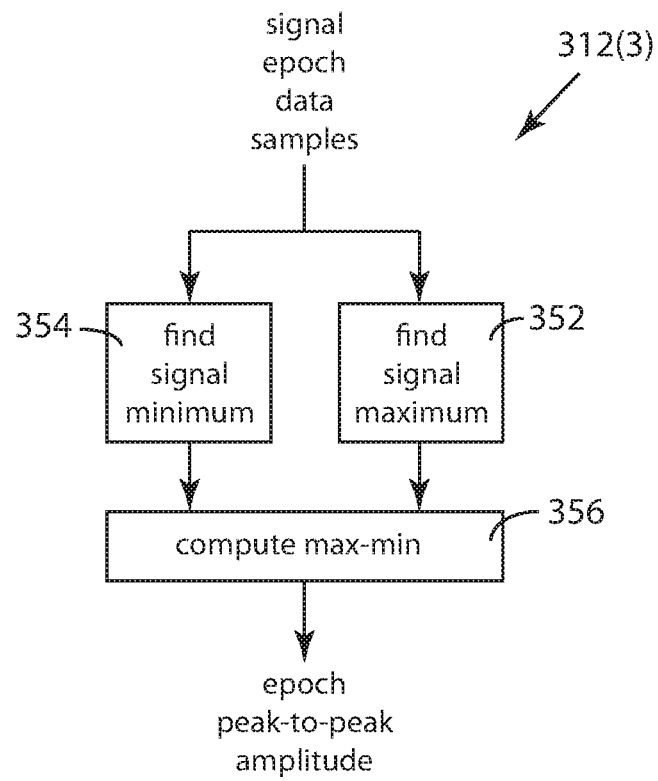
FIG. 17 is a schematic block diagram illustrating a second alternative method for computation of a signal characteristic for use within the method embodiment of FIG. 13. This alternative signal characteristic computation generates a signal characteristic epoch peak-to-peak amplitude.
FIG. 17A is a table illustrating the second alternative embodiment of FIG. 17, showing the peak-to-peak determination of the exemplary six-second epoch of a representative cardiac channel electrogram signal of FIG. 15A.

FIG. 17A is a table 358 illustrating second alternative embodiment 312(3) of FIG. 17, showing the peak-to-peak determination of the exemplary six-second epoch of the exemplary cardiac channel electrogram signal of FIG. 15A. The peak-to-peak value for the epoch of signal data values of FIG. 15A is found to be 1,731 μvolts. The epoch of signal data in FIG. 15A provides a good illustration of why an epoch duration of about six seconds is desirable, and this can be seen from at least three perspectives: six seconds is long enough to span several complete cycles of cardiac contraction; six seconds is long enough to span at least one respiratory cycle; and six seconds is long enough to obviate the need to carefully detect individual cardiac beats. By including these sources of variability entirely within, and therefore common to, an epoch, stability can be recognized from epoch to epoch. FIG. 15A clearly illustrates beat-to-beat variability within the span of a six-second epoch.

Figure 18:
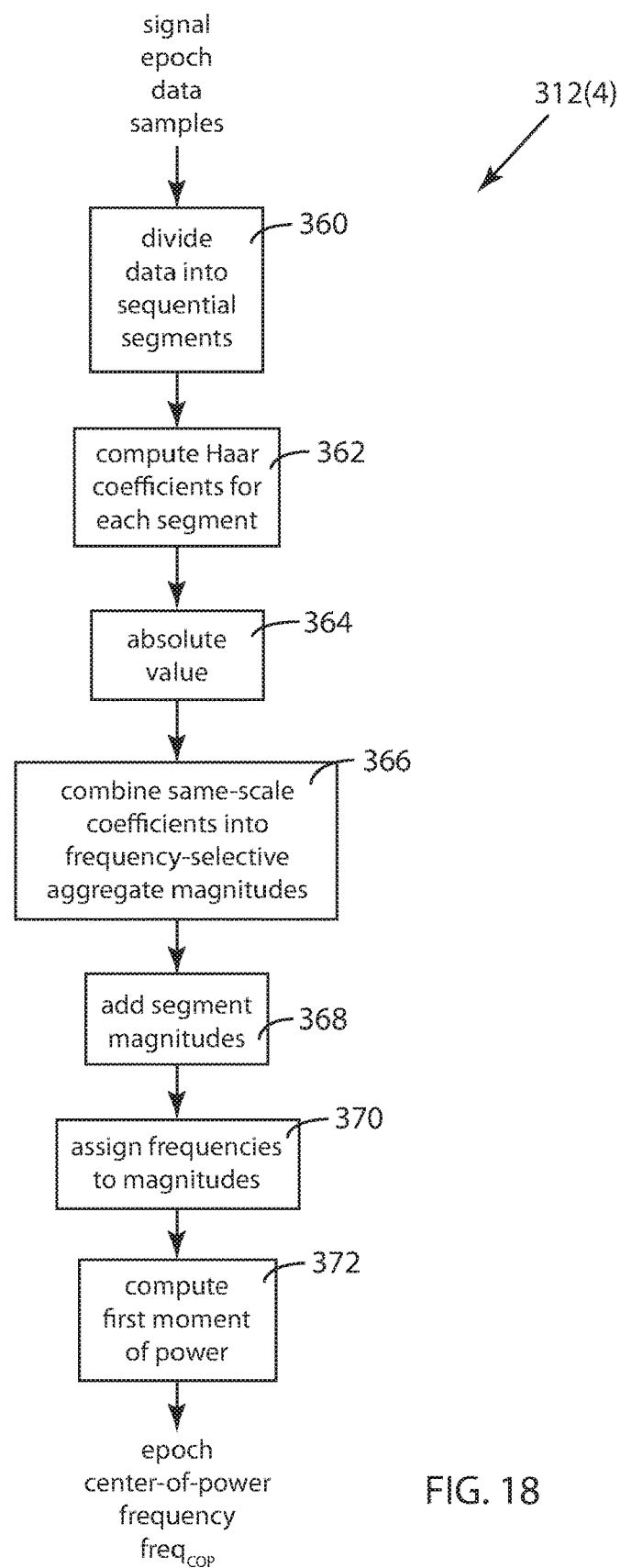
FIG. 18 is a schematic block diagram illustrating a third alternative method for computation of a signal characteristic for use within the method embodiment of FIG. 13. This alternative signal characteristic computation generates a Haar-transform-based parameter called the epoch center-of-power frequency.

FIG. 18 is a schematic block diagram illustrating an embodiment 313(4) of a third alternative method for computation of a signal characteristic for use within the method embodiment of FIG. 13. This alternative signal characteristic computation generates a Haar-transform-based parameter called the epoch center-of-power frequency freq$_{COP}$. In FIG. 18, signal epoch data is divided into sequential segments in method element 360. The division of signal epoch data into segments is useful for computational efficiency depending on the number of data values in an epoch of data. A Haar transform requires that the number of samples be a power of 2. Thus, for example, a six-second epoch of data captured at 1,000 sps contains 6,000 values, and such an epoch can be divided into three segments of 2,048 ($2^{11}$) values with only very modest overlap between the segments.

Figure 18A:
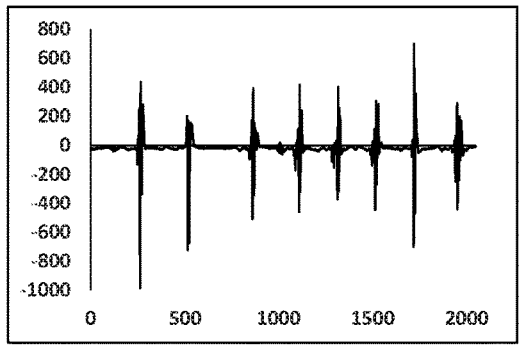
FIGS. 18A-18C are three plots of segments of the exemplary six-second epoch of a representative cardiac channel electrogram signal of FIG. 15A.
Figure 18D:
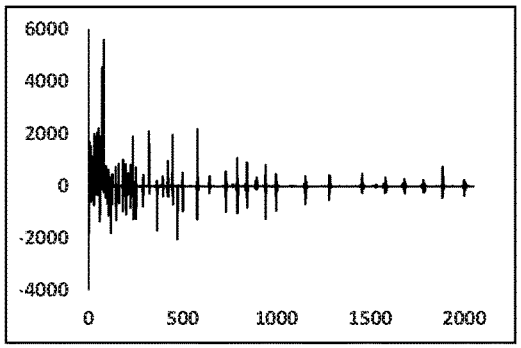
FIGS. 18D-18F are three plots of the Haar transformation coefficients for the three data segments of FIGS. 18A-18C, respectively, resulting from the Haar transformation of such three segments of data.
Figure 18B:
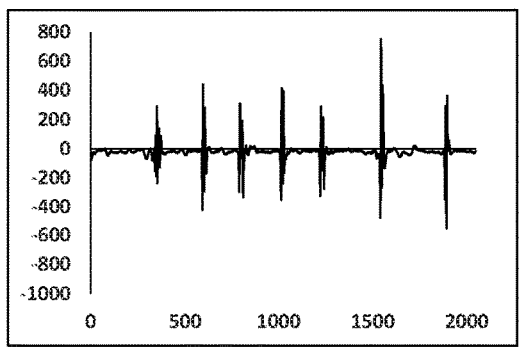
Figure 18E:
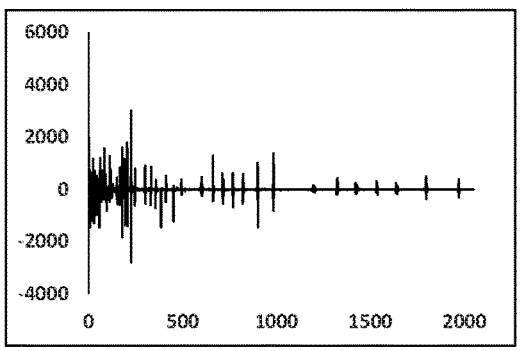
Figure 18C:
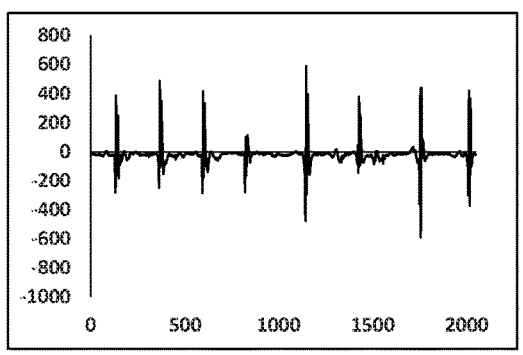

FIGS. 18A-18C illustrate the segmenting of the exemplary data of FIG. 15A into three sequential segments, each consisting of 2,048 values. Note that each segment is shown having sample indices from 1 to 2,048 although the actual index values range as follows: the plot of FIG. 18A includes epoch samples 1 through 2,048; the plot of FIG. 18B includes epoch samples 1,977 through 4,024; and the plot of FIG. 18C includes epoch samples 3,953 through 6,000. Again, as in FIGS. 15C-15G, the abscissa of each of the three plots in FIGS. 18A-18C span from 1 through 2,048 since the Haar transform to be performed is on each segment individually although the signal data is taken from different segments of the epoch as indicated above.

In method element 362, the Haar transformation coefficients for each segment of data are computed. The details of a Haar transformation are well known to those skilled in the art of signal processing. However, some details of such a computation will be described to illustrate certain aspects of method embodiment 312(4).

Figure 18F:
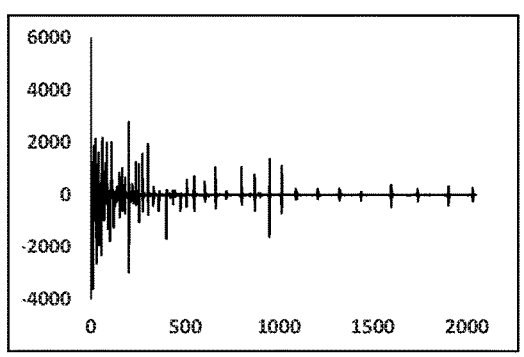

FIGS. 18D-18F are three plots of the Haar transformation coefficients for the three data segments of FIGS. 18A-18C, respectively, resulting from the Haar transformation of such three segments of data. These coefficients are computed as illustrated in the table of FIG. 18G. A Haar transformation is based on a series of signal differences as shown in FIG. 18G, and a signal having 2,048 data values results in 2,048 Haar transformation difference-related coefficients $H_i$.

The abscissa of the plots of FIGS. 18D-18F represent the 2,048 Haar coefficients, and the plots are not frequency spectra. Unlike an FFT, the Haar transformation coefficients do not constitute a frequency spectrum but rather are a set of difference terms as described further in FIG. 18G. $H_1$ is the sum of all 2,048 values in the segment of epoch data, and as such it represents the DC term in the signal (no differencing). $H_2$ is the difference between the sum of the second half of the signal values minus the sum of the first half of the values, and as such, represents information in the signal related to a cycle which is the full length of the epoch segment (2.048 seconds-0.488 Hz—in the exemplary data of FIG. 15A). The differencing continues by powers of two as shown in FIG. 18G up to $H_{2048}$ which is the difference between the last two signal values. The last 1,024 coefficients ($H_{1025}$ through $H_{2048}$) are the differences between neighboring pairs of signal values. These coefficients relate to the highest frequency information available in the transform which in the example being discussed is 500 Hz.

Note that in the description of FIG. 18G, the sign convention may differ from some descriptions of the Haar transform, but since the signal characteristic being computed is related to power, the absolute value of the coefficients is used and the sign convention is not relevant. Thus, in method element 364, an absolute value filter is applied to the Haar coefficients.

FIG. 18H shows a table detailing the computation of a set of eleven frequency-selective aggregate magnitudes $A_i$ from the 2,048 Haar transformation coefficients $H_i$ of FIG. 18G. The Haar transformation coefficients are aggregated in method element 366 of method embodiment 312(4) of FIG. 18 by combining the absolute values of the Haar transformation coefficients $H_i$ having like time scales as shown in FIG. 18H. Thus, for example, every difference of same-time-scale sets of signal values are summed in method element 368 of method embodiment 312(4) of FIG. 18 to form the frequency-selective aggregate magnitude related to the corresponding time scale. (The aggregate magnitudes are frequency-selective because they are formed from differences having the same time scales.)

Such aggregation results in a spectrum-like plot of frequency-selective aggregate magnitudes $A_i$ which then relate to certain frequencies which are assigned to the frequency-selective aggregate magnitudes in method element 370 of method embodiment 312(1). In the example being discussed, the frequency $F_i$ related to $A_i$ is $F_i=0.488 \times 2^{(i-1)}$, and these frequencies are shown in the table of FIG. 18H.

The final step in method embodiment 312(4), in method element 372, is a determination of a signal characteristic based on the Haar transformation, a center-of-power frequency freq$_{COP}$. One way to determine freq$_{COP}$ is to compute a first moment similar to that used for the FFT-based signal characteristic.

$$\text{freq}_{COP} = [\Sigma(A_i^2 \cdot F_i)]/\Sigma A_i^2$$

where the sum is over the 11 frequency-selective aggregate magnitudes $A_i$ and their corresponding frequencies $F_i$.

Figure 18I:
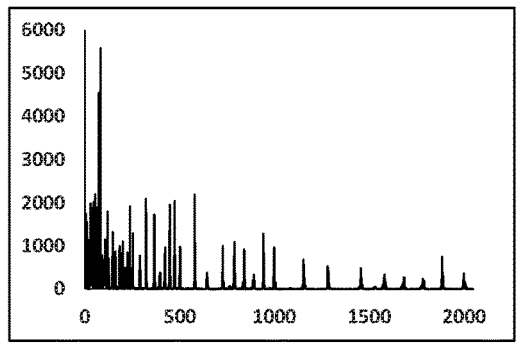
FIGS. 18I-18K are three plots of the absolute values of the Haar transformation coefficients shown in FIGS. 18D-18F for the three data segments of FIGS. 18A-18C, respectively.
Figure 18L:
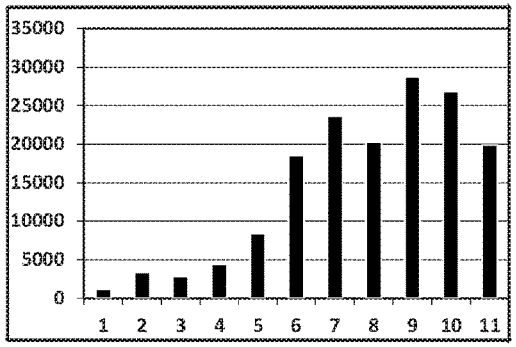
FIGS. 18L-18N are three bar charts of the eleven frequency-selective aggregate magnitudes $A_i$ for each of the three segments of signal data of FIGS. 18A-18C.
Figure 18J:
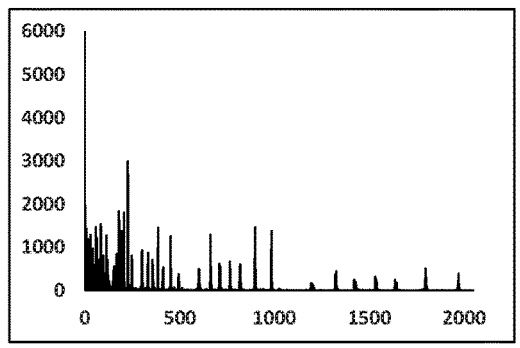
Figure 18M:
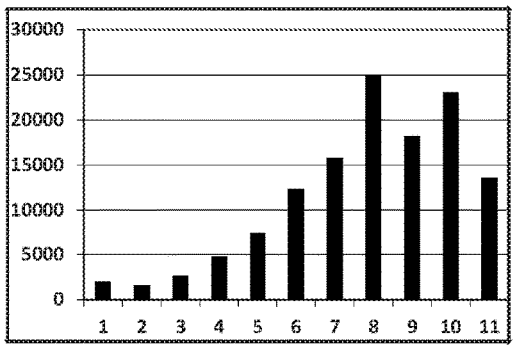
Figure 18K:
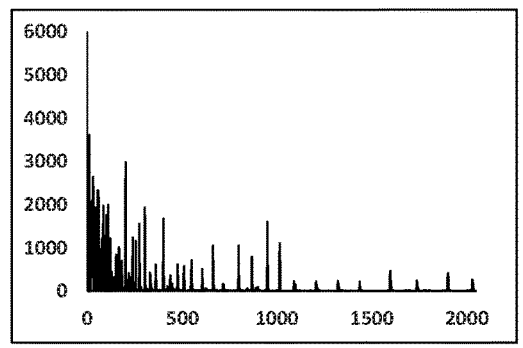
Figure 18N:
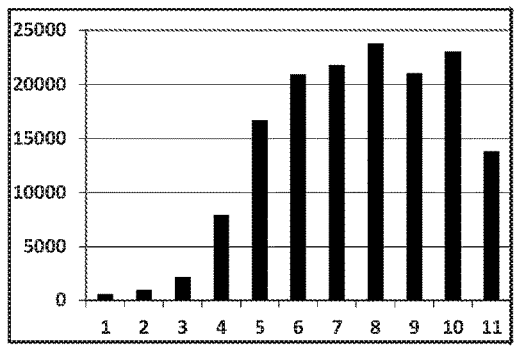

FIGS. 18I-18K are three plots of the absolute values of the Haar transformation coefficients shown in FIGS. 18D-18F for the three data segments of FIGS. 18A-18C, respectively, and FIGS. 18L-18N are three bar charts showing the values frequency-selective aggregate magnitudes $A_i$ for each of the three segments as shown in FIGS. 18A-18C and determined by applying the computations described in FIGS. 18G and 18H.

Figure 18P:
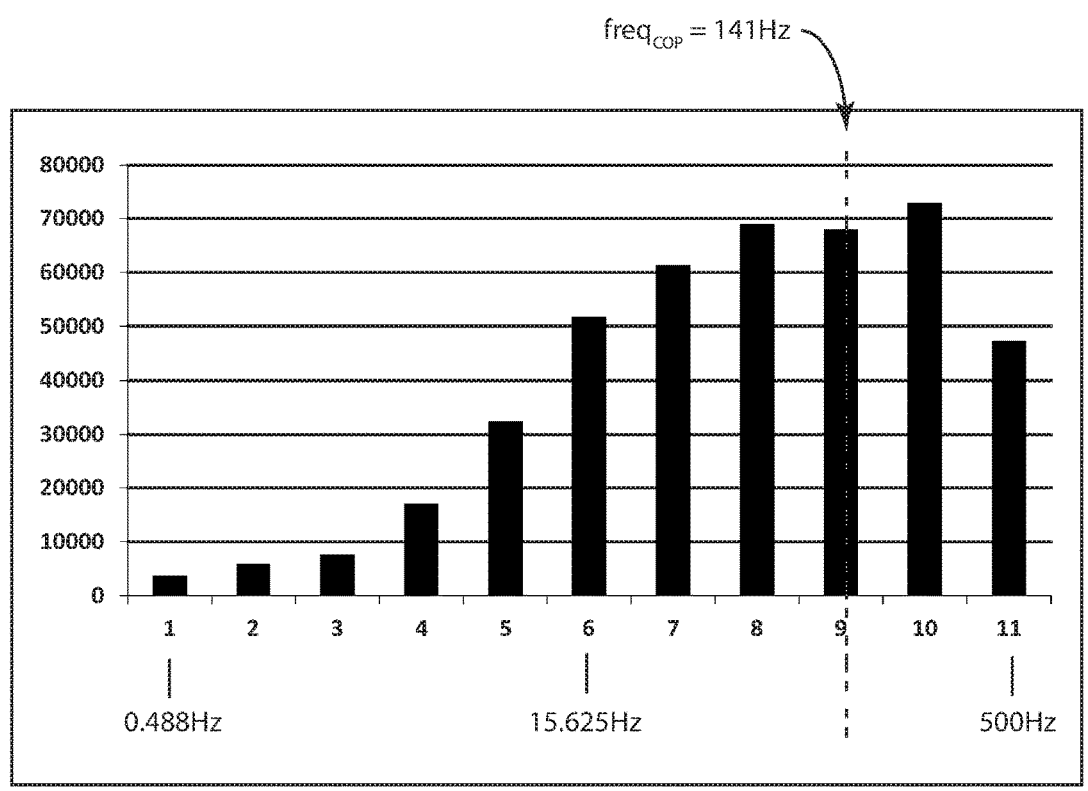
FIG. 18P is a bar chart presenting the eleven frequency-selective aggregate magnitudes used in the determination of a COP-frequency signal characteristic using the alternative method of FIG. 18.

FIG. 18P is a bar chart presenting the sum of the three sets of segments magnitudes $A_i$ from the Haar transformations of the three data segments. The eleven frequency-selective aggregate magnitudes of the abscissa are used in the determination of frequency-related signal characteristic freq$_{COP}$ using the Haar-transform-based method of FIG. 18. For the exemplary signal data of FIG. 15A, freq$_{COP}$ is found to be 141 Hz, and this is indicated in the chart of FIG. 18P.

Note that this frequency of 141 Hz differs from the 107 Hz found for the FFT-based computation of freq$_{COP}$. Such a difference is expected due to the logarithmic nature of the abscissa in the chart of FIG. 18P, but since comparisons are made using the same signal characteristic computation, what is important is the ability of the signal characteristic to be sensitive to differences in the signals. All of the methods exampled above for method element 312 of method embodiment 300 are able to detect such differences in signals.

While the principles of this invention have been described in connection with specific embodiments, it should be understood clearly that these descriptions are made only by way of example and are not intended to limit the scope of the invention.

The invention claimed is:

1. An automatic method of determining local activation time (LAT) from at least three multi-channel cardiac electrogram signals from a patient, such signals including a mapping channel and a plurality of reference channels, the method carried out during a medical procedure and comprising:

capturing, digitizing, and storing the cardiac channel signals;

using the mapping-channel signal and a first reference-channel signal to compute LAT values at a plurality of mapping-channel locations;

monitoring the timing stability of the first reference-channel signal; and if the timing stability of the monitored signal falls below a timing-stability standard, using a second reference-channel signal to determine LAT values and avoid substantial loss of LAT values in spite of loss of timing stability, thereby to reduce the duration of the medical procedure.

2. The automatic LAT-determining method of claim 1 further including computing one or more timing offsets using pairs of the plurality of reference-channel signals, a timing offset being $LAT_K(J)$, the local activation time of a reference channel J based on a reference channel K and used to transform an LAT value based on reference channel J to an LAT value based on reference channel K.

3. The automatic LAT-determining method of claim 2 wherein monitoring the timing stability of the first reference-channel signal includes monitoring multiple timing offsets $LAT_1(X)$ where X represents the channels with which timing offsets with the first reference channel are computed.

4. The automatic LAT-determining method of claim 3 further including computing a signal characteristic for the plurality of reference channels and determining therefrom which one or more channels among these reference channels has/have not lost timing stability.

5. The automatic LAT-determining method of claim 4 wherein computing a signal characteristic of a signal includes computing the frequency content of the signal.

6. The automatic LAT-determining method of claim 5 wherein computing the frequency content of the signal includes computing a fast Fourier transform for a predetermined time period of the signal.

7. The automatic LAT-determining method of claim 6 wherein the signal is segmented into a plurality of time-overlapping segment signals.

8. The automatic LAT-determining method of claim 7 wherein weightings are applied to each of the segment signals.

9. The automatic LAT-determining method of claim 8 wherein computing the fast Fourier transform of the signal includes (a) computing a signal-segment fast Fourier transform for each segment signal and (b) averaging each such signal-segment fast Fourier transform to form the fast Fourier transform of the signal.

10. The automatic LAT-determining method of claim 9 wherein the computed signal characteristic is the first moment of the signal power determined from the fast Fourier transform of the signal.

11. The automatic LAT-determining method of claim 6 wherein the computed signal characteristic is the first moment of the signal power determined from the fast Fourier transform.

12. The automatic LAT-determining method of claim 5 wherein computing the frequency content of the signal includes computing a Haar transform for a predetermined time period of the signal.

13. The automatic LAT-determining method of claim 12 wherein the signal is segmented into a plurality of substantially-sequential segment signals.

14. The automatic LAT-determining method of claim 13 wherein computing the Haar transform of the signal includes (a) computing Haar transform coefficients for each segment signal, (b) computing absolute values of the coefficients, (c) computing a set of frequency-selective aggregate magnitudes for each segment signal by summing signal-segment Haar transform coefficients having like time scales, and (d) averaging the sets of frequency-selective aggregate magnitudes to form a single set of frequency-selective aggregate magnitudes for the signal.

15. The automatic LAT-determining method of claim 14 wherein the computed signal characteristic is the first moment of the signal power determined from the frequency-selective aggregate magnitudes.

16. The automatic LAT-determining method of claim 12 wherein the computed signal characteristic is the first moment of the signal power determined from the computed Haar transform.

17. The automatic LAT-determining method of claim 5 wherein computing the frequency content of the signal includes computing a Fourier transform for a predetermined time period of the signal.

18. The automatic LAT-determining method of claim 4 further including selecting the second reference-channel signal from channels which have not lost timing stability.

19. The automatic LAT-determining method of claim 18 wherein selecting the second reference-channel signal from channels which have not lost timing stability includes computing signal quality.

20. The automatic LAT-determining method of claim 4 wherein the computed signal characteristic is the fraction of time within a predetermined time period of the signal at which the absolute value of signal velocity is above a predetermined threshold.

21. The automatic LAT-determining method of claim 4 wherein the computed signal characteristic is the maximum signal amplitude minus the minimum signal amplitude within a predetermined time period of the signal.

22. The automatic LAT-determining method of claim 2 wherein using the second reference-channel signal to determine LAT values includes transforming future LAT values such that they are based on the first reference channel.

23. The automatic LAT-determining method of claim 22 wherein:

$LAT_2(M)$ is a future LAT value of mapping channel M based on the second reference channel; and future transformed values $LAT_1(M)$ of mapping channel M based on the first reference channel are equal to a timing offset $LAT_1(2)$ plus $LAT_2(M)$.

24. The automatic LAT-determining method of claim 2 wherein using the second reference-channel signal to determine LAT values includes transforming past LAT values such that they are based on the second reference channel.

25. The automatic LAT-determining method of claim 24 wherein:

$LAT_1(M)$ is a past LAT value of mapping channel M based on the first reference channel; and past transformed values $LAT_2(M)$ of mapping channel M based on the second reference channel are equal to a timing offset $LAT_2(1)$ plus $LAT_1(M)$.

26. The automatic LAT-determining method of claim 2 wherein the one or more timing offsets are computed at a plurality of times, and the value of each timing offset is replaced with its average over the plurality of times.

27. The automatic LAT-determining method of claim 26 wherein the average is computed over a predetermined number of times.

\* \* \* \* \*